(12) United States Patent
Cumming et al.

(10) Patent No.: US 9,489,013 B2
(45) Date of Patent: Nov. 8, 2016

(54) C6-AZASPIRO IMINOTHIADIAZINE DIOXIDES AS BACE INHIBITORS, COMPOSITIONS, AND THEIR USE

(71) Applicant: Merck Sharp & Dohme Corp., Rahway, NJ (US)

(72) Inventors: Jared N. Cumming, Garwood, NJ (US); David Earl Kaelin, Jr., East Brunswick, NJ (US); Jack D. Scott, Scotch Plains, NJ (US); Andrew W. Stamford, Chatham, NJ (US); Ulrich Iserloh, Hoboken, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/653,681

(22) PCT Filed: Dec. 16, 2013

(86) PCT No.: PCT/US2013/075369
§ 371 (c)(1),
(2) Date: Jun. 18, 2015

(87) PCT Pub. No.: WO2014/130146
PCT Pub. Date: Aug. 28, 2014

(65) Prior Publication Data
US 2016/0043774 A1 Feb. 11, 2016

Related U.S. Application Data

(60) Provisional application No. 61/740,101, filed on Dec. 20, 2012.

(51) Int. Cl.
*C07D 417/14* (2006.01)
*C07D 417/04* (2006.01)
*G06F 1/16* (2006.01)

(52) U.S. Cl.
CPC .................................. *G06F 1/1616* (2013.01)

(58) Field of Classification Search
CPC .......................... C07D 417/14; C07D 417/04
USPC ............................................ 544/6; 514/222.5
See application file for complete search history.

(56) References Cited

U.S. PATENT DOCUMENTS

| | | | |
|---|---|---|---|
| 5,534,520 | A | 7/1996 | Fisher et al. |
| 2006/0111370 | A1 | 5/2006 | Zhu et al. |
| 2010/0075957 | A1 | 3/2010 | Tamura et al. |
| 2012/0035195 | A1 | 2/2012 | Banner et al. |
| 2012/0183563 | A1 | 7/2012 | Scott et al. |
| 2014/0235626 | A1 | 8/2014 | Tada et al. |

FOREIGN PATENT DOCUMENTS

| | | |
|---|---|---|
| EP | 1942105 | 7/2008 |
| WO | 2005058311 | 6/2005 |
| WO | 2006065277 A2 | 6/2006 |
| WO | 2006138217 A1 | 12/2006 |
| WO | 2007049532 A1 | 5/2007 |
| WO | 2007050721 A2 | 5/2007 |
| WO | 2007146225 A2 | 12/2007 |
| WO | 2008103351 | 8/2008 |
| WO | 2010047372 | 4/2010 |
| WO | 2010128058 | 11/2010 |
| WO | 2011044181 | 4/2011 |
| WO | 2011044184 | 4/2011 |
| WO | 2011044185 | 4/2011 |
| WO | 2011044187 A1 | 4/2011 |
| WO | 2011070029 | 6/2011 |
| WO | 2011071135 A1 | 6/2011 |
| WO | 2011077726 | 6/2011 |
| WO | 2011154431 | 12/2011 |
| WO | 2012071279 | 5/2012 |
| WO | 2012138590 A1 | 10/2012 |
| WO | 2012138734 A1 | 10/2012 |
| WO | 2014099788 A1 | 6/2014 |
| WO | 2015038446 A1 | 3/2015 |
| WO | 2015094930 A1 | 6/2015 |

*Primary Examiner* — Kahsay Habte
(74) *Attorney, Agent, or Firm* — Keith D. MacMillan; John C. Todaro

(57) ABSTRACT

In its many embodiments, the present invention provides certain C2-ring-substituted thiadiazine compounds, including compounds Formula (I): (structure represented) or tautomers thereof, and pharmaceutically acceptable salts of said compounds and said tautomers, wherein $R^1$, $R^4$, ring A, $R^A$, m, -$L_1$-, $R^L$, and ring C are as defined herein. The novel compounds of the invention are useful as BACE inhibitors and/or for the treatment and prevention of various pathologies related thereto. Pharmaceutical compositions comprising one or more such compounds (alone and in combination with one or more other active agents), and methods for their preparation and use, including for the possible treatment of Alzheimer's disease, are also disclosed.

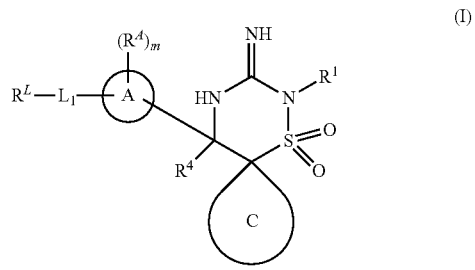

(I)

11 Claims, No Drawings

C6-AZASPIRO IMINOTHIADIAZINE DIOXIDES AS BACE INHIBITORS, COMPOSITIONS, AND THEIR USE

FIELD OF THE INVENTION

This invention provides certain C6-azaspiro iminothiadiazine dioxide compounds, and compositions comprising these compounds, as inhibitors of BACE, which may be useful for treating or preventing pathologies related thereto.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis (β2 microglobulins and complications arising therefrom), neurodegenerative diseases such as scrapie, bovine spongiform encephalitis, Creutzfeld-Jakob disease, traumatic brain injury and the like.

Aβ peptides are short peptides which are made from the proteolytic break-down of the transmembrane protein called amyloid precursor protein ("APP"). Aβ peptides are made from the cleavage of APP by β-secretase activity at a position near the N-terminus of Aβ, and by gamma-secretase activity at a position near the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of Aβ by β-secretase activity. The inhibition of BACE-1 has been shown to inhibit the production of Aβ.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and gamma-secretase activity, can form tertiary structures that aggregate to form amyloid fibrils. Aβ peptides have also been shown to form Aβ oligomers (sometimes referred to as "Aβ aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ, Aβ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuronal cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of Aβ-driven AD-like pathology, making β-secretase a target for therapeutic intervention in AD. Ohno et al. Neurobiology of Disease, No. 26 (2007), 134-145, report that genetic deletion of BACE-1 in 5XFAD mice abrogates Aβ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that Aβ is ultimately responsible for neuron death in AD and concludes that BACE-1 inhibition has been validated as an approach for the treatment of AD. Roberds et al., Human Mol. Genetics, 2001, Vol. 10, No. 12, 1317-1324, established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation.

More recently, Jonsson, et al. have reported in Nature, Vol. 488, pp. 96-99 (August 2012), that a coding mutation (A673T) in the APP gene protects against Alzheimer's disease and cognitive decline in the elderly without Alzheimer's disease. More specifically, the A allele of rs63750847, a single nucleotide polymorphism (SNP), results in an alanine to threonine substitution at position 673 in APP (A673T). This SNP was found to be significantly more common in a healthy elderly control group than in an Alzheimer's disease group. The A673T substitution is adjacent to the aspartyl protease beta-site in APP, and results in an approximately 40% reduction in the formation of amyloidogenic peptides in a heterologous cell expression system in vitro. Jonsson, et al. report that an APP-derived peptide substrate containing the A673T mutation is processed 50% less efficiently by purified human BACE1 enzyme when compared to a wild-type peptide. Jonsson et al. indicate that the strong protective effect of the APP-A673T substitution against Alzheimer's disease provides proof of principle for the hypothesis that reducing the beta-cleavage of APP may protect against the disease.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., Ann NY Acad Sci 2002; 855:723-31; Crino P B, Martin J A, Hill W D, et al., Ann Otol Rhinol Laryngol, 1995; 104:655-61; Davies D C, et al., Neurobiol Aging, 1993; 14:353-7; Devanand D P, et al., Am J Psychiatr, 2000; 157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and IAPP, but lacking in the other endocrine and exocrine cell types. Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other diverse pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"), Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, Loane, et al. report the targeting of amyloid precursor protein secretases as therapeutic targets for traumatic brain injury. (Loane et al., "Amyloid precursor protein secretases as therapeutic targets for traumatic brain injury", Nature Medicine, Advance Online Publication, published online Mar. 15, 2009.) Still other diverse pathologies characterized by the inappropriate formation and deposition of Aβ or fragments thereof, and/or by the presence of amyloid fibrils, and/or for which inhibitor(s) of BACE-1 is expected to be of therapeutic value are discussed further hereinbelow.

SUMMARY OF THE INVENTION

The present invention provides certain C6-azaspiro thiadiazine dioxide compounds, which are collectively or individually referred to herein as "compound(s) of the invention", as described herein. The compounds of the invention are useful as inhibitors of BACE-1 and/or BACE-2.

In one embodiment, the compounds of the invention have the structural Formula (I):

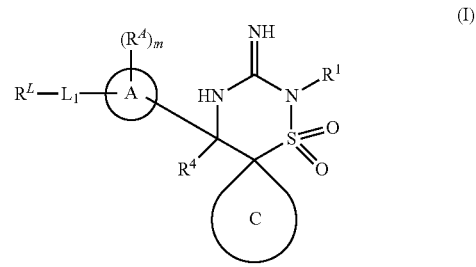

or a tautomer thereof having the structural Formula (I'):

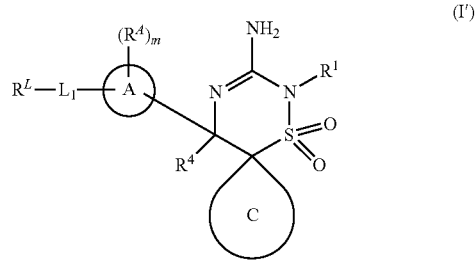

and pharmaceutically acceptable salts thereof, wherein:
$R^1$ is selected from the group consisting of H, alkyl, heteroalkyl, cycloalkyl, and -alkyl-cycloalkyl, wherein each said alkyl, heteroalkyl, cycloalkyl, and -alkyl-cycloalkyl is optionally substituted with one or more halogen;

ring C is a moiety selected from the group consisting of

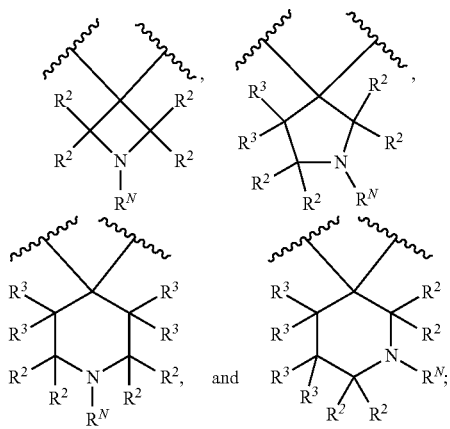

each R² is independently selected from the group consisting of H, -alkyl-OH, alkyl, heteroalkyl, and cycloalkyl wherein each said alkyl, heteroalkyl, and cycloalkyl of R² is optionally substituted with halogen;

each R³ is independently selected from the group consisting of H, halogen, -alkyl-OH, alkyl, heteroalkyl, alkoxy, and cycloalkyl, wherein each said alkyl, heteroalkyl, alkoxy, and cycloalkyl of R³ is optionally substituted with halogen;

$R^N$ is selected from the group consisting of: H, —C(O) $R^{6N}$, —C(O)O$R^{6N}$, —C(O)N($R^{6N}$)$_2$, —S(O)$_2R^{6N}$, —S(O)$_2$N($R^{6N}$)$_2$, alkyl, heteroalkyl, cycloalkyl, -alkyl-cycloalkyl, heterocycloalkyl, -alkyl-heterocycloalkyl, aryl, -alkyl-aryl, heteroaryl, and -alkyl-heteroaryl, wherein said alkyl, heteroalkyl, cycloalkyl, -alkyl-cycloalkyl, heterocycloalkyl, -alkyl-heterocycloalkyl, aryl, -alkyl-aryl, heteroaryl, and -alkyl-heteroaryl, of $R^N$ are each optionally independently unsubstituted or substituted with one or more groups independently selected from $R^9$;

R⁴ is selected from the group consisting of H, alkyl, heteroalkyl, cycloalkyl, -alkyl-cycloalkyl, heterocycloalkyl, and -alkyl-heterocycloalkyl, wherein each said alkyl, heteroalkyl, cycloalkyl, -alkyl-cycloalkyl, heterocycloalkyl, and -alkyl-heterocycloalkyl is optionally substituted with one or more halogen;

ring A is selected from the group consisting of aryl and heteroaryl;

m is 0 or more;

each $R^A$ (when present) is independently selected from the group consisting of: halogen, oxo, —OH, —CN, —SF$_5$, —OSF$_5$, —Si($R^{5A}$)$_3$, —N($R^{6A}$)$_2$, —O$R^{6A}$, —S$R^{6A}$, alkyl, heteroalkyl, alkenyl, alkynyl, cycloalkyl, -alkyl-cycloalkyl, heterocycloalkyl, and -alkyl-heterocycloalkyl, wherein said alkyl, heteroalkyl, alkenyl, alkynyl, cycloalkyl, -alkyl-cycloalkyl, heterocycloalkyl, and -alkyl-heterocycloalkyl of $R^A$ are each optionally independently unsubstituted or substituted with one or more groups independently selected from $R^8$;

-L$_1$- is a divalent moiety selected from the group consisting of —NHC(O)— and —C(O)NH—;

$R^L$ is selected from the group consisting of alkyl and heteroalkyl, wherein said alkyl and heteroalkyl of $R^L$ are each optionally unsubstituted or substituted with one or more halogen;

or, alternatively, $R^L$ is a moiety having the formula

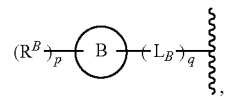

wherein q is 0 or 1;

-L$_B$- (when present) is a divalent moiety selected from the group consisting of lower alkyl and lower heteroalkyl, wherein each said lower alkyl and lower heteroalkyl is optionally substituted with one or more halogen;

ring B is selected from the group consisting of aryl, heteroaryl, cycloalkyl, cycloalkenyl, heterocycloalkyl, and heterocycloalkenyl;

p is 0 or more; and each $R^B$ (when present) is independently selected from the group consisting of: halogen, oxo, —OH, —CN, —SF$_5$, —OSF$_5$, —Si($R^{5B}$)$_3$, —N($R^{6B}$)$_2$, —N$R^{7B}$C(O)$R^{6B}$, —N$R^{7B}$S(O)$_2R^{6B}$, —N$R^{7B}$S(O)$_2$N($R^{6B}$)$_2$, —N$R^{7B}$C(O)N($R^{6B}$)$_2$, —N$R^{7B}$C(O)O$R^{6B}$, —C(O)$R^{6B}$, —C(O)O$R^{6B}$, —C(O)N($R^{6B}$)$_2$, —S(O)$R^{6B}$, —S(O)$_2R^{6B}$, —S(O)$_2$N($R^{6B}$)$_2$, —O$R^{6B}$, —S$R^{6B}$, alkyl, heteroalkyl, alkenyl, alkynyl, cycloalkyl, -alkyl-cycloalkyl, heterocycloalkyl, -alkyl-heterocycloalkyl, aryl, -alkyl-aryl, heteroaryl, and -alkyl-heteroaryl.

wherein said alkyl, heteroalkyl, alkenyl, alkynyl, cycloalkyl, -alkyl-cycloalkyl, heterocycloalkyl, -alkyl-heterocycloalkyl, aryl, -alkyl-aryl, heteroaryl, and -alkyl-heteroaryl, of $R^B$ are each optionally independently unsubstituted or substituted with one or more groups independently selected from $R^9$;

each $R^{5A}$ and $R^{5B}$ (when present) is independently selected from the group consisting of alkyl, heteroalkyl, cycloalkyl, -alkyl-cycloalkyl, heterocycloalkyl, -alkyl-heterocycloalkyl, wherein each said alkyl, heteroalkyl, cycloalkyl, -alkyl-cycloalkyl, heterocycloalkyl, -alkyl-heterocycloalkyl of $R^{5A}$ and $R^{5B}$ is unsubstituted or substituted with one or more halogen;

each $R^{6N}$ and $R^{6A}$ (when present) is independently selected from the group consisting of H, alkyl, -alkyl-OH, alkenyl, alkynyl, heteroalkyl, -heteroalkyl-OH, cycloalkyl, -alkyl-cycloalkyl, heterocycloalkyl, -alkyl-heterocycloalkyl, aryl, heteroaryl, -alkyl-aryl, and -alkyl-heteroaryl, wherein each said alkyl, -alkyl-OH, alkenyl, alkynyl, heteroalkyl, -heteroalkyl-OH, cycloalkyl, -alkyl-cycloalkyl, heterocycloalkyl, -alkyl-heterocycloalkyl, aryl, -alkyl-aryl, heteroaryl, and -alkyl-heteroaryl of $R^{6N}$ and $R^{6A}$ is unsubstituted or substituted with one or more groups independently selected from halogen, alkyl, cycloalkyl, heteroalkyl, haloalkyl, alkoxy, heteroalkoxy, and haloalkoxy;

each $R^{6B}$ (when present) is independently selected from the group consisting of H, alkyl, -alkyl-OH, alkenyl, alkynyl, heteroalkyl, -heteroalkyl-OH, cycloalkyl, -alkyl-cycloalkyl, heterocycloalkyl, -alkyl-heterocycloalkyl, aryl, -alkyl-aryl, heteroaryl, and -alkyl-heteroaryl, wherein each said alkyl, -alkyl-OH, alkenyl, alkynyl, heteroalkyl, -heteroalkyl-OH, cycloalkyl, -alkyl-cycloalkyl, heterocycloalkyl, -alkyl-heterocycloalkyl, aryl, -alkyl-aryl, heteroaryl, and -alkyl-heteroaryl of $R^{6B}$ is unsubstituted or substituted with one or more groups independently selected from halogen, alkyl, cycloalkyl, heteroalkyl, haloalkyl, alkoxy, heteroalkoxy, and haloalkoxy;

each $R^{7B}$ (when present) is independently selected from the group consisting of H, alkyl, heteroalkyl, cycloalkyl, -alkyl-cycloalkyl, heterocycloalkyl, and -alkyl-heterocycloalkyl, wherein each said alkyl, heteroalkyl, -heteroalkyl-OH, cycloalkyl, -alkyl-cycloalkyl, heterocycloalkyl, and -alkyl-heterocycloalkyl of $R^{7B}$ is unsubstituted or substituted with one or more halogen;

each $R^8$ (when present) is independently selected from the group consisting of halogen, lower alkyl, lower heteroalkyl, lower alkoxy, lower cycloalkyl, and lower heterocycloalkyl, wherein each said lower alkyl, lower heteroalkyl, lower alkoxy, lower cycloalkyl, and lower heterocycloalkyl of $R^8$ is optionally substituted with halogen; and each $R^9$ (when present) is independently selected from the group consisting of halogen, —OH, —CN, —SF$_5$, —OSF$_5$, alkyl, -alkyl-OH, heteroalkyl, -heteroalkyl-OH, alkoxy, —O-heteroalkyl, cycloalkyl, -alkyl-cycloalkyl, —O-cycloalkyl, —O-alkyl-cycloalkyl, -heterocycloalkyl, -alkyl-heterocycloalkyl, —O-heterocycloalkyl and —O-alkyl-heterocycloalkyl, wherein each said alkyl, -alkyl-OH, heteroalkyl, -heteroalkyl-OH, alkoxy, —O-heteroalkyl, cycloalkyl, -alkyl-cycloalkyl, —O-cycloalkyl, —O-alkyl-cycloalkyl, -heterocycloalkyl, -alkyl-heterocycloalkyl, —O-heterocycloalkyl and —O-alkyl-heterocycloalkyl are optionally substituted with one or more halogen.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents suitable for treating the patient being treated.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I) or (IA). In each of the embodiments described herein, each variable is selected independently of the other unless otherwise noted.

In one embodiment, the compounds of the invention have the structural Formula (IA):

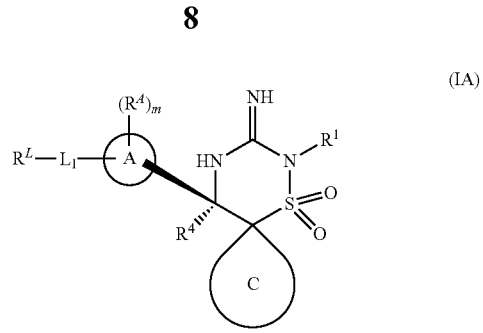

or a tautomer thereof having the structural Formula (IA'):

or pharmaceutically acceptable salt thereof, wherein each variable is as described in Formula (I).

In one embodiment, in each of Formulas (I), (I'), (IA), and (IA'):

$R^1$ is selected from the group consisting of H, methyl, ethyl, cyclopropyl, —CH$_2$-cyclopropyl, and —CH$_2$OCH$_3$.

In one embodiment, in each of Formulas (I), (I'), (IA), and (IA'):

$R^1$ is selected from the group consisting of H and methyl.

In one embodiment, in each of Formulas (I), (I'), (IA), and (IA'):

$R^1$ is methyl.

In one embodiment, in each of Formulas (I), (I'), (IA), and (IA'):

each $R^2$ is independently selected from the group consisting of H, methyl, ethyl, propyl, —CH$_2$OH, —CH$_2$CH$_2$OH, —CH$_2$OCH$_3$, —CH$_2$OCH$_2$CH$_3$, cyclopropyl, —CF$_3$, —CHF$_2$, and —CH$_2$F.

In one embodiment, in each of Formulas (I), (I'), (IA), and (IA'):

each $R^2$ is independently selected from the group consisting of H, methyl, ethyl, —CH$_2$OH, —CH$_2$OCH$_3$, cyclopropyl, —CF$_3$, —CHF$_2$, and —CH$_2$F.

In one embodiment, in each of Formulas (I), (I'), (IA), and (IA'):

each $R^2$ is independently selected from the group consisting of H, methyl, —CH$_2$OH, —CF$_3$, —CHF$_2$, and —CH$_2$F.

In one embodiment, in each of Formulas (I), (I'), (IA), and (IA'):

each $R^2$ is H.

In one embodiment, in each of Formulas (I), (I'), (IA), and (IA'):

each $R^3$ is independently selected from the group consisting of H, fluoro, chloro, methyl, ethyl, propyl, —CH$_2$OH, —CH$_2$CH$_2$OH, —CH$_2$OCH$_3$, —CH$_2$OCH$_2$CH$_3$, —OCH$_3$, —OCH$_2$CH$_3$, cyclopropyl, —CF$_3$, —CHF$_2$, —CH$_2$F, —OCF$_3$, —OCH$_2$CF$_3$, —OCHF$_2$, —OCH$_2$F, —OCH$_2$CH$_2$F.

In one embodiment, in each of Formulas (I), (I'), (IA), and (IA'):

each $R^3$ is independently selected from the group consisting of H, fluoro, methyl, ethyl, —CH$_2$OH, —CH$_2$OCH$_3$, —OCH$_3$, cyclopropyl, —CF$_3$, —CHF$_2$, —CH$_2$F, —OCHF$_2$, and —OCH$_2$F.

In one embodiment, in each of Formulas (I), (I'), (IA), and (IA'):

each $R^3$ is independently selected from the group consisting of H, methyl, —CH$_2$OH, —CF$_3$, —CHF$_2$, and —CH$_2$F.

In one embodiment, in each of Formulas (I), (I'), (IA), and (IA'):

each $R^3$ is H.

In one embodiment, in each of Formulas (I), (I'), (IA), and (IA'):

$R^N$ is as defined above; and each $R^{6N}$ is independently selected from the group consisting of H, lower alkyl, lower heteroalkyl, lower cycloalkyl, -(lower alkyl)-(lowercycloalkyl), lower heterocycloalkyl, -(lower alkyl)-(lower heterocycloalkyl), aryl, heteroaryl, -(lower alkyl)-aryl, and -(lower alkyl)-heteroaryl, wherein each said lower alkyl, lower heteroalkyl, lower cycloalkyl, -(lower alkyl)-(lowercycloalkyl), lower heterocycloalkyl, -(lower alkyl)-(lower heterocycloalkyl), aryl, heteroaryl, -(lower alkyl)-aryl, and -(lower alkyl)-heteroaryl of $R^{6N}$ is unsubstituted or substituted with one or more groups independently selected from halogen, lower alkyl, lower cycloalkyl, lower heteroalkyl, lower haloalkyl, lower alkoxy, lower heteroalkoxy, and lower haloalkoxy;

In one embodiment, in each of Formulas (I), (I'), (IA), and (IA'):

each $R^N$ group is selected from the group consisting of H, —C(O)CH$_3$, —C(O)CH$_2$CH$_3$, —C(O)CH$_2$CH(CH$_3$)$_2$, —C(O)-cyclopropyl, —C(O)—CH$_2$-cyclopropyl, —C(O)N(CH$_3$)$_2$, —C(O)NHCH$_3$, —S(O)$_2$CH$_3$, —S(O)$_2$CH$_2$CH$_3$, —S(O)$_2$CH$_2$CF$_3$, —S(O)$_2$CH$_2$CH(CH$_3$)$_2$, —S(O)$_2$-phenyl, —S(O)$_2$CH$_2$-pyridyl, —S(O)$_2$-cyclopentyl, —S(O)$_2$-cyclopropyl, —S(O)$_2$-imidazolyl, —S(O)$_2$—CH$_2$-tetrahydrofuranyl, —S(O)$_2$-pyrazolyl, —S(O)$_2$N(CH$_3$)$_2$, —S(O)$_2$NHCH$_3$, methyl, ethyl, propyl, cyclopropyl, butyl, —CH$_2$-cyclopropyl, benzyl, —CH$_2$OCH$_3$, —CH$_2$OCH$_2$CH$_3$, phenyl, pyridyl, pyrimidinyl, pyrazinyl, oxadiazolyl, isoxazolyl, oxazolyl, and pyrrolyl, —CH$_2$-thiazolyl, —CH$_2$-oxazoyl, —CH$_2$-pyridyl, —CH$_2$-pyrimidinyl, —CH$_2$-pyrazinyl, —CH$_2$-pyrazolyl, —CH$_2$-cyclobutyl, —CH$_2$-cyclopropyl, —CH$_2$-tetrahydrofuranyl, wherein said methyl, ethyl, propyl, butyl, —CH$_2$-cyclopropyl, benzyl, cyclobutyl, cyclopropyl, phenyl, pyridyl, oxadiazolyl, imidazolyl, isoxazolyl, oxazolyl, and pyrrolyl are each optionally unsubstituted or substituted with fluorine, chlorine, methyl, —CN, —CF$_3$, CHF$_2$, and —OMe.

In one embodiment, in each of Formulas (I), (I'), (IA), and (IA'):

each $R^N$ group is selected from the group consisting of H, —C(O)CH$_3$, —C(O)CH$_2$CH(CH$_3$)$_2$, —C(O)-cyclopropyl, —C(O)—CH$_2$-cyclopropyl, —S(O)$_2$CH$_3$, —S(O)$_2$CH$_2$CH$_3$, —S(O)$_2$CH$_2$CF$_3$, —S(O)$_2$CH$_2$CH(CH$_3$)$_2$, —S(O)$_2$-phenyl, —S(O)$_2$CH$_2$-pyridyl, —S(O)$_2$-cyclopentyl, —S(O)$_2$-cyclopropyl, —S(O)$_2$-imidazolyl, —S(O)$_2$CH$_2$-tetrahydrofuranyl, —S(O)$_2$-pyrazolyl, butyl, —CH$_2$-cyclopropyl, benzyl, —CH$_2$CH$_2$CF$_3$, —CH$_2$-thiazolyl, —CH$_2$-oxazoyl, —CH$_2$-pyridyl, —CH$_2$-pyrimidinyl, —CH$_2$-pyrazolyl, —CH$_2$-cyclobutyl, —CH$_2$-cyclopropyl, —CH$_2$-tetrahydrofuranyl, In one embodiment, in each of Formulas (I), (I'), (IA), and (IA'):

each $R^2$ is H; and each $R^3$ is independently selected from the group consisting of H and fluorine.

In one embodiment, in each of Formulas (I), (I'), (IA), and (IA'), $R^4$ is selected from the group consisting of H, methyl, ethyl, cyclopropyl, —CH$_2$-cyclopropyl, —CH$_2$F, —CHF$_2$, —CF$_3$, and —CH$_2$OCH$_3$.

In one embodiment, in each of Formulas (I), (I'), (IA), and (IA'), $R^4$ is selected from the group consisting of methyl, cyclopropyl, —CH$_2$F, and —CHF$_2$.

In one embodiment, in each of Formulas (I), (I'), (IA), and (IA'), $R^4$ is selected from the group consisting of methyl and —CHF$_2$.

In one embodiment, in each of Formulas (I), (I'), (IA), and (IA'):

$R^1$ is methyl;

each $R^2$ is H;

each $R^3$ is independently selected from the group consisting of H and fluorine; and $R^4$ is selected from the group consisting of methyl and —CHF$_2$.

The following alternatives of ring A are applicable to any of the embodiments described hereinabove.

In one embodiment, in each of Formulas (I), (I'), (IA), and (IA'):

ring C is:

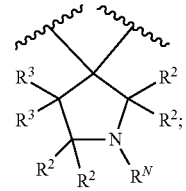

$R^1$ is methyl;

each $R^2$ is H;

each $R^3$ is independently selected from the group consisting of H and fluorine; and $R^4$ is selected from the group consisting of methyl and —CHF$_2$.

In one embodiment, in each of Formulas (I), (I'), (IA), and (IA'):

ring C is:

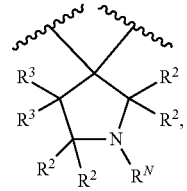

wherein each $R^N$ group is selected from the group consisting of H, —C(O)CH$_3$, —C(O)CH$_2$CH$_3$, —C(O)CH$_2$CH(CH$_3$)$_2$, —C(O)-cyclopropyl, —C(O)—CH$_2$-cyclopropyl, —C(O)N(CH$_3$)$_2$, —C(O)NHCH$_3$, —S(O)$_2$CH$_3$, —S(O)$_2$CH$_2$CH$_3$, —S(O)$_2$CH$_2$CF$_3$, —S(O)$_2$CH$_2$CH(CH$_3$)$_2$, —S(O)$_2$-phenyl, —S(O)$_2$CH$_2$-pyridyl, —S(O)$_2$-cyclopentyl, —S(O)$_2$-cyclopropyl, —S(O)$_2$-imidazolyl, —S(O)$_2$—CH$_2$-tetrahydrofuranyl, —S(O)$_2$-pyrazolyl, —S(O)$_2$N(CH$_3$)$_2$, —S(O)$_2$NHCH$_3$, methyl, ethyl, propyl, cyclopropyl, butyl, —CH$_2$-cyclopropyl, benzyl, —CH$_2$OCH$_3$, —CH$_2$OCH$_2$CH$_3$, phenyl, pyridyl, pyrimidinyl, pyrazinyl, oxadiazolyl, isoxazolyl, oxazolyl, and pyrrolyl, —CH$_2$-thiazolyl, —CH$_2$-oxazoyl, —CH$_2$-pyridyl, —CH$_2$-pyrimidinyl, —CH$_2$-pyrazinyl, —CH$_2$-pyrazolyl, —CH$_2$-cyclobutyl, —CH$_2$-cyclopropyl, and —CH$_2$-tetrahydrofuranyl, wherein said benzyl, cyclobutyl, phenyl, pyridyl, oxadiazolyl, imidazolyl, isoxazolyl, oxazolyl, and pyrrolyl are each optionally unsubstituted or substituted with fluorine, chlorine, methyl, —CN, —CF$_3$, CHF$_2$, and —OMe;

$R^1$ is methyl;

each $R^2$ is H;

each $R^3$ is independently selected from the group consisting of H and fluorine; and $R^4$ is selected from the group consisting of methyl and —CHF$_2$.

The following alternative embodiments relating to ring A and its optional substituents are applicable to any of the embodiments described hereinabove.

In one embodiment, in each of Formulas (I), (I'), (IA), and (IA'):

ring A is selected from the group consisting of phenyl, pyridazinyl, pyridyl, pyrimidinyl, pyrazinyl, triazinyl, and tetrazinyl.

In one embodiment, in each of Formulas (I), (I'), (IA), and (IA'):

ring A is selected from the group consisting of phenyl, pyridazinyl, pyridyl, pyrimidinyl, and pyrazinyl.

In one embodiment, in each of Formulas (I), (I'), (IA), and (IA'):

ring A is selected from the group consisting of phenyl and pyridyl.

In one embodiment, in each of Formulas (I), (I'), (IA), and (IA'):

each $R^A$ (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —O—CH$_2$-cyclopropyl, —CH$_2$OCH$_3$, —S(CH$_3$), methyl, ethyl, cyclopropyl, —CH$_2$-cyclopropyl, —CF$_3$, —CHF$_2$, —CH$_2$F, —OCF$_3$, and —OCHF$_2$.

In one embodiment, in each of Formulas (I), (I'), (IA), and (IA'):

each $R^A$ (when present) is independently selected from the group consisting of fluoro, chloro, bromo, —CN, —OCH$_3$, —CH$_2$OCH$_3$, methyl, cyclopropyl, —CF$_3$, —CHF$_2$, —CH$_2$F, —OCF$_3$, and —OCHF$_2$.

In one embodiment, in each of Formulas (I), (I'), (IA), and (IA'):

each $R^A$ (when present) is independently selected from the group consisting of fluoro, chloro, —CN, —OCH$_3$, —CH$_2$OCH$_3$, methyl, cyclopropyl, —CF$_3$, —CHF$_2$, and —CH$_2$F.

In one embodiment, in each of Formulas (I), (I'), (IA), and (IA'):

ring A is selected from the group consisting of phenyl, pyridazinyl, pyridyl, pyrimidinyl, pyrazinyl, triazinyl, and tetrazinyl;

m is 0, 1, or 2; and each $R^A$ (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —O—CH$_2$-cyclopropyl, —CH$_2$OCH$_3$, —S(CH$_3$), methyl, ethyl, cyclopropyl, —CH$_2$-cyclopropyl, —CF$_3$, —CHF$_2$, —CH$_2$F, —OCF$_3$, and —OCHF$_2$.

In one embodiment, in each of Formulas (I), (I'), (IA), and (IA'):

ring A is selected from the group consisting of phenyl, wherein m is 0, 1, 2, or 3, and pyridyl wherein m is 0, 1, or 2; and each $R^A$ (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —O—CH$_2$-cyclopropyl, —CH$_2$OCH$_3$, —S(CH$_3$), methyl, ethyl, cyclopropyl, —CH$_2$-cyclopropyl, —CF$_3$, —CHF$_2$, —CH$_2$F, —OCF$_3$, and —OCHF$_2$.

In one embodiment, in each of Formulas (I), (I'), (IA), and (IA'):

ring A is phenyl, wherein m is 0 or 1 and $R^A$ (when present) is fluoro;

each $R^A$ (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —O—CH$_2$-cyclopropyl, —CH$_2$OCH$_3$, —S(CH$_3$), methyl, ethyl, cyclopropyl, —CH$_2$-cyclopropyl, —CF$_3$, —CHF$_2$, —CH$_2$F, —OCF$_3$, and —OCHF$_2$.

It shall be understood that the phrase "m is 0 or more" means m is an integer from 0 up to the number that corresponds to the maximum number of substitutable hydrogen atoms of the ring to which $R^A$ is shown attached.

Thus, in embodiments wherein ring A is a moiety having 4 substitutable hydrogen atoms, m is 0, 1, 2, 3, or 4. In an alternative of such embodiments wherein ring A is a moiety having 4 substitutable hydrogen atoms, m is 0, 1, 2, or 3. In an alternative of such embodiments wherein ring A is a moiety having 4 substitutable hydrogen atoms, m is 0, 1, or 2. In an alternative of such embodiments wherein ring A is a moiety having 3 substitutable hydrogen atoms, m is 0 or 1. In alternative of such embodiments wherein ring A is a moiety having 3 substitutable hydrogen atoms, m is 0.

In embodiments wherein ring A is a moiety having 3 substitutable hydrogen atoms, m is 0, 1, 2, or 3. In an alternative of such embodiments wherein ring A is a moiety having 3 substitutable hydrogen atoms, m is 0, 1, or 2. In an alternative of such embodiments wherein ring A is a moiety having 3 substitutable hydrogen atoms, m is 0 or 1. In alternative of such embodiments wherein ring A is a moiety having 3 substitutable hydrogen atoms, m is 0.

In embodiments wherein ring A is a moiety having 2 substitutable hydrogen atoms, m is 0, 1, or 2. In an alternative of such embodiments wherein ring A is a moiety having 2 substitutable hydrogen atoms, m is 0 or 1. In alternative of such embodiments wherein ring A is a moiety having 2 substitutable hydrogen atoms, m is 0.

In embodiments wherein ring A is a moiety having 1 substitutable hydrogen atom, m is 0 or 1. In an alternative of such embodiments wherein ring A is a moiety having 1 substitutable hydrogen atoms, m is 0.

The following alternatives of $R^L$ are applicable to any of the embodiments described hereinabove.

In one embodiment, in each of Formulas (I), (I'), (IA), and (IA'):

$R^L$ is selected from the group consisting of lower alkyl and lower heteroalkyl, wherein said lower alkyl and lower heteroalkyl of $R^L$ are each optionally unsubstituted or substituted with one or more halogen.

In one embodiment, in each of Formulas (I), (I'), (IA), and (IA'):

$R^L$ is selected from the group consisting of methyl, ethyl, propyl, butyl, —CF$_3$, —CHF$_2$, —CH$_2$F, —CH$_2$CF$_3$, —CF$_2$CH$_3$, —CH$_2$OCH$_3$, —CH$_2$OCH$_2$CH$_3$, —CH$_2$CH$_2$OCH$_3$, —CH$_2$SCH$_3$, —CH$_2$SCH$_2$CH$_3$, —CH$_2$CH$_2$SCH$_3$, —CH$_2$N(CH$_3$)$_2$, —CH$_2$NHCH$_3$, —CH$_2$CH$_2$N(CH$_3$)$_2$, —CH$_2$OCF$_3$, and —CH$_2$OCHF$_2$.

In one embodiment, in each of Formulas (I), (I'), (IA), and (IA'): R$^L$ is selected from the group consisting of methyl, ethyl, —CF$_3$, —CHF$_2$, —CH$_2$F, —CH$_2$CF$_3$, —CF$_2$CH$_3$, —CH$_2$OCH$_3$, —CH$_2$OCH$_2$CH$_3$, —CH$_2$SCH$_3$, —CH$_2$N(CH$_3$)$_2$, —CH$_2$OCF$_3$, and —CH$_2$OCHF$_2$.

In one embodiment, in each of Formulas (I), (I'), (IA), and (IA'): R$^L$ is selected from the group consisting of methyl, ethyl, —CF$_3$, —CHF$_2$, —CH$_2$F, —CH$_2$CF$_3$, —CF$_2$CH$_3$, —CH$_2$OCH$_3$, CH$_2$OCF$_3$, and —CH$_2$OCHF$_2$.

In one embodiment, in each of Formulas (I), (I'), (IA), and (IA'):

R$^L$ is a moiety having the formula

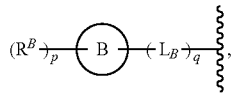

wherein q, L$_B$, ring B, p, and R$^B$ are each as defined in Formula (I).

In some embodiments, in each of Formulas (I), (I'), (IA), and (IA'):

q is 0. In such embodiments, -L$_B$- is absent; R$^L$ is a moiety having the formula

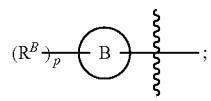

and ring B and -L$_1$- are directly connected as shown:

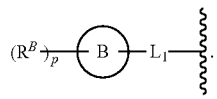

In some embodiments in each of Formulas (I), (I'), (IA), and (IA'):

q is 1; and
R$^L$ is a moiety having the formula

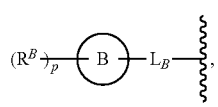

wherein:

-L$_B$- is a divalent moiety selected from the group consisting of —CH$_2$—, —CF$_2$—, —CH$_2$CH$_2$—, —OCH$_2$—, and —OCF$_2$—.

In some embodiments in each of Formulas (I), (I'), (IA), and (IA'):

q is 1; and
R$^L$ is a moiety having the formula

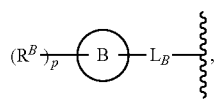

wherein:

-L$_B$- is a divalent moiety selected from the group consisting of —CH$_2$—, —CF$_2$—, and —CH$_2$CH$_2$—.

In some embodiments in each of Formulas (I), (I'), (IA), and (IA'):

q is 1; and
R$^L$ is a moiety having the formula

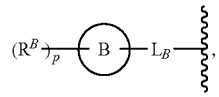

wherein:

-L$_B$- is —CH$_2$—.

In one embodiment, in each of Formulas (I), (I'), (IA), and (IA'):

R$^L$ is a moiety having the formula

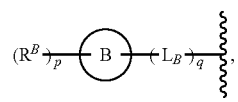

wherein:

ring B is selected from the group consisting of azetidinyl, benzimidazolyl, benzoisothiazolyl, benzoisoxazoyl, benzothiazolyl, benzoxazoyl, cyclobutyl, cyclohexyl, cyclopentyl, cyclopropyl, dihydroindenyl, dihydrooxazolyl, furanyl, imidazolyl, imidazopyridinyl, imidazopyrimidinyl, indenyl, indolyl, isothiazolyl, isoxazolyl, morpholinyl, oxadiazolyl, oxazolyl, oxetanyl, phenyl, piperazinyl, piperidinyl, pyrazinyl, pyrazolyl, pyrazolopyridinyl, pyrazolopyrimidinyl, pyridazinyl, pyridyl, pyrimidinyl, pyrazolopyridinyl, pyrrolidinyl, pyrrolyl, pyrrolopyridinyl, pyrrolopyrimidinyl, tetrahydrofuranyl, tetrahydropyranyl, tetrazolyl, thiadiazolyl, thiazolyl, thienyl, thienylpyridine, thiomorpholinyl, thiomorpholinyl dioxide, and triazolyl.

In one embodiment, in each of Formulas (I), (I'), (IA), and (IA'):

R$^L$ is a moiety having the formula

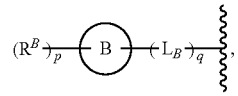

wherein:

ring B is selected from the group consisting of cyclobutyl, cyclopropyl, furanyl, indolyl, isothiazolyl, isoxazolyl, oxadiazolyl, oxazolyl, oxetanyl, phenyl, pyrazinyl, pyrazolyl, pyridazinyl, pyridyl, pyrimidinyl, pyrrolyl, tetrahydrofuranyl, tetrahydropyranyl, thiadiazolyl, thiazolyl, and thienyl.

In one embodiment, in each of Formulas (I), (I'), (IA), and (IA'):

R$^L$ is a moiety having the formula

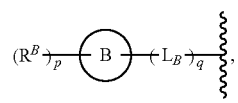

wherein:
ring B is selected from the group consisting of furanyl, indolyl, isothiazolyl, isoxazolyl, oxadiazolyl, oxazolyl, phenyl, pyrazinyl, pyrazolyl, pyridazinyl, pyridyl, pyrimidinyl, pyrrolyl, thiadiazolyl, thiazolyl, and thienyl.

In one embodiment, in each of Formulas (I), (I'), (IA), and (IA'):
$R^L$ is a moiety having the formula

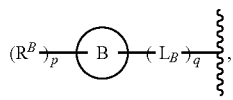

wherein:
ring B is selected from the group consisting of isoxazoyl, oxadiazoyl, oxazoyl, phenyl, pyridinyl, pyrazinyl, pyrimidinyl, and pyrazolyl.

In one embodiment, in each of Formulas (I), (I'), (IA), and (IA'):
$R^L$ is a moiety having the formula

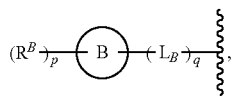

wherein:
each $R^B$ group (when present) is independently selected from the group consisting of halogen, oxo, —OH, —CN, —SF$_5$, —NH$_2$, —NH(CH$_3$), —N(CH$_3$)$_2$, —NHC(O)CH$_3$, —N(CH$_3$)C(O)CH$_3$, —NHS(O)$_2$CH$_3$, —N(CH$_3$)S(O)$_2$CH$_3$, —C(O)OCH$_3$, —C(O)OCH$_2$CH$_3$, —C(O)N(CH$_3$)$_2$, —C(O)NHCH$_3$, —S(O)$_2$CH$_3$, —S(O)$_2$N(CH$_3$)$_2$, —S(O)$_2$NHCH$_3$, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, —S(CH$_3$), methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridyl, oxadiazoyl, isoxazoyl, oxazoyl, and pyrrolyl,
wherein each said phenyl, pyridyl, oxadiazoyl, isoxazoyl, oxazoyl, and pyrrolyl is optionally substituted with from 1 to 3 substituents independently selected from the group consisting of F, Cl, —CN, —CH$_3$, —OCH$_3$, and —CF$_3$.

In one embodiment, in each of Formulas (I), (I'), (IA), and (IA'):
$R^L$ is a moiety having the formula

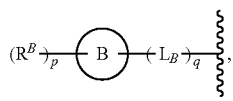

wherein:
each $R^B$ group (when present) is independently selected from the group consisting of fluoro, chloro, bromo, —OH, —CN, —SF$_5$, —NH$_2$, —NH(CH$_3$), —N(CH$_3$)$_2$, —NHC(O)CH$_3$, —N(CH$_3$)C(O)CH$_3$, —NHS(O)$_2$CH$_3$, —N(CH$_3$)S(O)$_2$CH$_3$, —C(O)OCH$_3$, —C(O)OCH$_2$CH$_3$, —C(O)N(CH$_3$)$_2$, —C(O)NHCH$_3$, —S(O)$_2$CH$_3$, —S(O)$_2$N(CH$_3$)$_2$, —S(O)$_2$NHCH$_3$, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, —S(CH$_3$), methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, and —OCH$_2$CH$_2$F.

In one embodiment, in each of Formulas (I), (I'), (IA), and (IA'):
$R^L$ is a moiety having the formula

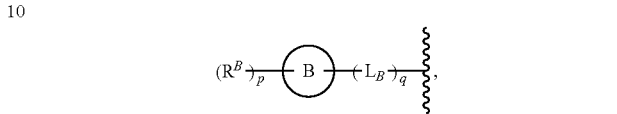

wherein:
each $R^B$ group (when present) is independently selected from the group consisting of fluoro, chloro, bromo, —CN, —S(O)$_2$CH$_3$, —OCH$_3$, —O-cyclopropyl, —O—CH$_2$-cyclopropyl, —OCH$_2$—C≡C—H, —OCH$_2$—C≡C—CH$_3$, methyl, cyclopropyl, —CH$_2$-cyclopropyl, —CH$_2$OCH$_3$, —C≡CH, —C≡C—CH$_3$, —CF$_3$, —CHF$_2$, —CH$_2$F, —OCF$_3$, —OCHF$_2$, —OCH$_2$F, and —OCH$_2$CH$_2$F.

In one embodiment, in each of Formulas (I), (I'), (IA), and (IA'):
$R^L$ is a moiety having the formula

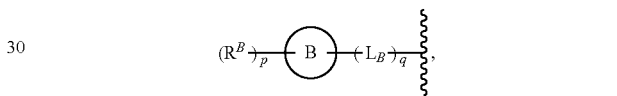

wherein:
q is 0 or 1;
-$L_B$- (when present) is a divalent moiety selected from the group consisting of —CH$_2$—, —CF$_2$—, —CH$_2$CH$_2$—, —OCH$_2$—, and —OCF$_2$—;
ring B is selected from the group consisting of azetidinyl, benzimidazolyl, benzoisothiazolyl, benzoisoxazoyl, benzothiazolyl, benzoxazoyl, cyclobutyl, cyclohexyl, cyclopentyl, cyclopropyl, dihydroindenyl, dihydrooxazolyl, furanyl, imidazolyl, imidazopyridinyl, imidazopyrimidinyl, indenyl, indolyl, isothiazolyl, isoxazolyl, morpholinyl, oxadiazolyl, oxazolyl, oxetanyl, phenyl, piperazinyl, piperidinyl, pyrazinyl, pyrazolyl, pyrazolopyridinyl, pyrazolopyrimidinyl, pyridazinyl, pyridyl, pyrimidinyl, pyrazolopyridinyl, pyrrolidinyl, pyrrolyl, pyrrolopyridinyl, pyrrolopyrimidinyl, tetrahydrofuranyl, tetrahydropyranyl, tetrazolyl, thiadiazolyl, thiazolyl, thienyl, thienylpyridine, thiomorpholinyl, thiomorpholinyl dioxide, and triazolyl;
p is 0 or more; and
each $R^B$ group (when present) is independently selected from the group consisting of halogen, oxo, —OH, —CN, —SF$_5$, —NH$_2$, —NH(CH$_3$), —N(CH$_3$)$_2$, —NHC(O)CH$_3$, —N(CH$_3$)C(O)CH$_3$, —NHS(O)$_2$CH$_3$, —N(CH$_3$)S(O)$_2$CH$_3$, —C(O)OCH$_3$, —C(O)OCH$_2$CH$_3$, —C(O)N(CH$_3$)$_2$, —C(O)NHCH$_3$, —S(O)$_2$CH$_3$, —S(O)$_2$N(CH$_3$)$_2$, —S(O)$_2$NHCH$_3$, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, —S(CH$_3$), methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridyl, oxadiazoyl, isoxazoyl, oxazoyl, and pyrrolyl,
wherein each said phenyl, pyridyl, oxadiazoyl, isoxazoyl, oxazoyl, and pyrrolyl is optionally substituted with from 1 to 3 substituents independently selected from the group consisting of F, Cl, CN, —CH$_3$, —OCH$_3$, and —CF$_3$.

In an alternative of the immediately preceding embodiment, q is 0.

In another alternative of the immediately preceding embodiment, q is 1; and

-L$_B$- is a divalent moiety selected from the group consisting of —CH$_2$—, —CF$_2$—, and —CH$_2$CH$_2$—.

In another alternative of the immediately preceding embodiment, q is 1; and

-L$_B$- is —CH$_2$—.

In one embodiment, in each of Formulas (I), (I'), (IA), and (IA'):

R$^L$ is a moiety having the formula

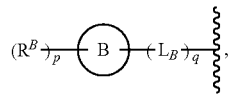

wherein:

q is 0 or 1;

-L$_B$- (when present) is a divalent moiety selected from the group consisting of —CH$_2$—, —CF$_2$—, —CH$_2$CH$_2$—, —OCH$_2$—, and —OCF$_2$—;

ring B is selected from the group consisting of cyclobutyl, cyclopropyl, furanyl, indolyl, isothiazolyl, isoxazolyl, oxadiazolyl, oxazolyl, oxetanyl, phenyl, pyrazinyl, pyrazolyl, pyridazinyl, pyridyl, pyrimidinyl, pyrrolyl, tetrahydrofuranyl, tetrahydropyranyl, thiadiazolyl, thiazolyl, and thienyl;

p is 0 or more; and each R$^B$ group (when present) is independently selected from the group consisting of fluoro, chloro, bromo, —OH, —CN, —SF$_5$, —NH$_2$, —NH(CH$_3$), —N(CH$_3$)$_2$, —NHC(O)CH$_3$, —N(CH$_3$)C(O)CH$_3$, —NHS(O)$_2$CH$_3$, —N(CH$_3$)S(O)$_2$CH$_3$, —C(O)OCH$_3$, —C(O)OCH$_2$CH$_3$, —C(O)N(CH$_3$)$_2$, —C(O)NHCH$_3$, —S(O)$_2$CH$_3$, —S(O)$_2$N(CH$_3$)$_2$, —S(O)$_2$NHCH$_3$, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, —S(CH$_3$), methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, and —OCH$_2$CH$_2$F.

In an alternative of the immediately preceding embodiment, q is 0.

In another alternative of the immediately preceding embodiment, q is 1; and

-L$_B$- is a divalent moiety selected from the group consisting of —CH$_2$—, —CF$_2$—, and —CH$_2$CH$_2$—.

In another alternative of the immediately preceding embodiment, q is 1; and

-L$_B$- is —CH$_2$—.

In one embodiment, in each of Formulas (I), (I'), (IA), and (IA'):

q is 1; and R$^L$ is a moiety having the formula

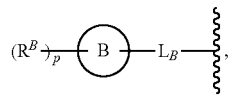

wherein:

-L$_B$- (when present) is a divalent moiety selected from the group consisting of —CH$_2$—, —CF$_2$—, —CH$_2$CH$_2$—, —OCH$_2$—, and —OCF$_2$—.

ring B is selected from the group consisting of isoxazoyl, oxadiazoyl, oxazolyl, phenyl, pyridinyl, pyrazinyl, pyrimidinyl, and pyrazolyl;

p is 0 or more; and each R$^B$ group (when present) is independently selected from the group consisting of fluoro, chloro, bromo, —CN, —S(O)$_2$CH$_3$, —OCH$_3$, —O-cyclopropyl, —O—CH$_2$-cyclopropyl, —OCH$_2$—C≡C—H, —OCH$_2$—C≡C—CH$_3$, methyl, cyclopropyl, —CH$_2$-cyclopropyl, —CH$_2$OCH$_3$, —C≡CH, —C≡C—CH$_3$, —CF$_3$, —CHF$_2$, —CH$_2$F, —OCF$_3$, —OCHF$_2$, —OCH$_2$F, and —OCH$_2$CH$_2$F.

In an alternative of the immediately preceding embodiment, -L$_B$- is a divalent moiety selected from the group consisting of —CH$_2$—, —CF$_2$—, and —CH$_2$CH$_2$—.

In another alternative of the immediately preceding embodiment, -L$_B$- is —CH$_2$—.

In one embodiment, in each of Formulas (I), (I'), (IA), and (IA'):

q is 0; and R$^L$ is a moiety having the formula

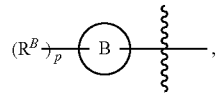

wherein:

ring B is selected from the group consisting of isoxazoyl, oxadiazoyl, oxazolyl, phenyl, pyridinyl, pyrazinyl, pyrimidinyl, and pyrazolyl;

p is 0 or more; and each R$^B$ group (when present) is independently selected from the group consisting of fluoro, chloro, bromo, —CN, —S(O)$_2$CH$_3$, —OCH$_3$, —O-cyclopropyl, —O—CH$_2$-cyclopropyl, —OCH$_2$—C≡C—H, —OCH$_2$—C≡C—CH$_3$, methyl, cyclopropyl, —CH$_2$-cyclopropyl, —CH$_2$OCH$_3$, —C≡CH, —C≡C—CH$_3$, —CF$_3$, —CHF$_2$, —CH$_2$F, —OCF$_3$, —OCHF$_2$, —OCH$_2$F, and —OCH$_2$CH$_2$F.

In one embodiment, in each of Formulas (I), (I'), (IA), and (IA'):

q is 0; and R$^L$ is a moiety having the formula

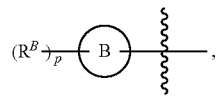

wherein:

ring B is selected from the group consisting of pyridyl and pyrazinyl;

p is 0 or 1; and each R$^B$ group (when present) is independently selected from the group consisting of fluoro, chloro, bromo, —CN, —S(O)$_2$CH$_3$, —OCH$_3$, —O-cyclopropyl, —O—CH$_2$-cyclopropyl, —OCH$_2$—C≡C—H, —OCH$_2$—C≡C—CH$_3$, methyl, cyclopropyl, —CH$_2$-cyclopropyl, —CH$_2$OCH$_3$, —C≡CH, —C≡C—CH$_3$, —CF$_3$, —CHF$_2$, —CH$_2$F, —OCF$_3$, —OCHF$_2$, —OCH$_2$F, and —OCH$_2$CH$_2$F.

It shall be understood that the phrase "p is 0 or more" means p is an integer from 0 up to the number that corresponds to the maximum number of substitutable hydrogen atoms of the ring to which R$^B$ is shown attached.

Thus, in embodiments wherein ring B is a moiety having 4 substitutable hydrogen atoms, p is 0, 1, 2, 3, or 4. In an alternative of such embodiments wherein ring B is a moiety having 4 substitutable hydrogen atoms, p is 0, 1, 2, or 3. In an alternative of such embodiments wherein ring B is a moiety having 4 substitutable hydrogen atoms, p is 0, 1, or 2. In an alternative of such embodiments wherein ring B is a moiety having 3 substitutable hydrogen atoms, p is 0 or 1. In alternative of such embodiments wherein ring B is a moiety having 3 substitutable hydrogen atoms, p is 0.

In embodiments wherein ring B is a moiety having 3 substitutable hydrogen atoms, p is 0, 1, 2, or 3. In an alternative of such embodiments wherein ring B is a moiety having 3 substitutable hydrogen atoms, p is 0, 1, or 2. In an alternative of such embodiments wherein ring B is a moiety having 3 substitutable hydrogen atoms, p is 0 or 1. In alternative of such embodiments wherein ring B is a moiety having 3 substitutable hydrogen atoms, p is 0.

In embodiments wherein ring B is a moiety having 2 substitutable hydrogen atoms, p is 0, 1, or 2. In an alternative of such embodiments wherein ring B is a moiety having 2 substitutable hydrogen atoms, p is 0 or 1. In alternative of such embodiments wherein ring B is a moiety having 2 substitutable hydrogen atoms, p is 0.

In embodiments wherein ring B is a moiety having 1 substitutable hydrogen atom, p is 0 or 1. In an alternative of such embodiments wherein ring B is a moiety having 1 substitutable hydrogen atoms, p is 0.

In an alternative of each of the embodiments described above, -$L_1$- is —C(O)NH—.

As noted above, -$L_1$- (and -$L_B$- when present) represent divalent moieties. The orientation of such divalent moieties in the formula is the same as the orientation of the moiety as written. Thus, for example, when $R^L$ is the moiety

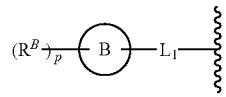

and -$L_1$- is a —C(O)NH— group, the moiety

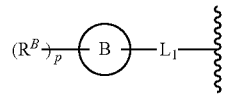

has the formula:

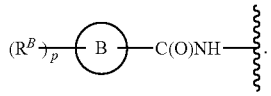

Specific non-limiting examples of compounds of the invention are shown in the table of examples below. While only one tautomeric form of each compound is shown in the tables, it shall be understood that all tautomeric forms of the compounds are contemplated as being within the scope of the non-limiting examples.

In another embodiment, 1 to 3 carbon atoms of the compounds of the invention may be replaced with 1 to 3 silicon atoms so long as all valency requirements are satisfied.

In another embodiment, there is provided a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents which may be useful in combination with the compounds of the invention include those selected from the group consisting of: (a) drugs that may be useful for the treatment of Alzheimer's disease and/or drugs that may be useful for treating one or more symptoms of Alzheimer's disease, (b) drugs that may be useful for inhibiting the synthesis Aβ, (c) drugs that may be useful for treating neurodegenerative diseases, and (d) drugs that may be useful for the treatment of type II diabetes and/or one or more symptoms or associated pathologies thereof.

Non-limiting examples of additional therapeutic agents which may be useful in combination with the compounds of the invention include drugs that may be useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from β$_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Non-limiting examples of additional therapeutic agents for that may be useful in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), galantamine (Razadyne®), and rivastigmine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer).

Another embodiment provides a method of preparing a pharmaceutical composition comprising the step of admixing at least one compound of the invention or pharmaceutically acceptable salt thereof, and a pharmaceutically acceptable carrier or diluent.

Another embodiment provides a method of inhibiting β-secretase comprising exposing a population of cells expressing β-secretase to at least one compound of the invention, or a tautomer thereof, in an amount effective to inhibit β-secretase. In one such embodiment, said population of cells is in vivo. In another such embodiment, said population of cells is ex vivo. In another such embodiment, said population of cells is in vitro.

Additional embodiments in which the compounds of the invention may be useful include: a method of inhibiting β-secretase in a patient in need thereof. A method of inhibiting the formation of Aβ from APP in a patient in need thereof. A method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer thereof, or pharmaceutically acceptable salt of said compound or said tautomer, in a therapeutically effective amount to inhibit said pathology or condition in said patient.

Additional embodiments in which the compounds of the invention may be useful include: a method of treating, preventing, and/or delaying the onset of one or more pathologies associated with Aβ and/or one or more symptoms of one or more pathologies associated with Aβ. Non-limiting examples of pathologies which may be associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, presenile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, said method(s) comprising administering to said patient in need thereof at least one compound of the invention, or a tautomer thereof, or pharmaceutically acceptable salt of said compound or said tautomer, in an amount effective to inhibit said pathology or pathologies.

Another embodiment in which the compounds of the invention may be useful includes a method of treating Alzheimer's disease, wherein said method comprises administering an effective (i.e., therapeutically effective) amount of one or more compounds of the invention (or a tautomer thereof, or pharmaceutically acceptable salt of said compound or said tautomer), optionally in further combination with one or more additional therapeutic agents which may be effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

Another embodiment in which the compounds of the invention may be useful includes a method of treating mild cognitive impairment ("MCI"), wherein said method comprises administering an effective (i.e., therapeutically effective) amount of one or more compounds of the invention (or a tautomer thereof, or pharmaceutically acceptable salt of said compound or said tautomer) to a patient in need of treatment. In one such embodiment, treatment is commenced prior to the onset of symptoms.

Another embodiment in which the compounds of the invention may be useful includes a method of preventing, or alternatively of delaying the onset, of mild cognitive impairment or, in a related embodiment, of preventing or alternatively of delaying the onset of Alzheimer's disease. In such embodiments, treatment can be initiated prior to the onset of symptoms, in some embodiments significantly before (e.g., from several months to several years before) the onset of symptoms to a patient at risk for developing MCI or Alzheimer's disease. Thus, such methods comprise administering, prior to the onset of symptoms or clinical or biological evidence of MCI or Alzheimer's disease (e.g., from several months to several yeards before, an effective (i.e., therapeutically effective), and over a period of time and at a frequency of dose sufficient for the therapeutically effective degree of inhibition of the BACE enzyme over the period of treatment, an amount of one or more compounds of the invention (or a tautomer thereof, or pharmaceutically acceptable salt of said compound or said tautomer) to a patient in need of treatment.

Another embodiment in which the compounds of the invention may be useful includes a method of treating Down's syndrome, comprising administering an effective (i.e., therapeutically effective) amount of one or more compounds of the invention (or a tautomer thereof, or pharmaceutically acceptable salt or solvate of said compound or said tautomer) to a patient in need of treatment.

Another embodiment in which the compounds of the invention may be useful includes a kit comprising, in separate containers, in a single package, pharmaceutical compositions for use in combination, wherein one container comprises an effective amount of a compound of the invention (or a tautomer thereof, or pharmaceutically acceptable salt of said compound or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1 and/or BACE-2.

In various embodiments, the compositions and methods disclosed above and below wherein the compound(s) of the invention is a compound or compounds selected from the group consisting of the exemplary compounds of the invention described herein.

In another embodiment, the invention provides methods of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease, said method comprising administering a compound of the invention, or a pharmaceutically acceptable salt of said compound or said tautomer, to a patient in need thereof in an amount effective to treat said disease or pathology.

In another embodiment, the invention provides for the use of any of the compounds of the invention for use as a medicament, or in medicine, or in therapy.

In another embodiment, the invention provides for use of a compound of the invention for the manufacture of a medicament for the treatment of a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease.

DEFINITIONS

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine, chlorine, bromine, or iodine. Preferred are fluorine, chlorine and bromine.

"Alkyl" means an aliphatic hydrocarbon group, which may be straight or branched, comprising 1 to about 10 carbon atoms. "Lower alkyl" means a straight or branched alkyl group comprising 1 to about 4 carbon atoms. Branched means that one or more lower alkyl groups such as methyl, ethyl or propyl, are attached to a linear alkyl chain. Non-limiting examples of suitable alkyl groups include methyl, ethyl, n-propyl, isopropyl, n-butyl, i-butyl, and t-butyl.

"Haloalkyl" means an alkyl as defined above wherein one or more hydrogen atoms on the alkyl is replaced by a halo group defined above.

"Heteroalkyl" means an alkyl moiety as defined above, which is substituted by one or more (e.g., one, two, or three) moieties independently selected from the group consisting of: —O-alkyl, —S-alkyl, —S(O)-alkyl, —S(O)$_2$-alkyl, —N(H)alkyl, and —N(alkyl)$_2$.

"Alkenyl" means an aliphatic hydrocarbon group containing at least one carbon-carbon double bond and which may be straight or branched and comprising about 2 to about 10 carbon atoms in the straight or branched chain. Branched means that one or more lower alkyl groups such as methyl, ethyl propyl, ethenyl or propenyl are attached to a linear or branched alkenyl chain. "Lower alkenyl" means about 2 to about 4 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, heterocycloalkyl, etc. indicates a divalent moiety, e.g., —CH$_2$CH$_2$— is ethylene, and

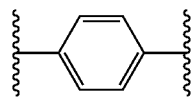

is para-phenylene.

"Alkynyl" means an aliphatic hydrocarbon group containing at least one carbon-carbon triple bond and which may be straight or branched and comprising about 2 to about 10 carbon atoms in the chain. Branched means that one or more lower alkyl groups such as methyl, ethyl or propyl, or lower alkenyl or lower alkynyl groups, are attached to a linear alkynyl chain. "Lower alkynyl" means about 2 to about 4 carbon atoms in the chain which may be straight or branched. Non-limiting examples of suitable alkynyl groups include ethynyl, propynyl, 2-butynyl and 3-methylbutynyl.

"Alkenylene" means a difunctional group obtained by removal of a hydrogen from an alkenyl group that is defined above. Non-limiting examples of alkenylene include —CH═CH—, —C(CH$_3$)═CH—, and —CH═CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thi-azolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moities include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising about 3 to about 10 carbon atoms, preferably about 3 to about 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Cycloalkenyl" means a non-aromatic mono or multicyclic ring system comprising about 3 to about 10 carbon atoms, preferably about 5 to about 10 carbon atoms which contain at least one carbon-carbon double bond. Preferred cycloalkenyl rings contain about 5 to about 7 ring atoms. The cycloalkenyl can be optionally substituted with one or more substituents, which may be the same or different, as described herein. The term "monocyclic cycloalkenyl" refers to monocyclic versions of cycloalkenyl groups described herein and includes non-aromatic 3- to 7-membered monocyclic cycloalkyl groups which contains one or more carbon-carbon double bonds. Non-limiting examples include cyclopropenyl, cyclobutenyl, cyclopentenyl, cyclohexenyl, cyclohetpenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide,"

when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

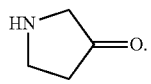

As used herein, the term "monocyclic heterocycloalkyl" refers monocyclic versions of the heterocycloalkyl moities described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

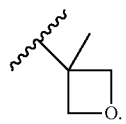

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more substituents, which may be the same or different, as described herein. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidinone (or pyrrolone):

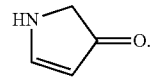

As used herein, the term "monocyclic heterocycloalkenyl" refers to monocyclic versions of the heterocycloalkenyl moities described herein and include 4- to 7-membered monocyclic heterocycloalkenyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, dihydrothiophenyl, and dihydrothiopyranyl, and oxides thereof.

It should be noted that in hetero-atom containing ring systems of this invention, there are no hydroxyl groups on carbon atoms adjacent to a N, O or S, as well as there are no N or S groups on carbon adjacent to another heteroatom.

there is no —OH attached directly to carbons marked 2 and 5.

"Arylalkyl" (or "aralkyl") means an aryl-alkyl- group in which the aryl and alkyl are as previously described, except that in this context the "alkyl" portion of the "arylalkyl" (or "-alkyl-aryl") group refers to a straight or branched lower alkyl group. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" (or as "-alkyl-aryl") to indicate the point of attachment to the parent moiety. Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. As indicated above, the "alkyl" group in this context represents a lower alkyl group, which may be straight or branched, or unsubstituted and/or substituted as described herein.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl- moiety or the like includes substitution on any ring portion and/or on the alkyl portion of the group.

When a variable appears more than once in a group, e.g., $R^6$ in $—N(R^6)_2$, or a variable appears more than once in a structure presented herein, the variables can be the same or different.

The line

———, as a bond generally indicates a mixture of, or either of, the possible isomers, e.g., containing (R)- and (S)-stereochemistry. For example:

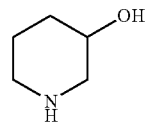

means containing both

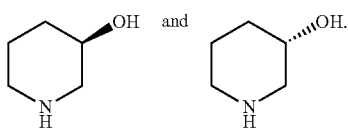

The wavy line ~~~, as used herein, indicates a point of attachment to the rest of the compound. Lines drawn into the ring systems, such as, for example:

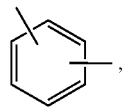

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

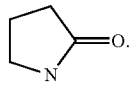

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

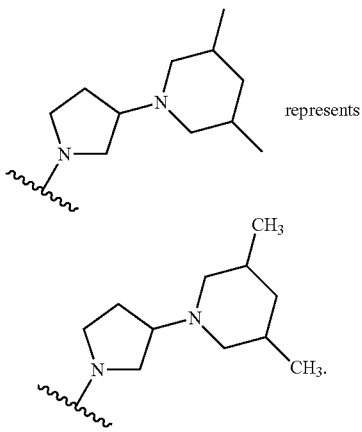

represents

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^{1}H$) and deuterium ($^{2}H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation comparing one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

Compounds of the invention can be made using procedures known in the art. The following reaction schemes show typical procedures, but those skilled in the art will recognize that other procedures can also be suitable. Reactions may involve monitoring for consumption of starting material, and there are many methods for such monitoring, including but not limited to thin layer chromatography (TLC) and liquid chromatography mass spectrometry (LCMS), and those skilled in the art will recognize that where one method is specified, other non-limiting methods may be substituted.

Techniques, solvents and reagents may be referred to by their abbreviations as follows:

Acetic acid: AcOH
Acetic anhydride: Ac$_2$O
Acetonitrile: MeCN
Aqueous: aq.
Benzyl: Bn
tert-Butyl: t-Bu or tBu
Centimeters: cm
3-Chloroperoxybenzoic acid: mCPBA
Di-tert-butyldicarbonate: Boc$_2$O
Dichloromethane: DCM
Diisopropylamine: iPr$_2$NH or DIPA
Diisopropylethylamine: DIEA or iPr$_2$NEt
Dimethylformamide: DMF
Dimethylsulfoxide: DMSO
Diphenylphosphoryl azide: DPPA
Ether or diethyl ether: Et$_2$O
Ethyl: Et
Ethyl acetate: AcOEt, EtOAc, or EA
Example: Ex.
Grams: g
O-(7-azabenzotriazol-1-yl)-N,N,N',N'-tetramethyluronium hexafluorophosphate: HATU
Hexanes: hex
High performance liquid chromatography: HPLC
Hydroxybenzotriazole: HOBt
Inhibition: Inh.
Liquid chromatography mass
Liter: L
Lithium bis(trimethylsilyl)amide: LiHMDS
Spectrometry: LCMS
Mass/charge ratio: m/z
Methanesulfonyl chloride: MeSO$_2$Cl or MsCl
Methanol: MeOH
Methyl t-butyl ether: MTBE
Methyl iodide: MeI
Methyl magnesium bromide: MeMgBr Microliters: μl or μL
Micrometer: μm
Milligrams: mg
Milliliters: mL
Millimeter: mm
Millimoles: mmol
Micromoles: μM or uM
Minutes: min
n-Butyllithium: nBuLi or n-BuLi
Nuclear magnetic resonance spectroscopy: NMR
Number: no. or No.
Para-methoxy benzyl: PMB
Petroleum ether: PE
Phenyl: Ph
Retention time: $t_R$ or Ret. Time
Reverse Phase: RP
Room temperature (ambient, about 25° C.): rt or RT
tert-Butoxycarbonyl: t-Boc or Boc
Trifluoroacetic acid: TFA
Supercritical Fluid Chromatography: SFC
Temperature: temp.
Tetrahydrofuran: THF
Triethylamine: $Et_3N$ or TEA
2,4,6-tripropyl-1,3,5,2,4,6-
trioxatriphosphorinane-2,4-6-trioxide: T3P
Volume: v Method A

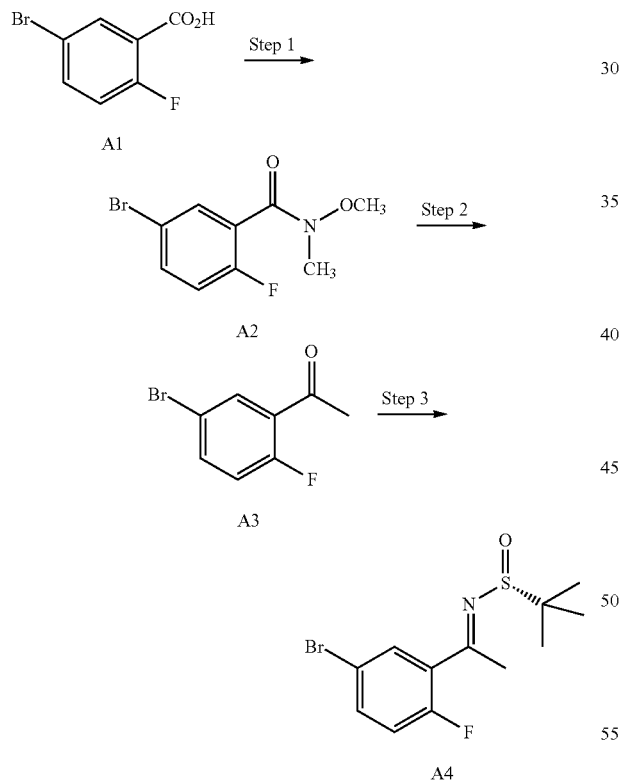

Step 1:
To a suspension of compound A1 (150 g, 0.68 mol) in $CH_2Cl_2$ (2200 mL) at 0° C. were added oxalyl chloride (130 g, 1.03 mol) and DMF (1 mL). The mixture was stirred at 0° C. for 3 h and then concentrated in vacuo. The residue was dissolved in $CH_2Cl_2$ (2200 mL) and the resultant solution was cooled to 0° C. To the solution was added N,O-dimethylhydroxylamine hydrochloride (87 g, 0.89 mol) followed by dropwise addition of $Et_3N$ (346 g, 3.42 mol). The mixture was warmed to RT and stirred overnight. The mixture was then poured into a separatory funnel that contained 1 N $HCl_{(aq.)}$ (2000 mL). The layers were separated and the organic layer was washed with 1N aq. NaOH (300 mL), dried over $Na_2SO_4$, and concentrated to provide compound A2.

Step 2:
To a stirred solution of compound A2 (150 g, 0.57 mol) in anhydrous THF (2000 mL) at 0° C. under an atmosphere of nitrogen was added a solution of MeMgBr (3.0 M in $Et_2O$, 382 mL, 1.14 mol). The mixture was stirred at 0° C. for 2 h. After that time, the solution was poured into a cold solution of 2 N $HCl_{(aq.)}$ (2000 mL) and the mixture was allowed to warm to RT. The mixture was then extracted with ethyl acetate (1500 mL×2). The combined organic layers were washed with sat. $NaHCO_{3(aq.)}$ and brine, dried over $Na_2SO_4$, filtered and concentrated in vacuo to afford compound A3.

Step 3:
A mixture of compound A3 (145 g, 0.67 mol), (R)-(+)-2-methyl-2-propanesulfinamide (106 g, 0.87 mol) and titanium(IV) ethoxide (274 g, 1.2 mol) in THF (1500 mL) was heated to 70° C. and stirred overnight. After that time, the reaction was cooled to 5° C. and quenched with $H_2O$ (300 mL). The mixture was stirred at room temperature for 40 min and filtered. The filter cake was washed with ethyl acetate (4×2000 mL). The combined organic layers were then concentrated in vacuo. The crude residue was purified by silica gel chromatography (gradient elution 100:1 to 3:1 petroleum ether:ethyl acetate) to afford compound A4.

Method B

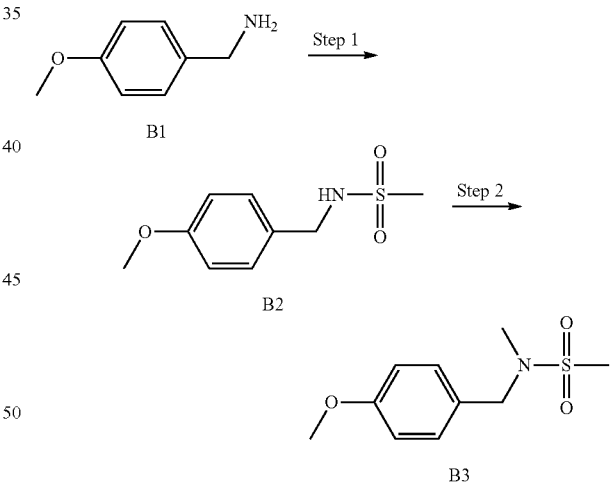

Step 1:
To a stirred solution of compound B1 (200 g, 1.46 mol) in pyridine (400 mL) at 0° C. was added MsCl (167 g, 1.46 mol) dropwise via an addition funnel. After the addition was completed, the mixture was stirred at RT for 6 h and concentrated under reduced pressure. To the residue was added $CH_2Cl_2$ (1 L). The organic solution was sequentially washed with 1N $HCl_{(aq.)}$ (1 L×2), sat. $NaHCO_{3(aq.)}$ (1 L×2), and brine (500 mL). The organic layer was dried over anhydrous $Na_2SO_4$, filtered, and concentrated to afford a crude product, which was washed with petroleum ether/ethyl acetate (2/1, 300 mL). The solid product was isolated by filtration and dried under vacuum to afford compound B2.

Step 2:

To a solution of compound B2 (220 g, 1.02 mol) in DMF (1100 mL) at 0° C. was added Cs₂CO₃ (500 g, 1.53 mol) followed by dropwise addition of CH₃I (188.6 g, 1.33 mol). The mixture was stirred at RT and then poured into cold water which caused a solid to precipitate. The solid was removed via filtration and washed with water. The solid was then dissolved in CH₂Cl₂ (3 L). The organic layer was washed with brine (500 mL), dried over anhydrous Na₂SO₄, filtered, and concentrated. The product was further dried under vacuum to afford compound B3.

Method C

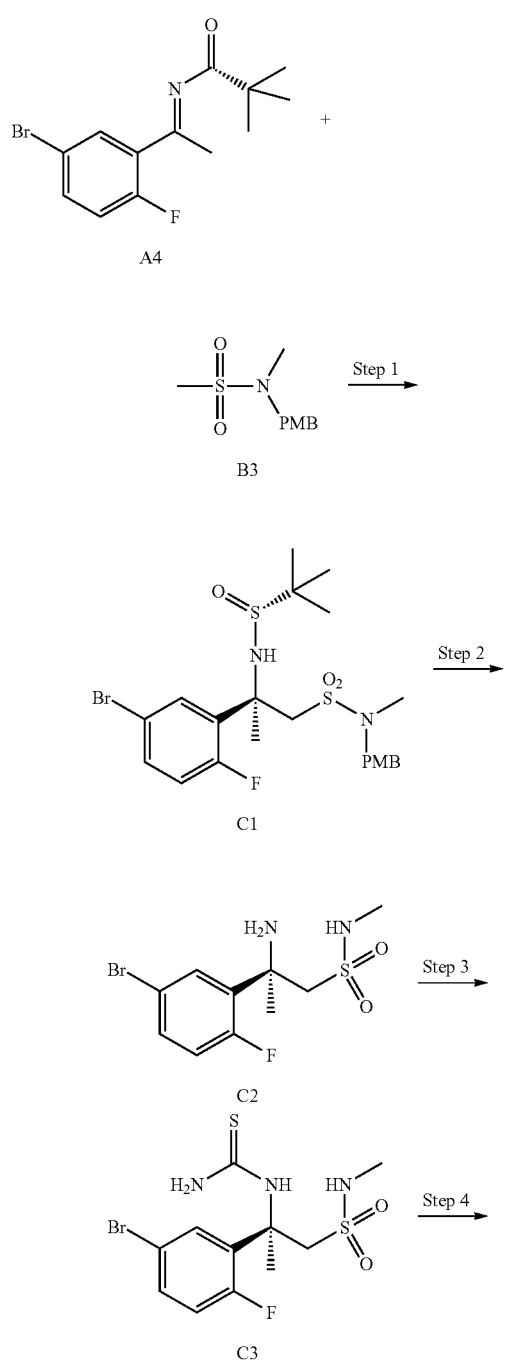

Step 1:

To a stirred solution of compound B3 (65 g, 284 mmol) in dry THF (1500 mL) at −65° C. under an atmosphere of nitrogen was added a solution of n-BuLi (2.5 M in hexanes, 125 mL, 312 mmol) dropwise. After stirring at −65° C. for 30 min, a solution of compound A4 (100 g, 312 mmol) in THF (500 mL) was added dropwise. The solution was stirred at −65° C. for 3 h and quenched with a sat. NH₄Cl$_{(aq.)}$ solution (300 mL). The resultant mixture was warmed to RT and stirred overnight. The mixture then was extracted with ethyl acetate (800 mL×4) and the combined organic extracts were concentrated. The residue was purified by column chromatography (SiO₂: gradient elution 15:1 to 3:1 petroleum ether:hexanes) to afford compound C1.

Step 2:

To a solution of compound C1 (85 g, 0.15 mol) in CH₂Cl₂/MeOH (600 mL/300 mL) at 0° C. was added a solution of HCl (4 M in ethyl acetate, 600 mL). The mixture was stirred at RT for 2 h and concentrated. The residue was dissolved in CHCl₃ (850 mL) and 1,3-dimethoxybenzene (139 g, 1.0 mol) was added. To the mixture was added TFA (529 g, 4.6 mol) and the resultant mixture was stirred at RT overnight. The mixture was then concentrated in vacuo. The residue was partitioned between water (1000 mL) and MTBE (1000 mL). The aqueous phase was separated and washed with MTBE (1000 mL×3) and then basified to pH 9 with sat. Na₂CO₃(aq.). The aqueous layer was then extracted with CH₂Cl₂ (1000 mL×4). The organic layers were combined, dried over anhydrous Na₂SO₄, filtered, and concentrated to afford compound C2.

Step 3:

To a solution of compound C2 (106 g, 326 mmol) in anhydrous CH₂Cl₂ (1000 mL) was added benzoyl isothiocyanate (69.07 g, 424 mmol) and the resultant mixture was stirred at RT overnight. The mixture was concentrated in vacuo. The residue was dissolved in methanol (500 mL) to which a solution of sodium methoxide [prepared from Na$_{(m)}$ (18.74 g) in methanol (500 mL)] was added. The mixture was stirred at RT for 3 h and concentrated in vacuo to afford a solid that was dissolved in water (800 mL). The solution was adjusted to approximately pH 9 with addition of a 1N HCl (aq.) solution. The resulting mixture was then extracted with CH₂Cl₂ (800 mL×3). The combined organic layers were washed with brine (500 mL), dried over anhydrous Na₂SO₄, filtered, and concentrated. The crude residue was purified by column chromatography (SiO₂: gradient elution 10:1 to 3:1 petroleum ether:ethyl acetate) to afford compound C3.

Step 4:

To a solution of compound C3 (57 g, 148 mmol) in ethanol (1400 mL) was added methyl iodide (26.3 g, 185 mmol). The mixture was heated to 75° C. and stirred overnight. The mixture was then cooled to RT and concentrated in vacuo. The residue was partitioned between ethyl acetate and a Na₂CO₃(aq.) solution. The mixture was extracted with ethyl acetate (500 mL×3). The combined organic layers were washed with brine, dried over Na₂SO₄, filtered, and concentrated to afford C4 which was used without further purification.

Step 5:

To a solution of compound C4 (100 g, 285 mmol) in CH₂Cl₂ (1000 mL) were added Boc₂O (74 g, 343 mmol) and Et₃N (72.2 g, 714 mmol). The mixture was stirred at RT overnight and then diluted with CH₂Cl₂ (1000 mL). The mixture was then washed with sat. NaHCO₃ (aq.), dried over anhydrous Na₂SO₄, filtered, and concentrated in vacuo. The crude residue was purified by column chromatography (SiO₂: gradient elution 50:1 to 3:1 petroleum ether:hexanes) to afford C5.

Method D

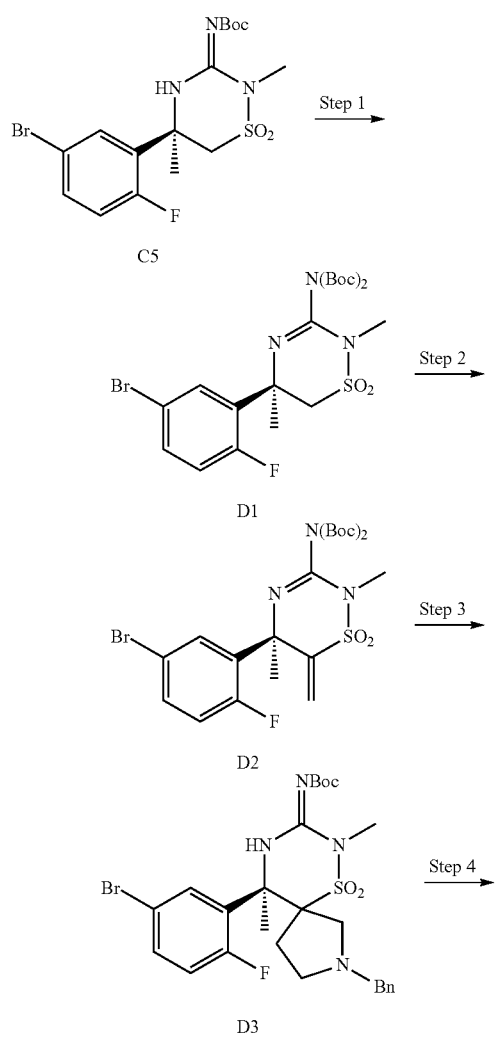

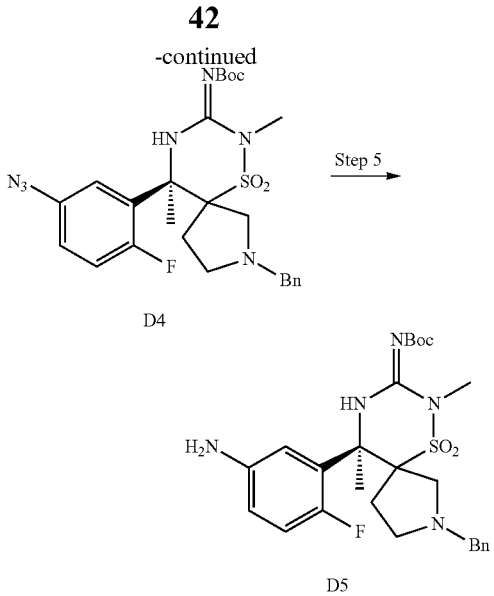

Step 1:

A mixture of C5 (10 g, 20 mmol), Boc₂O (8.7 g, 40 mmol), and DMAP (3.3 g, 30 mmol) in DCM (100 mL) was stirred at RT for 6 h, then quenched with H₂O. The mixture was extracted with DCM and the combined organic layers were washed with brine, dried over Na₂SO₄, and concentrated. The residue was purified by silica gel chromatography (petroleum ether:EtOAc 5:1) to afford D1.

Step 2:

To a solution of D1 (3.0 g, 5.5 mmol) in THF (200 mL) at −78° C. was added LiHMDS (1 M solution in THF, 22 mL, 22 mmol). The resultant mixture was then stirred at −78° C. for 1 h, whereupon 1-chloro-2-(chloromethoxy)ethane (1.4 g, 11 mmol) was added. The reaction mixture was allowed to warm to RT and stirred for an additional 16 h. The reaction mixture was quenched with a saturated solution of NH₄Cl(aq.) (10 mL) and the resultant mixture was extracted with EtOAc. The combined extracts were washed with brine, dried over Na₂SO₄, and concentrated. The residue was purified by silica gel chromatography (petroleum ether:EtOAc 5:1) to afford D2.

Step 3:

To a solution of compound D2 (400 mg, 0.7 mmol) in DCM (2 mL) at 0° C. was added N-benzyl-1-methoxy-N-((trimethylsilyl)methyl)methanamine (2.2 g, 7 mmol), followed by TFA (20 mg, 0.17 mmol) in DCM (0.3 mL). The mixture was stirred at RT for 16 h, then quenched by the addition of aq. NaHCO₃ (10 mL). The resultant mixture was extracted with DCM and the combined extracts were washed with brine, dried over Na₂SO₄, and concentrated. The residue was purified by silica gel chromatography (petroleum ether:EtOAc 4:1) to afford D3.

Step 4:

To a solution of compound D3 (180 mg, 0.3 mmol) in EtOH/H₂O (3:1, 20 mL) at 25° C. were added trans-N,N-dimethylcyclohexane-1,2-diamine (14 mg, 0.1 mmol), NaN₃ (100 mg, 0.9 mmol), L-ascorbic acid (0.66 M solution in water, 0.2 mL, 0.13 mmol), and CuSO₄·5H₂O (16.5 mg, 0.07 mmol). The mixture was stirred at 70° C. for 2 h then cooled to RT, and extracted with EtOAc. The combined extracts were washed with brine, dried over Na₂SO₄, and concentrated. The residue was purified by silica gel chromatography eluting with (PE:EtOAc 3:1) to give D4.

Step 5:

To a solution of D4 (100 mg, 0.18 mmol) in THF/H₂O (2:1, 30 mL) at 25° C. was added PPh₃ (71 mg, 0.27 mmol) and the resultant mixture was then stirred 80° C. for 16 h. The mixture was then cooled to RT and extracted with EtOAc. The combined extracts were washed with brine, dried over Na₂SO₄, and concentrated. The residue was purified by silica gel chromatography eluting with petroleum ether:EtOAc (3:1) to afford D5.

washed with brine, dried over Na₂SO₄, and concentrated. The residue was purified by silica gel chromatography (petroleum ether:EtOAc 1:1) to afford E1.

Step 2:

To a solution of E1 (100 mg, 0.17 mmol) in DCM (10 mL) at 0° C. was added TFA (1 mL). The mixture was stirred at RT for 2 h, then concentrated. The residue was purified by RP-HPLC (column 25×200 mm, 5 μm; mobile phases A=water with 0.075% v/v TFA, B=MeCN; gradient 25-55% B, 10 min, 35 mL/min) to give Example 1.

TABLE 1

| Ex. | Structure | BACE1 K$_i$ (nM) | BACE2 K$_i$ (nM) | LCMS data m/z (M + 1) | t$_R$ (min) | conditions |
|---|---|---|---|---|---|---|
| 1 | 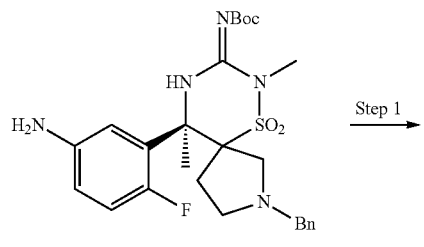 | 3.4 | 4.5 | 555 | 2.36 | 1 |

Method E

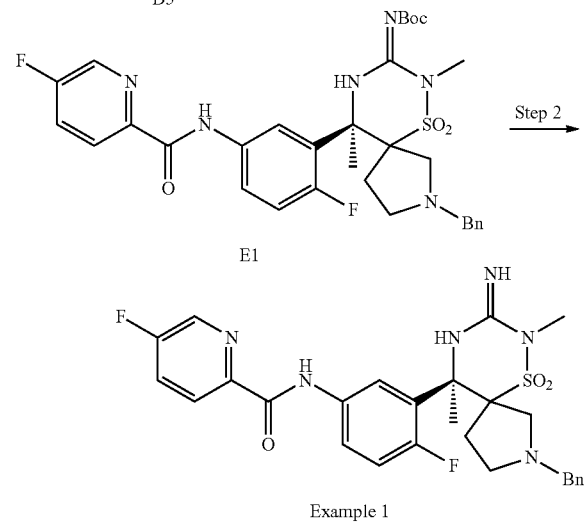

Method F

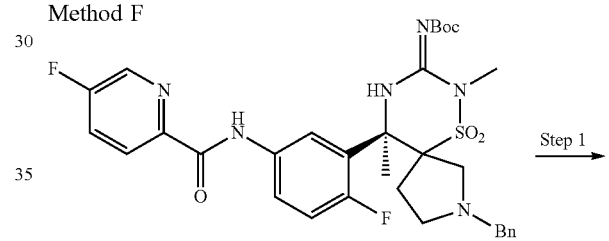

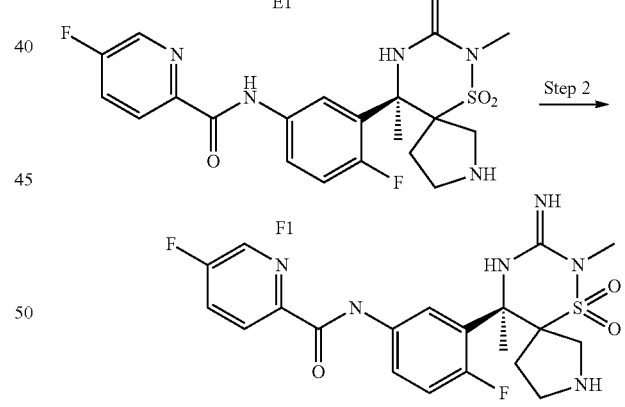

Step 1:

To a solution of D5 (100 mg, 0.19 mmol) in DMF (26 mL) at 25° C. were added 5-fluoropyridine-2-carboxylic acid (40 mg, 0.23 mmol), HATU (136 mg, 0.36 mmol), and DIEA (46 mg, 0.36 mmol). The reaction mixture was stirred at 25° C. for 16 h, whereupon it was quenched by water. The mixture was extracted with DCM and the combined extracts were Step 1:

To a solution of compound E1 (300 mg, 0.4 mmol) in MeOH (20 mL) at 25° C. was added 10% Pd/C (100 mg). The mixture was stirred at 25° C. under an atmosphere of H₂ (25 psi) for 4 h. The reaction mixture was then filtered and the filtrate was concentrated to afford compound F1.

Step 2:

To a solution of compound F1 (100 mg, 0.18 mmol) in DCM (10 mL) at 0° C. was added TFA (1 mL). The mixture was stirred at 25° C. for 2 h, concentrated, and purified by RP-HPLC (column 30×150 mm, 5 μm; mobile phases A=water with 0.075% v/v TFA, B=MeCN; gradient 15-65% B, 10 min, 25 mL/min) to give Example 2.

TABLE 2

| Ex. | Structure | BACE1 K$_i$ (nM) | BACE2 K$_i$ (nM) | LCMS data m/z (M + 1) | t$_R$ (min) | conditions |
|---|---|---|---|---|---|---|
| 2 | 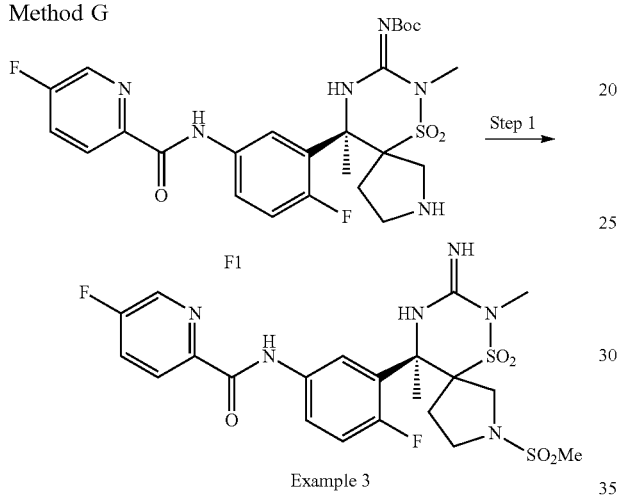 | 19.5 | 30 | 465 | 1.99 | 1 |

Method G

Step 1:
To a solution of compound F1 (140 mg, 0.21 mmol) in DCM (20 mL) at 0° C. were added Et$_3$N (42 mg, 0.88 mmol) and MeSO$_2$Cl (100 mg, 0.88 mmol). The mixture was stirred at 0° C. for 2 h, quenched with water, and then extracted with DCM. The combined extracts were washed with brine, dried over Na$_2$SO$_4$, and concentrated. The residue was dissolved in TFA/DCM (10%, 2 mL) and the resultant mixture was stirred for 2 h. The reaction mixture was concentrated and the crude residue was purified by RP-HPLC (column 30×150 mm, 5 μm; mobile phases A=water with 0.075% v/v TFA, B=MeCN; gradient elution 15-55% B, 10 min, 25 mL/min) to give Example 3.

TABLE 3

| Ex. | Structure | BACE1 K$_i$ (nM) | BACE2 K$_i$ (nM) | LCMS data m/z (M + 1) | t$_R$ (min) | conditions |
|---|---|---|---|---|---|---|
| 3 | 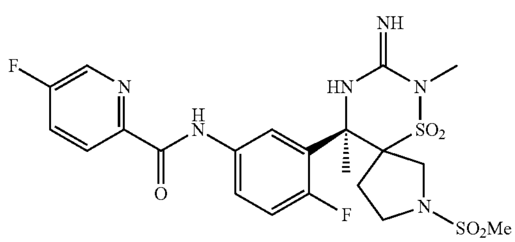 [SMILES: CN1C(=N)N[C@](C)(c2cc(NC(=O)c3ccc(F)cn3)ccc2F)C2(CCN(S(C)(=O)=O)C2)S1(=O)=O] | 5 | 9 | 543 | 2.33 | 1 |

Method H

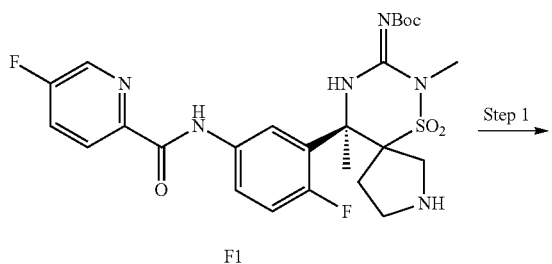

F1

Method I

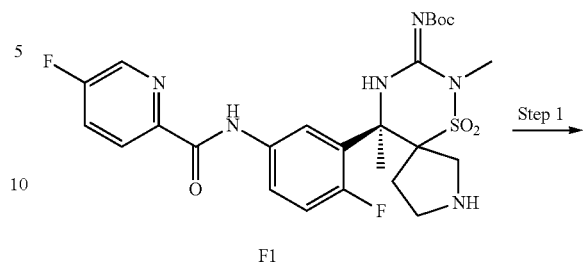

F1

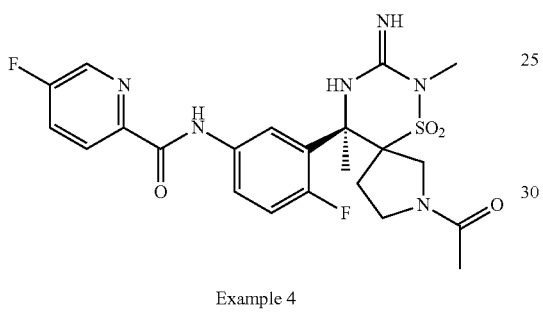

Example 4

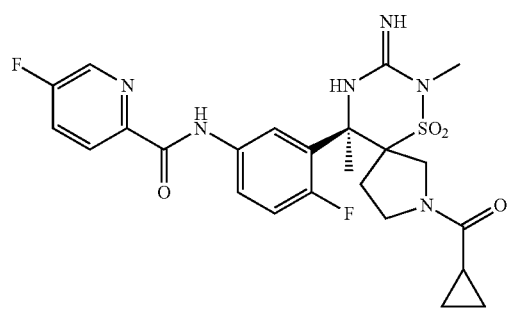 [SMILES: CN1C(=N)N[C@](C)(c2cc(NC(=O)c3ccc(F)cn3)ccc2F)C2(CCN(C(=O)C3CC3)C2)S1(=O)=O]

Example 5

Step 1:
To a solution of F1 (130 mg, 0.20 mmol) in pyridine (5 mL) at 0° C. was added Ac₂O (20 mg, 0.20 mmol). The mixture was stirred at 0° C. for 2 h, then quenched with H₂O, and extracted with EtOAc. The combined extracts were washed with brine, dried over Na₂SO₄, and concentrated. The residue was dissolved in 10% TFA in DCM (2 mL), stirred for 2 h, and concentrated. The crude residue was purified by RP-HPLC (column 30×150 mm, 5 μm; mobile phases A=water with 0.075% v/v TFA, B=MeCN; gradient elution 15-60% B, 10 min, 25 mL/min) to give Example 4.

Step 1:
To a solution of F1 (80 mg, 0.12 mmol) in DMF (2 mL) at RT were added cyclopropanecarboxylic acid (12 mg, 0.15 mmol), HATU (91 mg, 0.24 mmol), and DIEA (31 mg, 0.24 mmol). The mixture was stirred at RT for 16 h, then quenched by water and extracted with DCM. The combined extracts were washed with brine, dried over Na₂SO₄, and concentrated. The residue was dissolved in 10% TFA in DCM (2 mL), stirred for 2 h, and concentrated. The crude residue was purified by RP-HPLC (column 30×150 mm, 5 μm; mobile phases A=water with 0.075% v/v TFA, B=MeCN; gradient elution 15-60% B, 10 min, 25 mL/min) to give Example 5.

The Examples in Table 5 were prepared using a procedure similar to that described in Method I using the requisite carboxylic acids.

TABLE 4

| Ex. | Structure | BACE1 $K_i$ (nM) | BACE2 $K_i$ (nM) | LCMS data m/z (M + 1) | $t_R$ (min) | conditions |
|---|---|---|---|---|---|---|
| 4 | ![structure] | 3.7 | 9 | 507 | 2.24 | 1 |

TABLE 5

| Ex. | Structure | BACE1 $K_i$ (nM) | BACE2 $K_i$ (nM) | LCMS data m/z (M + 1) | $t_R$ (min) | conditions |
|---|---|---|---|---|---|---|
| 5 | 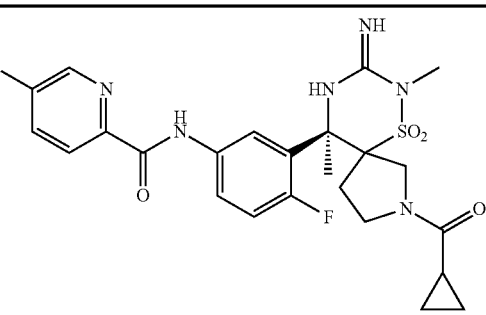 | 2.0 | 3.1 | 533 | 2.33 | 1 |
| 6 | 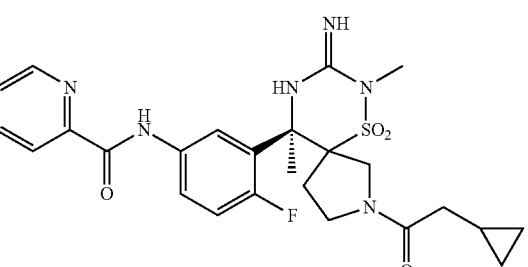 | 2.7 | 5.2 | 547 | 3.52 | 2 |
| 7 | 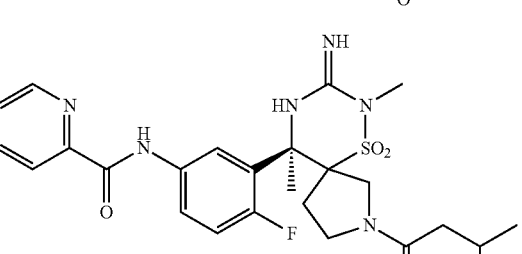 | 2.8 | 5.7 | 549 | 2.50 | 1 |

Method J

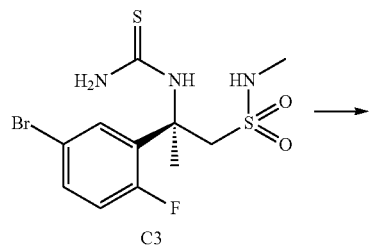

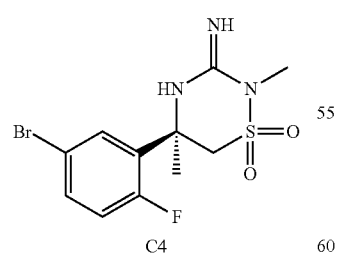

As an alternative procedure to Method C step 4, into a 20-L 4-necked round-bottom flask purged and maintained with an inert atmosphere of nitrogen was placed a solution of C3 (850 g, 2.21 mol, 1.00 equiv) in CH$_3$CN (8.5 L). This was followed by addition of trimethyloxonium tetrafluoroborate (343.7 g, 2.32 mol, 1.05 equiv) in several batches. After the mixture was stirred for 2 h at RT, the mixture was diluted with 5 L of ice/water and adjusted to pH 9 with sodium carbonate. The resulting solution was extracted with dichloromethane (5 L×3). The organic layers were combined, washed with brine (2 L), dried over anhydrous sodium sulfate, and concentrated under vacuum. To the residue was added ethanol (8.5 L) and the mixture was heated at reflux for 2 h. The reaction mixture was cooled and concentrated under vacuum. The obtained solid was washed with hexane to provide C4.

Method K

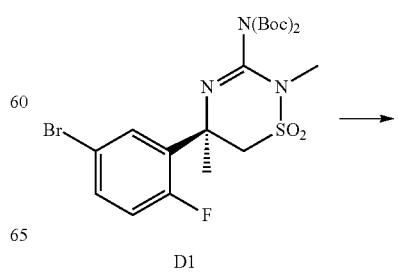

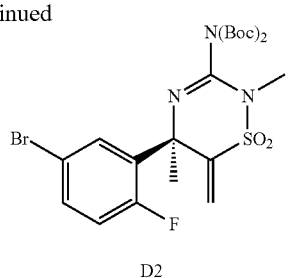

D2

As an alternative procedure to Method D step 2, LiHMDS (2.68 L, 2.50 equiv) was added to a solution of D1 (590 g, 1.07 mol, 1.00 equiv) in tetrahydrofuran (4720 mL) at −78° C. After the mixture was stirred for 1 h, to the mixture was added N-methyl-N-methylenemethanaminium iodide (397 g, 6.83 mol, 2.00 equiv) in several portions. The resulting mixture was stirred for 4 h at −78° C., followed by addition of iodomethane (761 g, 5.36 mol, 5.00 equiv) at 0° C. The resulting solution was stirred overnight at RT. To the mixture was added aq. NaHCO$_3$ (3 L) and the resultant mixture was stirred for an additional 1 h at RT. The resulting mixture was extracted with ethyl acetate (5 L×2). The organic layers were combined, washed with brine 1 L), dried over anhydrous sodium sulfate, and concentrated under vacuum. The residue was applied onto a silica gel column and eluted with ethyl acetate/petroleum ether (1:20) to provide D2.

Method L

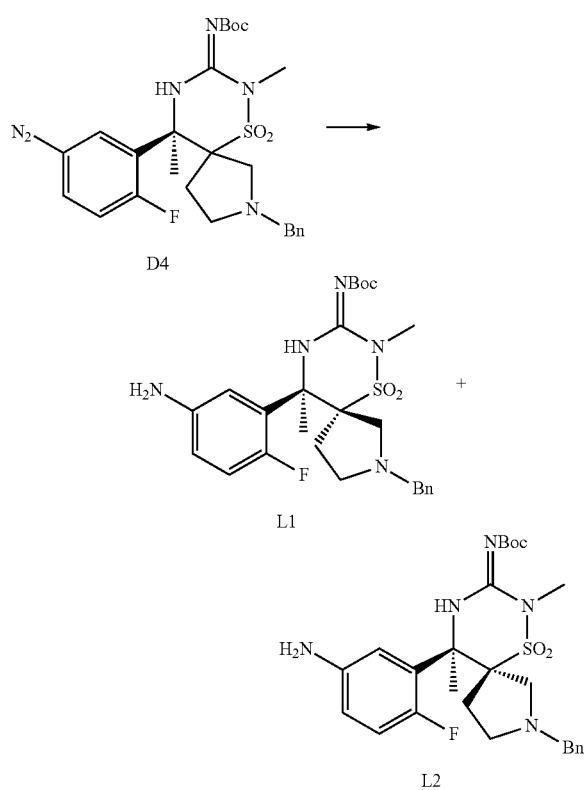

Into a 5000-mL 4-necked round-bottom flask purged and maintained with an inert atmosphere of nitrogen were added D4 (140 g, 250.61 mmol, 1.00 equiv), tetrahydrofuran (1050 mL), and water (350 mL). The resultant mixture was cooled to 0° C. To the mixture was added a solution of trimethylphosphine in toluene (376 mL, 1.50 equiv) dropwise with stirring at 0° C. The reaction mixture was then allowed to warm to RT and stir for 4 hours. After that time, the mixture was extracted with ethyl acetate (1 L×3). The organic layers were combined, washed with brine (500 mL), dried over anhydrous sodium sulfate, and concentrated under vacuum. The residue was applied onto a silica gel column and eluted with ethyl acetate/petroleum ether (gradient 1:6-1:5) to afford L1 along with L2 that required further purification. The residue containing L2 was repurified by flash chromatography using the following conditions: column, C18 silica; gradient elution 40-95% MeCN in water; Detector, UV 210 nm.) to afford L2. Analytical data for L1: m/z 532 [M+H$^+$] Analytical data for L2: m/z 532 [M+H].

Method M

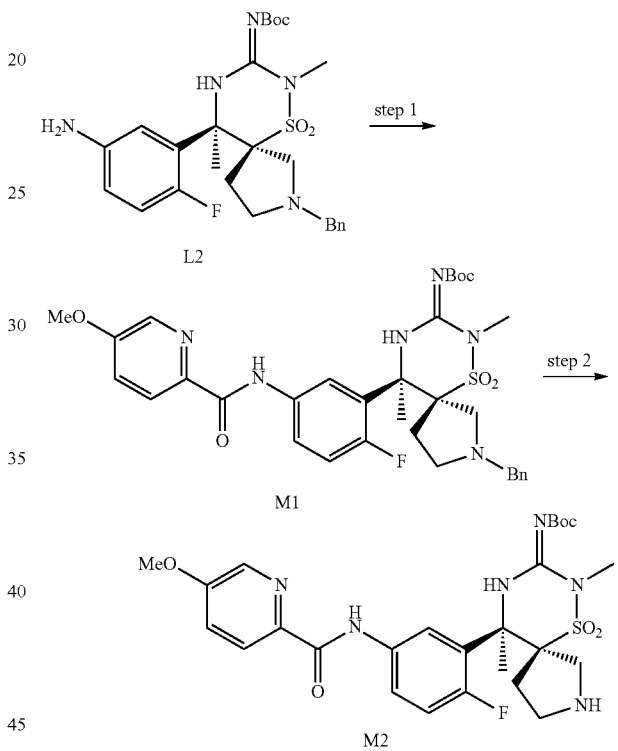

Step 1:
To a solution of L2 (500 mg, 0.941 mmol), 5-methoxy-2-picolinic acid (172 mg, 1.12 mmol), and DIEA (364.1 mg, 2.82 mmol) in tetrahydrofuran (7.5 mL) at 0° C. was added a solution of T3P (50% in EtOAc, 897.7 mg, 1.41 mmol). The reaction mixture was stirred for 5 h at RT. After that time, to the reaction was added cold water and the resultant reaction mixture was extracted with EtOAc. The combined organic layers were washed with brine, dried over anhydrous Na$_2$SO$_4$, and concentrated. The crude residue was purified by column chromatography (SiO$_2$) eluting with 50% EtOAc in hexanes to afford M1. m/z: 667.0 (M+H)$^+$, Step 2:
To a solution of M1 (200 mg, 0.3 mmol) in EtOAc (10 mL) was added 10% Pd/C (40 mg) followed by 2 drops of acetic acid. The reaction mixture was degassed and then stirred under an atmosphere of hydrogen (balloon) for 4 h. The reaction mixture was filtered through a celite bed and the filter bed was washed with 1:1 mixture of dichloromethane and methanol. The combined filtrates were concentrated and purified by column chromatography (SiO$_2$) eluting with 10% methanol in dichloromethane to yield M2. m/z: 577.0 (M+H$^+$).

TABLE 6

Intermediates M3-M5 were prepared using procedures similar to those described in Scheme M from either L1 or L2 and the requisite carboxylic acids.

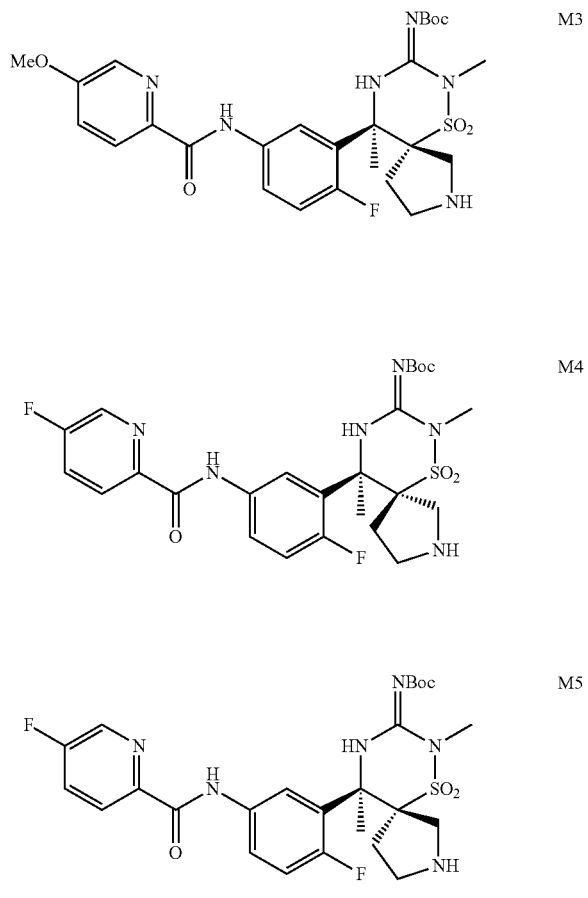

Method N

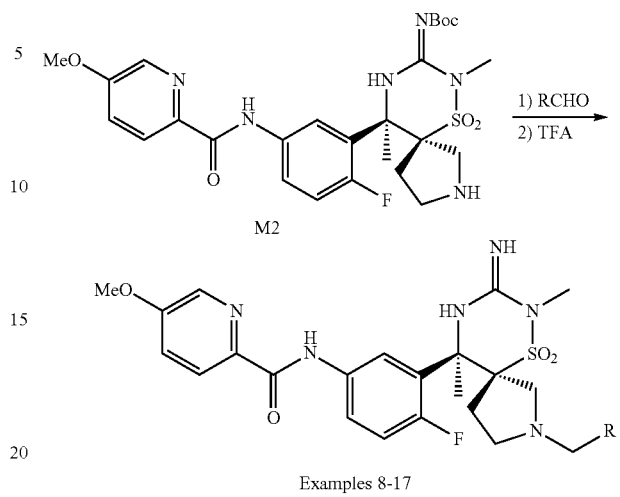

Parallel preparation of Examples 8-17: To a set of vials each containing a solution of M2 (25 mg, 0.043 mmol) in MeOH (1 mL) was added the requisite aldehyde (0.052 mmol) and acetic acid (0.010 mL, 0.17 mmol). The solutions were shaken at RT for 10 min. To each of the vials was then added MP-cyanoborohydride (Biotage) (48 mg, 0.10 mmol) and the mixtures were shaken at RT overnight. The mixtures were then filtered and the solvent was removed in vacuo. To each vial was added TFA (0.5 mL). The mixtures were shaken at RT for 3 hours. The solvent was then removed in vacuo. Each crude residue was redissolved in 1 mL of DMSO and filtered. The residues containing Examples 8-16 were purified by mass triggered HPLC using the following conditions: [Waters XBridge C18 column, 5 µm, 19×100 mm, gradient ranges from 10% initial to 60-70% MeCN (0.1% NH$_4$OH) in water (0.1% NH$_4$OH) 50 mL/min, 8-15 min run time] to provide Examples 8-16. The crude residue containing Example 17 was purified by mass triggered HPLC using the following conditions: [column: Waters Sunfire C18, 5 µm, 19×100 mm; solvent: gradient range 10% initial to 40% final MeCN (0.1% formic acid) in water (0.1% formic acid) 50 mL/min; 8 min run time] to afford Example 17.

TABLE 7

| Ex. | Structure | BACE1 K$_i$ (nM) | BACE2 K$_i$ (nM) | LCMS data m/z (M + 1) | t$_R$ (min) | conditions |
|---|---|---|---|---|---|---|
| 8 | | 3 | 13 | 574.16 | 0.75 | 3 |

TABLE 7-continued

| | | BACE1 $K_i$ (nM) | BACE2 $K_i$ (nM) | LCMS data | | |
|---|---|---|---|---|---|---|
| Ex. | Structure | | | m/z (M + 1) | $t_R$ (min) | conditions |
| 9 | | 1 | 2 | 561.22 | 0.73 | 3 |
| 10 | | 2 | 13 | 568.21 | 0.72 | 3 |
| 11 | | 2 | 12 | 568.21 | 0.72 | 3 |
| 12 | | 2 | 7 | 531.21 | 0.71 | 3 |
| 13 | | 1 | 1 | 573.18 | 0.99 | 3 |

TABLE 7-continued
| Ex. | Structure | BACE1 $K_i$ (nM) | BACE2 $K_i$ (nM) | LCMS data m/z (M + 1) | $t_R$ (min) | conditions |
|---|---|---|---|---|---|---|
| 14 | | 3 | 9 | 558.1 (M + 1)9 | 0.79 | 3 |
| 15 | | 4 | 17 | 569.2 | 0.82 | 3 |
| 16 | | 4 | 26 | 571.22 | 0.67 | 3 |
| 17 | | 4 | 21 | 575.24 | 0.73 | 3 |
Method O
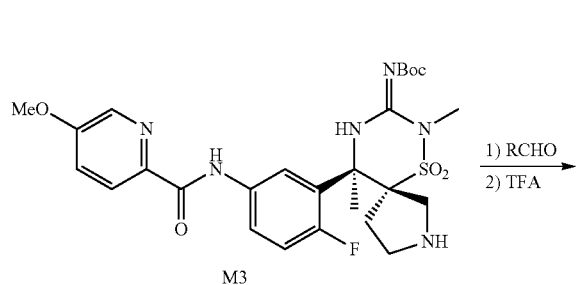
M3
1) RCHO
2) TFA
-continued
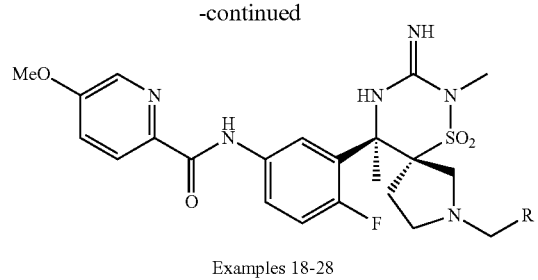
Examples 18-28

Parallel preparation of Examples 18-28: These examples were prepared from M3 and the requisite aldehydes using a procedure similar to that described in Method N. The crude residues were purified by mass triggered HPLC using the following conditions: [column: Waters XBridge C18, 5 μm, 19×100 mm; solvent: gradient range 20-35% initial to 55-70% final MeCN (0.1% NH$_4$OH) in water (0.1% NH$_4$OH) 25 mL/min; 8 min run time] to afford Examples 18-28.

TABLE 8

| Ex. | Structure | BACE1 K$_i$ (nM) | BACE2 K$_i$ (nM) | LCMS data m/z (M + 1) | t$_R$ (min) | conditions |
|---|---|---|---|---|---|---|
| 18 | 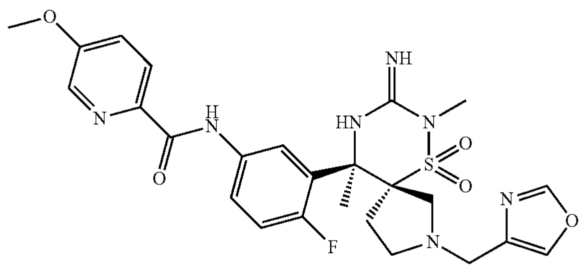 [SMILES: COc1ccc(C(=O)Nc2ccc(F)c([C@@]3(C)NC(=N)N(C)S(=O)(=O)[C@]34CCN(Cc3cocn3)C4)c2)nc1] | 47 | 158 | 558.19 | 0.70 | 3 |
| 19 | 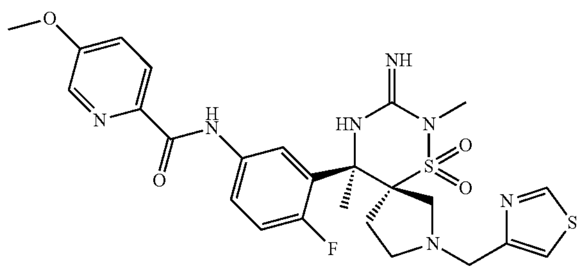 [SMILES: COc1ccc(C(=O)Nc2ccc(F)c([C@@]3(C)NC(=N)N(C)S(=O)(=O)[C@]34CCN(Cc3cscn3)C4)c2)nc1] | 20 | 70 | 574.16 | 0.73 | 3 |
| 20 | 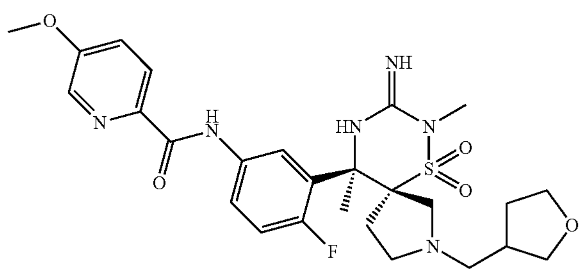 [SMILES: COc1ccc(C(=O)Nc2ccc(F)c([C@@]3(C)NC(=N)N(C)S(=O)(=O)[C@]34CCN(CC3CCOC3)C4)c2)nc1] | 51 | 188 | 561.22 | 0.73 | 3 |
| 21 | 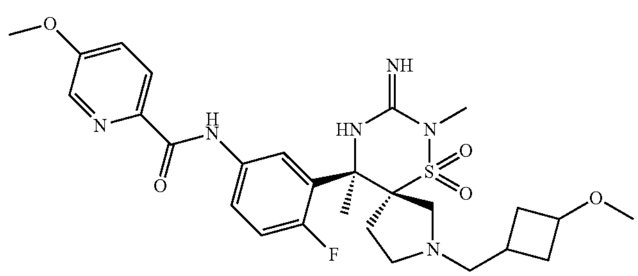 | 91 | 201 | 575.24 | 0.72 | 3 |
| 22 | 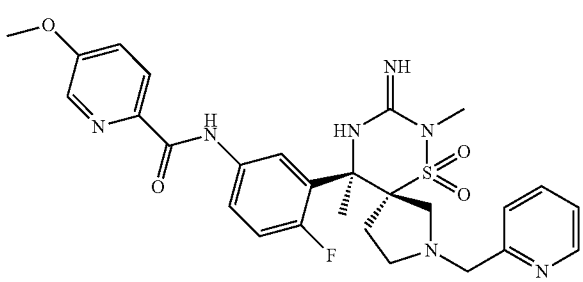 [SMILES: COc1ccc(C(=O)Nc2ccc(F)c([C@@]3(C)NC(=N)N(C)S(=O)(=O)[C@]34CCN(Cc3ccccn3)C4)c2)nc1] | 26 | 79 | 568.21 | 0.71 | 3 |

TABLE 8-continued
| Ex. | Structure | BACE1 $K_i$ (nM) | BACE2 $K_i$ (nM) | LCMS data m/z (M + 1) | $t_R$ (min) | conditions |
|---|---|---|---|---|---|---|
| 23 | 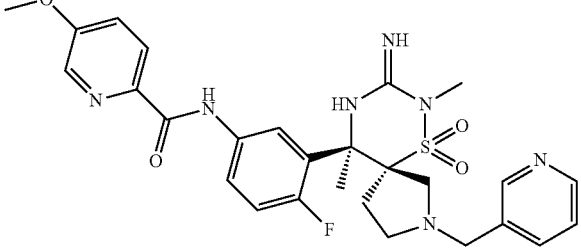 | 30 | 142 | 568.21 | 0.71 | 3 |
| 24 | 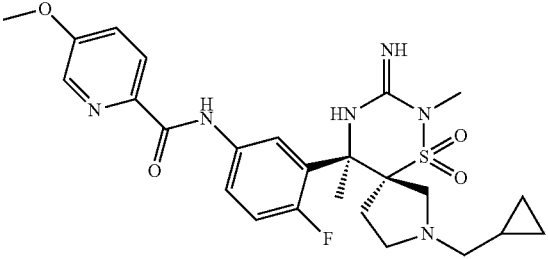 [SMILES: COc1ccc(C(=O)Nc2ccc(F)c([C@@]3(C)NC(=N)N(C)S(=O)(=O)[C@]34CCN(CC3CC3)C4)c2)nc1] | 34 | 128 | 531.21 | 0.70 | 3 |
| 25 | 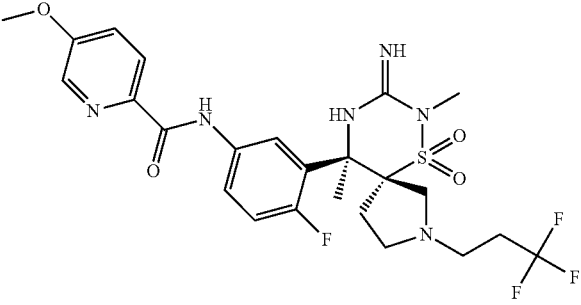 [SMILES: COc1ccc(C(=O)Nc2ccc(F)c([C@@]3(C)NC(=N)N(C)S(=O)(=O)[C@]34CCN(CCC(F)(F)F)C4)c2)nc1] | 15 | 52 | 573.18 | 1.02 | 3 |
| 26 | 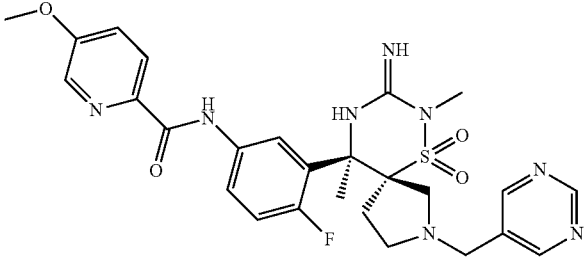 [SMILES: COc1ccc(C(=O)Nc2ccc(F)c([C@@]3(C)NC(=N)N(C)S(=O)(=O)[C@]34CCN(Cc3cncnc3)C4)c2)nc1] | 51 | 329 | 569.2 | 0.84 | 3 |
| 27 | 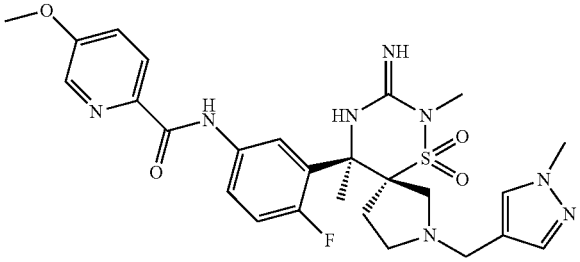 [SMILES: COc1ccc(C(=O)Nc2ccc(F)c([C@@]3(C)NC(=N)N(C)S(=O)(=O)[C@]34CCN(Cc3cnn(C)c3)C4)c2)nc1] | 54 | 388 | 571.22 | 0.64 | 3 |

TABLE 8-continued

| Ex. | Structure | BACE1 K$_i$ (nM) | BACE2 K$_i$ (nM) | m/z (M + 1) | t$_R$ (min) | conditions |
|---|---|---|---|---|---|---|
| 28 | 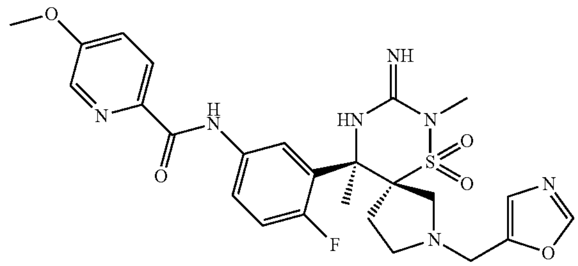 [SMILES: COc1ccc(C(=O)Nc2ccc(F)c([C@@]3(C)NC(=N)N(C)S(=O)(=O)[C@]34CCN(Cc3cnco3)C4)c2)nc1] | 28 | 237 | 558.19 | 0.79 | 3 |

Method P

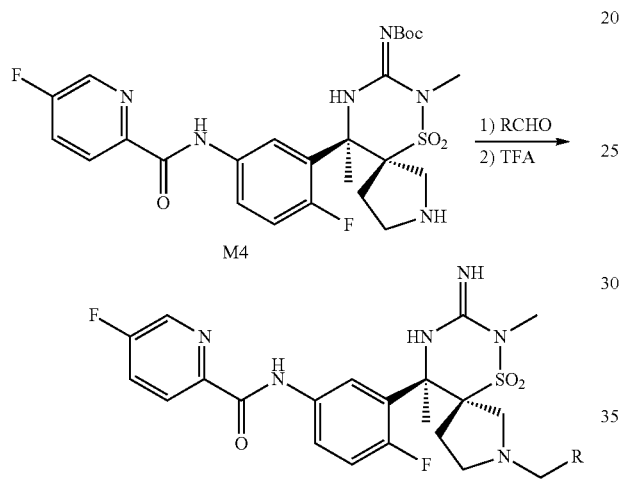

M4

Examples 29-41

Parallel preparation of Examples 29-41: These examples were prepared from M4 and the requisite aldehyde using a procedure similar to that described in Method N. The crude residues were purified by mass triggered HPLC using the following conditions: [column: Waters XBridge C18, 5 μm, 19×100 mm; solvent: gradient range 15-30% initial to 50-70% final MeCN (0.1% NH$_4$OH) in water (0.1% NH$_4$OH) 25 mL/min; 8 min run time] to afford Examples 29-41.

TABLE 9

| Ex. | Structure | BACE1 K$_i$ (nM) | BACE2 K$_i$ (nM) | m/z (M + 1) | t$_R$ (min) | conditions |
|---|---|---|---|---|---|---|
| 29 | 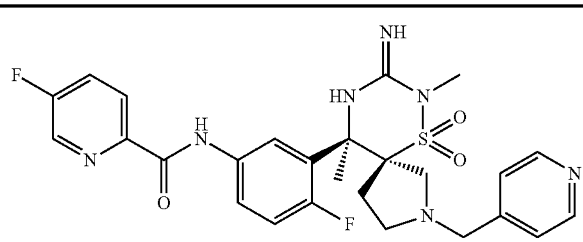 | 8 | 9 | 556.19 | 0.70 | 3 |

TABLE 9-continued
| Ex. | Structure | BACE1 $K_i$ (nM) | BACE2 $K_i$ (nM) | LCMS data m/z (M + 1) | $t_R$ (min) | conditions |
|---|---|---|---|---|---|---|
| 30 | 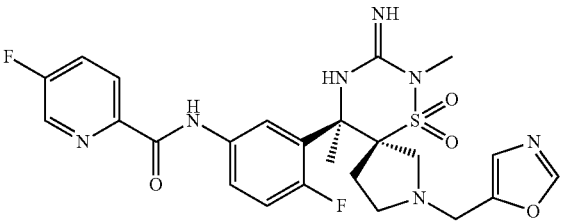 [SMILES: CN1C(=N)N[C@](C)(c2cc(NC(=O)c3ccc(F)cn3)ccc2F)[C@]2(CCN(Cc3cnco3)C2)S1(=O)=O] | 4 | 5 | 546.17 | 0.78 | 3 |
| 31 | 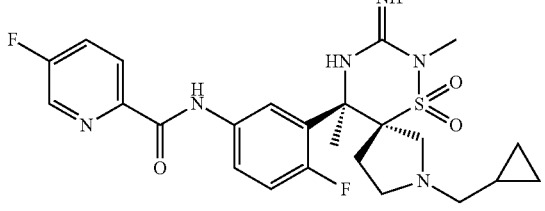 | 2 | 5 | 519.19 | 0.70 | 3 |
| 32 | 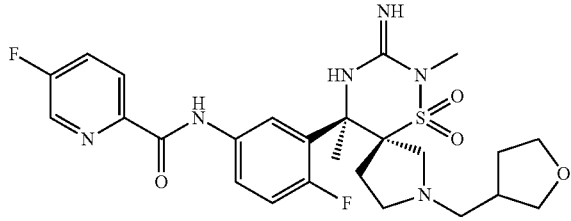 [SMILES: CN1C(=N)N[C@](C)(c2cc(NC(=O)c3ccc(F)cn3)ccc2F)[C@]2(CCN(CC3CCOC3)C2)S1(=O)=O] | 1 | 1 | 549.2 | 0.71 | 3 |
| 33 | 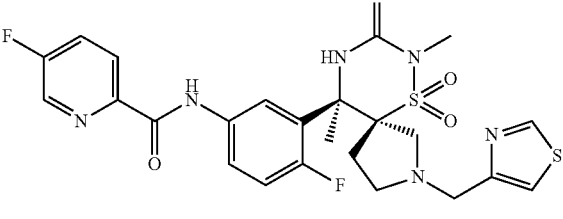 | 3 | 5 | 562.14 | 0.73 | 3 |
| 34 | 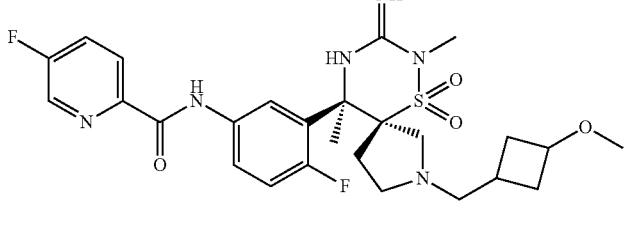 | 6 | 10 | 563.22 | 0.72 | 3 |
| 35 | 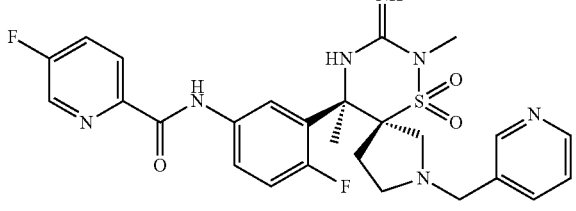 | 2 | 6 | 556.19 | 0.70 | 3 |

TABLE 9-continued

| | | BACE1 | BACE2 | LCMS data | | |
|---|---|---|---|---|---|---|
| Ex. | Structure | K$_i$ (nM) | K$_i$ (nM) | m/z (M + 1) | t$_R$ (min) | conditions |
| 36 | | 1 | 1 | 561.16 | 0.98 | 3 |
| 37 | | 2 | 5 | 546.17 | 0.70 | 3 |
| 38 | | 4 | 7 | 557.18 | 0.80 | 3 |
| 39 | | 2 | 3 | 521.21 | 0.74 | 3 |
| 40 | | 4 | 10 | 559.2 | 0.65 | 3 |

TABLE 9-continued

| Ex. | Structure | BACE1 $K_i$ (nM) | BACE2 $K_i$ (nM) | LCMS data m/z (M + 1) | $t_R$ (min) | conditions |
|---|---|---|---|---|---|---|
| 41 | | 3 | 6 | 556.19 | 0.71 | 3 |

Method Q

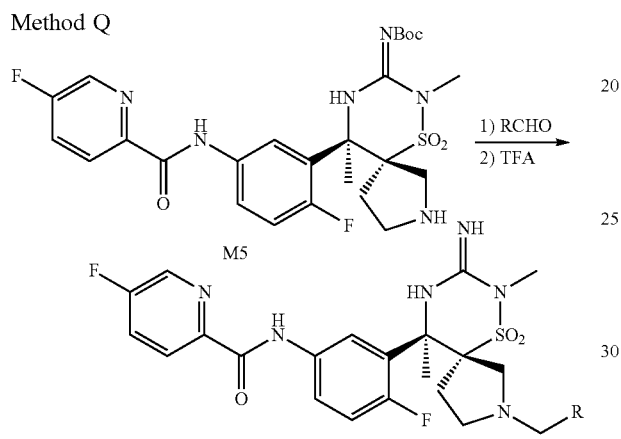

Examples 42-54

Parallel preparation of Examples 42-54: These examples were prepared from M5 and the requisite aldehydes using a procedure similar to that described in Method N. The crude residues containing examples 42-53 were purified by mass triggered HPLC using the following conditions: [column: Waters Sunfire C18, 5 μm, 19×100 mm; solvent: gradient range 8-15% initial to 35-50% final MeCN (0.1% formic acid) in water (0.1% formic acid) 25 mL/min; 8 min run time] to afford Examples 42-53. The crude residue containing Example 54 was purified using the following conditions: [column: Waters XBridge C18, 5 μm, 19×100 mm; solvent: gradient from 20% initial to 55% final MeCN (0.1% NH$_4$OH) in water (0.1% NH$_4$OH) 25 mL/min; 8 min run time] to afford Example 54.

TABLE 10

| Ex. | Structure | BACE1 $K_i$ (nM) | BACE2 $K_i$ (nM) | LCMS data m/z (M + 1) | $t_R$ (min) | conditions |
|---|---|---|---|---|---|---|
| 42 | | 32 | 25 | 562.14 | 0.71 | 3 |

TABLE 10-continued

| Ex. | Structure | BACE1 $K_i$ (nM) | BACE2 $K_i$ (nM) | m/z (M + 1) | $t_R$ (min) | conditions |
|---|---|---|---|---|---|---|
| 43 | 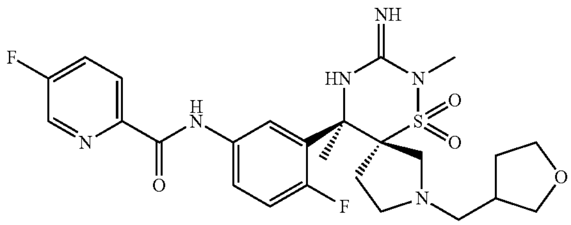 [SMILES: CN1C(=N)N[C@](C)(c2cc(NC(=O)c3ccc(F)cn3)ccc2F)[C@@]2(CCN(CC3CCOC3)C2)S1(=O)=O] | 119 | 72 | 549.2 | 0.71 | 3 |
| 44 | 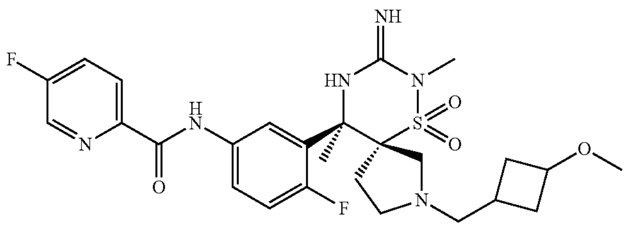 [SMILES: COC1CC(CN2CC[C@]3(C2)[C@@](C)(c2cc(NC(=O)c4ccc(F)cn4)ccc2F)NC(=N)N(C)S3(=O)=O)C1] | 120 | 52 | 563.22 | 0.70 | 3 |
| 45 | 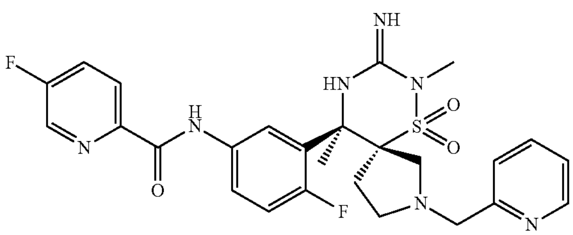 [SMILES: CN1C(=N)N[C@](C)(c2cc(NC(=O)c3ccc(F)cn3)ccc2F)[C@@]2(CCN(Cc3ccccn3)C2)S1(=O)=O] | 33 | 23 | 556.19 | 0.69 | 3 |
| 46 | 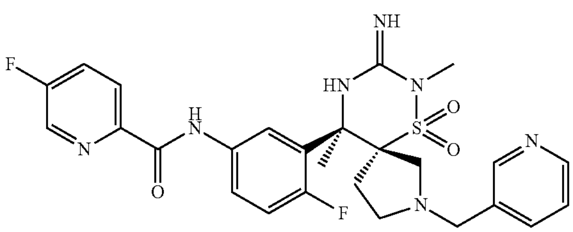 [SMILES: CN1C(=N)N[C@](C)(c2cc(NC(=O)c3ccc(F)cn3)ccc2F)[C@@]2(CCN(Cc3cccnc3)C2)S1(=O)=O] | 54 | 40 | 556.19 | 0.69 | 3 |
| 47 | 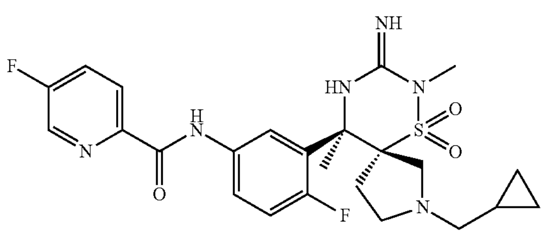 [SMILES: CN1C(=N)N[C@](C)(c2cc(NC(=O)c3ccc(F)cn3)ccc2F)[C@@]2(CCN(CC3CC3)C2)S1(=O)=O] | 58 | 51 | 519.19 | 0.68 | 3 |
| 48 | 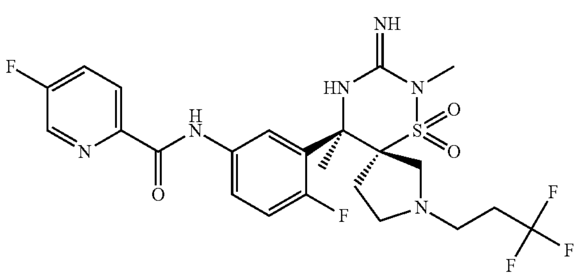 [SMILES: CN1C(=N)N[C@](C)(c2cc(NC(=O)c3ccc(F)cn3)ccc2F)[C@@]2(CCN(CCC(F)(F)F)C2)S1(=O)=O] | 22 | 14 | 561.16 | 1.01 | 3 |

TABLE 10-continued
| Ex. | Structure | BACE1 $K_i$ (nM) | BACE2 $K_i$ (nM) | LCMS data m/z (M + 1) | $t_R$ (min) | conditions |
|---|---|---|---|---|---|---|
| 49 | 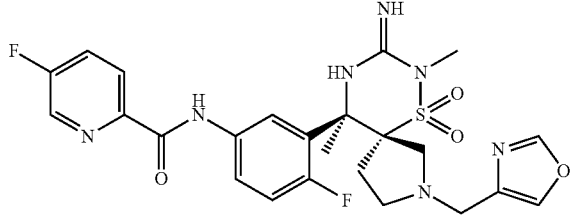 [SMILES: CN1C(=N)N[C@](C)(c2cc(NC(=O)c3ccc(F)cn3)ccc2F)[C@@]2(CCN(Cc3cocn3)C2)S1(=O)=O] | 33 | 21 | 546.17 | 0.68 | 3 |
| 50 | 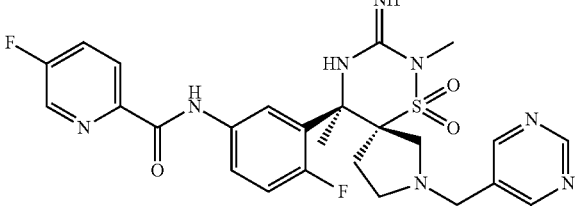 | 70 | 77 | 557.18 | 0.82 | 3 |
| 51 | 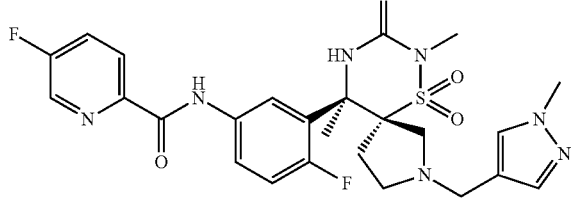 | 151 | 184 | 559.2 | 0.62 | 3 |
| 52 | 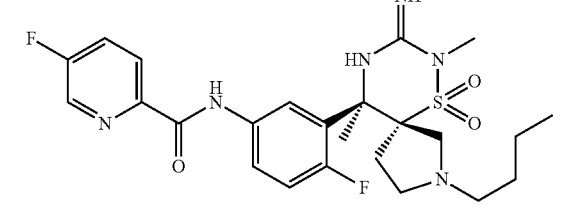 | 73 | 61 | 521.21 | 0.73 | 3 |
| 53 | 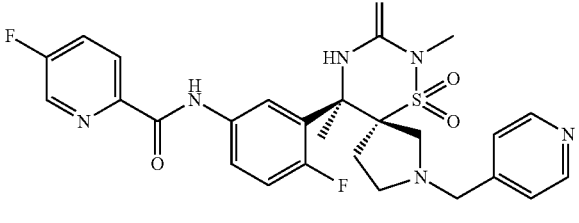 | 84 | 61 | 556.19 | 0.69 | 3 |

TABLE 10-continued

| Ex. | Structure | BACE1 $K_i$ (nM) | BACE2 $K_i$ (nM) | m/z (M + 1) | $t_R$ (min) | conditions |
|---|---|---|---|---|---|---|
| 54 | 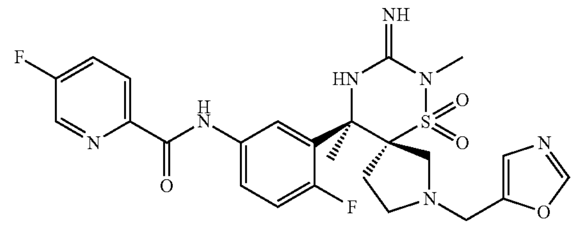 [SMILES: CN1C(=N)N[C@](C)(c2cc(NC(=O)c3ccc(F)cn3)ccc2F)[C@@]2(CCN(Cc3cnco3)C2)S1(=O)=O] | 54 | 74 | 546.17 | 0.77 | 3 |

Method R

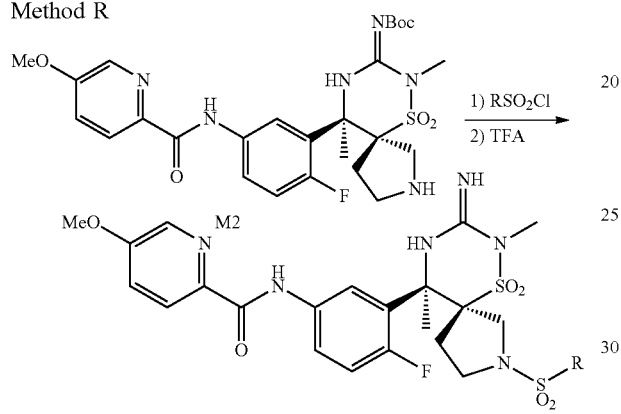

Examples 55-62

Parallel preparation of Examples 55-62: To a set of vials each containing a solution of M2 (30 mg, 0.052 mmol) in DCM (1 mL) was added iPr$_2$NEt (0.027 mL, 0.16 mmol) followed by the requisite sulfonyl chlorides (0.10 mmol). The solutions were shaken at RT overnight. After that time, to each of the vials was added TFA (0.5 mL). The mixtures were shaken at RT for 3 h and the solvent was then removed in vacuo. Each crude residue was redissolved in 1 mL of DMSO and filtered. The crude residues were purified by mass triggered HPLC using the following conditions: [Waters XBridge C18 column, 5 μm, 19×100 mm, gradient ranges from 17-35% initial to 55-70% MeCN (0.1% NH$_4$OH) in water (0.1% NH$_4$OH) 25 mL/min, 8 min run time] to provide Examples 55-62.

TABLE 11

| Ex. | Structure | BACE1 $K_i$ (nM) | BACE2 $K_i$ (nM) | m/z (M + 1) | $t_R$ (min) | conditions |
|---|---|---|---|---|---|---|
| 55 | 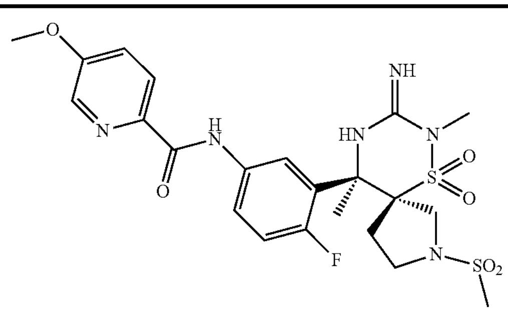 | 3 | 10 | 555.14 | 0.85 | 3 |

TABLE 11-continued
| Ex. | Structure | BACE1 $K_i$ (nM) | BACE2 $K_i$ (nM) | m/z (M + 1) | $t_R$ (min) | conditions |
|---|---|---|---|---|---|---|
| 56 | 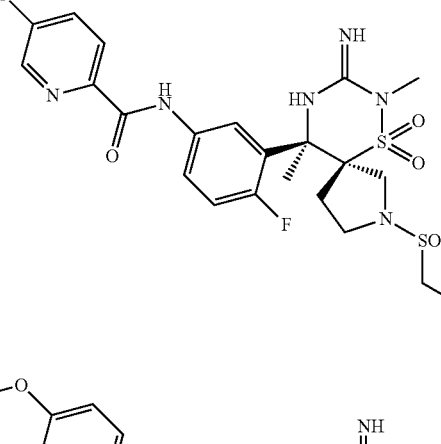 | 1 | 6 | 569.16 | 0.90 | 3 |
| 57 | 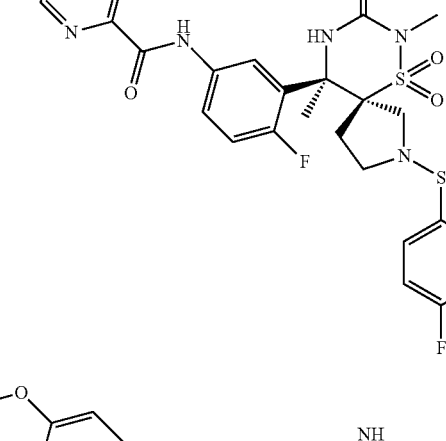 | 1 | 5 | 597.19 | 1.04 | 3 |
| 58 | 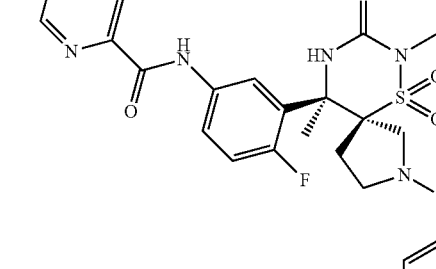 | 3 | 20 | 635.15 | 1.06 | 3 |
| 59 | 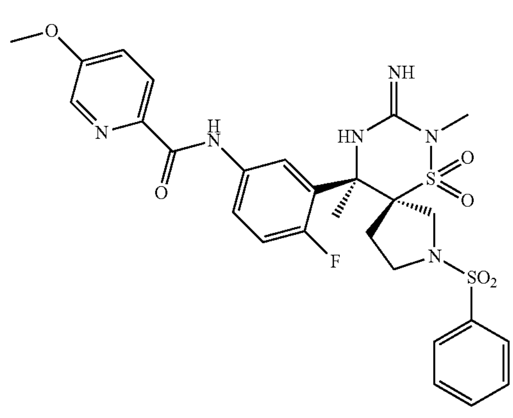 [SMILES: COc1ccc(C(=O)Nc2ccc(F)c([C@@]3(C)NC(=N)N(C)S(=O)(=O)[C@@]34CCN(S(=O)(=O)c3ccccc3)C4)c2)nc1] | 3 | 16 | 617.16 | 1.03 | 3 |

TABLE 11-continued
| Ex. | Structure | BACE1 $K_i$ (nM) | BACE2 $K_i$ (nM) | LCMS data m/z (M + 1) | $t_R$ (min) | conditions |
|---|---|---|---|---|---|---|
| 60 | 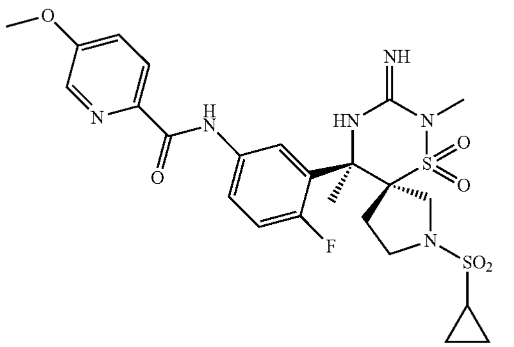 [SMILES: COc1ccc(C(=O)Nc2ccc(F)c([C@@]3(C)NC(=N)N(C)S(=O)(=O)[C@@]34CCN(S(=O)(=O)C3CC3)C4)c2)nc1] | 1 | 4 | 581.16 | 0.93 | 3 |
| 61 | 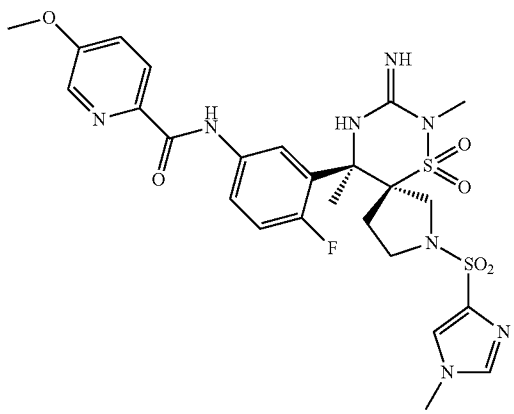 [SMILES: COc1ccc(C(=O)Nc2ccc(F)c([C@@]3(C)NC(=N)N(C)S(=O)(=O)[C@@]34CCN(S(=O)(=O)c3cn(C)cn3)C4)c2)nc1] | 6 | 38 | 621.16 | 0.83 | 3 |
| 62 | 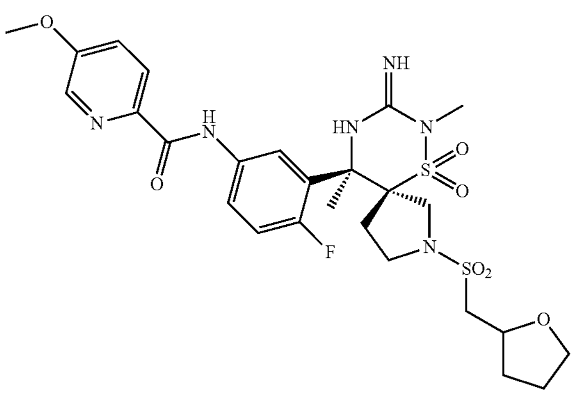 [SMILES: COc1ccc(C(=O)Nc2ccc(F)c([C@@]3(C)NC(=N)N(C)S(=O)(=O)[C@@]34CCN(S(=O)(=O)CC3CCCO3)C4)c2)nc1] | 3 | 19 | 625.18 | 0.94 | 3 |
Method S
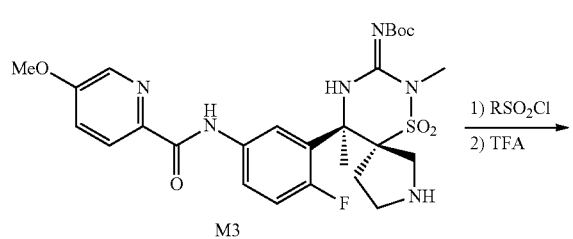
M3
1) RSO$_2$Cl
2) TFA
-continued
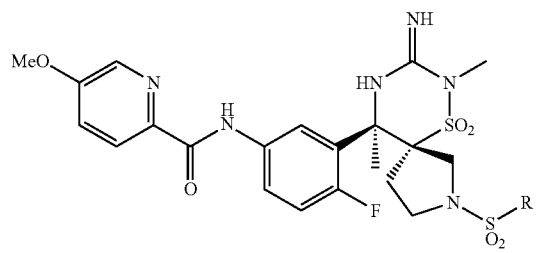
Examples 63-72

Parallel preparation of Examples 63-72: These examples were prepared from M3 and the requisite sulfonyl chlorides using a procedure similar to that described in Method R. The crude residues were purified by mass triggered HPLC using the following conditions: [column: Waters XBridge C18, 5 μm, 19×100 mm; solvent: gradient range 12-27% initial to 42-57% final MeCN (0.1% NH$_4$OH) in water (0.1% NH$_4$OH) 25 mL/min; 8 min run time] to afford Examples 63-71. Example 72 was repurified by mass triggered HPLC using the following conditions: [column: Waters Sunfire C18, 5 μm, 19×100 mm; solvent: gradient of 10% initial to 32% final MeCN (0.1% formic acid) in water (0.1% formic acid) 50 mL/min; 8 min run time] to afford Example 72.

TABLE 12

| Ex. | Structure | BACE1 K$_i$ (nM) | BACE2 K$_i$ (nM) | LCMS data m/z (M + 1) | t$_R$ (min) | conditions |
|---|---|---|---|---|---|---|
| 63 | 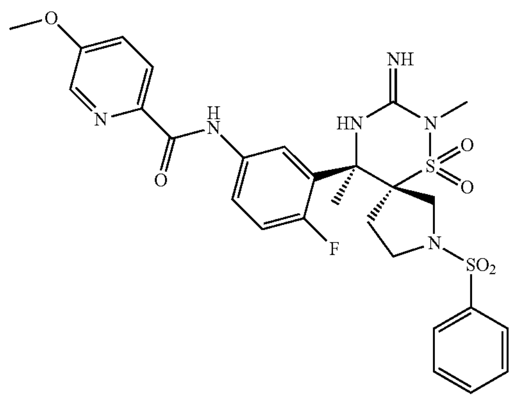 [SMILES: COc1ccc(C(=O)Nc2ccc(F)c([C@@]3(C)NC(=N)N(C)S(=O)(=O)[C@]34CCN(S(=O)(=O)c3ccccc3)C4)c2)nc1] | 12 | 24 | 617.16 | 1.02 | 3 |
| 64 | 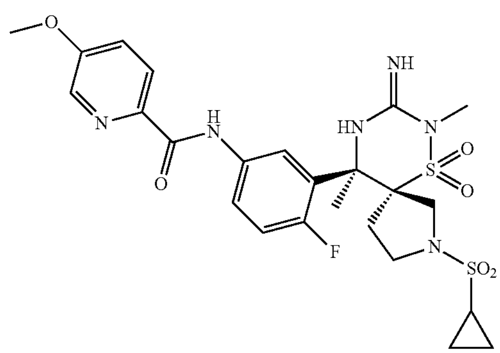 [SMILES: COc1ccc(C(=O)Nc2ccc(F)c([C@@]3(C)NC(=N)N(C)S(=O)(=O)[C@]34CCN(S(=O)(=O)C3CC3)C4)c2)nc1] | 40 | 140 | 581.16 | 0.91 | 3 |
| 65 | 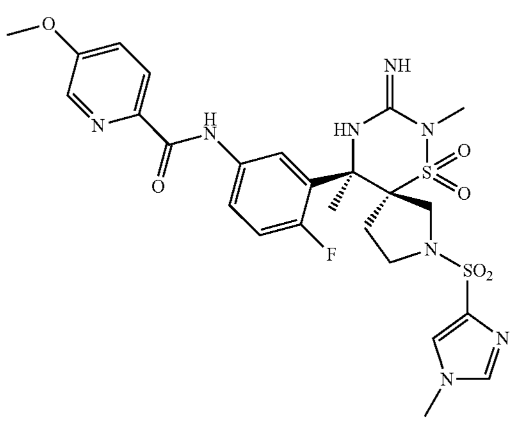 [SMILES: COc1ccc(C(=O)Nc2ccc(F)c([C@@]3(C)NC(=N)N(C)S(=O)(=O)[C@]34CCN(S(=O)(=O)c3cn(C)cn3)C4)c2)nc1] | 29 | 68 | 621.16 | 0.81 | 3 |

TABLE 12-continued

| Ex. | Structure | BACE1 K_i (nM) | BACE2 K_i (nM) | LCMS data m/z (M + 1) | t_R (min) | conditions |
|---|---|---|---|---|---|---|
| 66 | 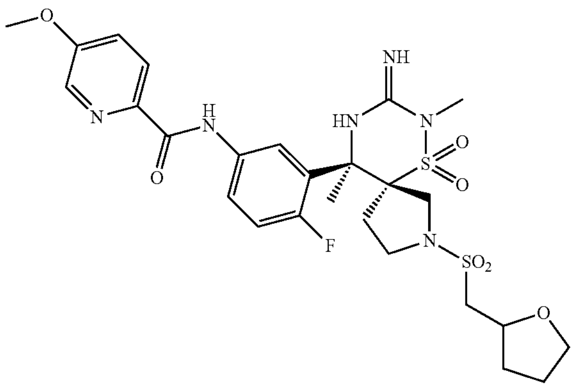 [SMILES: COc1ccc(C(=O)Nc2ccc(F)c([C@@]3(C)NC(=N)N(C)S(=O)(=O)[C@]34CCN(S(=O)(=O)CC3CCCO3)C4)c2)nc1] | 32 | 87 | 625.18 | 0.93 | 3 |
| 67 | 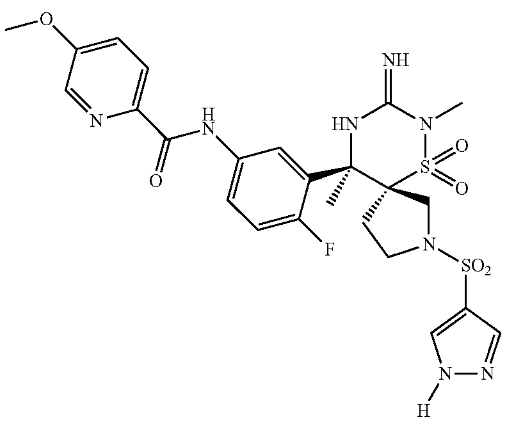 [SMILES: COc1ccc(C(=O)Nc2ccc(F)c([C@@]3(C)NC(=N)N(C)S(=O)(=O)[C@]34CCN(S(=O)(=O)c3cn[nH]c3)C4)c2)nc1] | 20 | 40 | 607.15 | 0.82 | 3 |
| 68 | 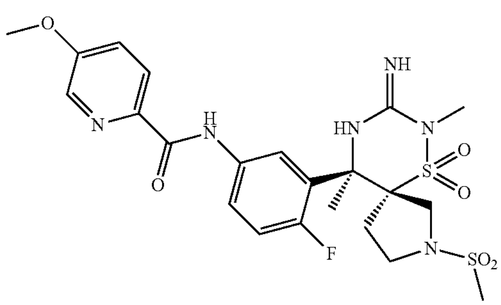 | 35 | 205 | 555.14 | 0.83 | 3 |
| 69 | 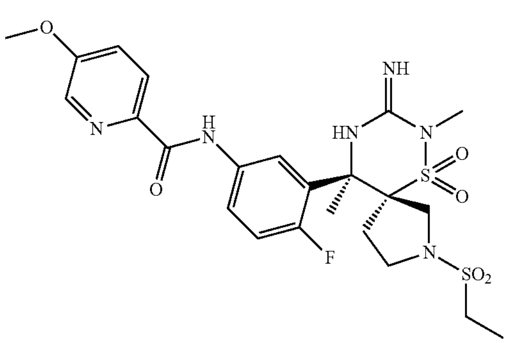 [SMILES: CCS(=O)(=O)N1CC[C@]2(C1)[C@@](C)(c1cc(NC(=O)c3ccc(OC)cn3)ccc1F)NC(=N)N(C)S2(=O)=O] | 33 | 157 | 569.16 | 0.89 | 3 |

TABLE 12-continued
| Ex. | Structure | BACE1 $K_i$ (nM) | BACE2 $K_i$ (nM) | LCMS data m/z (M + 1) | $t_R$ (min) | conditions |
|---|---|---|---|---|---|---|
| 70 | 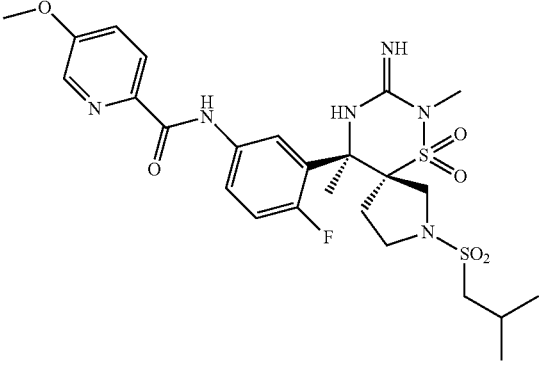 [SMILES: COc1ccc(C(=O)Nc2ccc(F)c([C@@]3(C)NC(=N)N(C)S(=O)(=O)[C@]34CCN(S(=O)(=O)CC(C)C)C4)c2)nc1] | 37 | 100 | 597.19 | 1.02 | 3 |
| 71 | 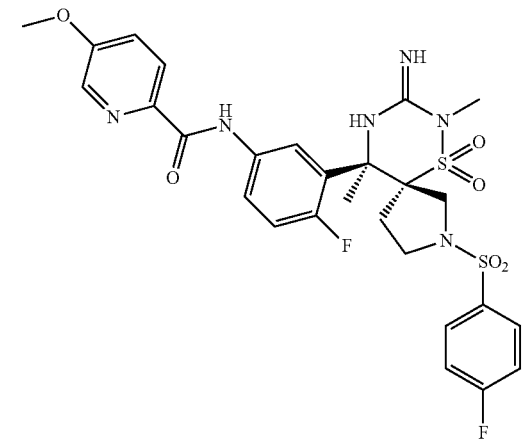 [SMILES: COc1ccc(C(=O)Nc2ccc(F)c([C@@]3(C)NC(=N)N(C)S(=O)(=O)[C@]34CCN(S(=O)(=O)c3ccc(F)cc3)C4)c2)nc1] | 24 | 30 | 635.15 | 1.04 | 3 |
| 72 | 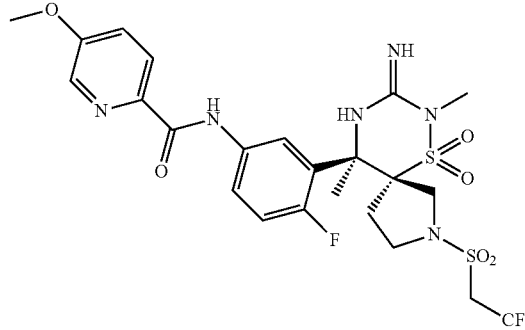 | 28 | 99 | 623.13 | 0.99 | 3 |
Method T
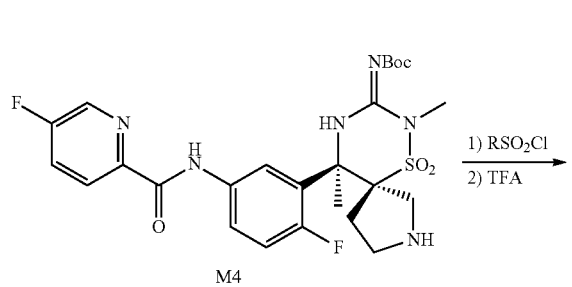
M4
-continued
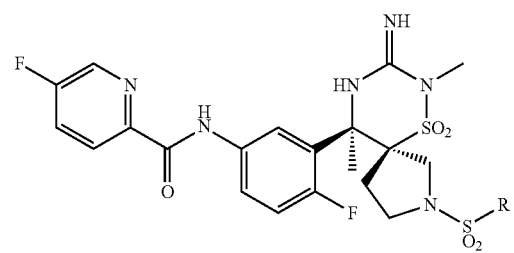
Examples 73-84

Parallel preparation of Examples 73-84: These examples were prepared from M4 and the requisite sulfonyl chlorides using a procedure similar to that described in Method R. The crude residues were purified by mass triggered HPLC using the following conditions: [column: Waters Sunfire C18, 5 µm, 19×100 mm; solvent: gradient range 8-20% initial to 40-55% final MeCN (0.1% TFA) in water (0.1% TFA) 25 mL/min; 8-12 min run time] to afford Examples 73-83. Example 84 was repurified by mass triggered HPLC using the following conditions: [column: Waters XBridge C18, 5 µm, 19×100 mm; solvent: gradient from 30% initial to 65% final MeCN (0.1% NH₄OH) in water (0.1% NH₄OH) 25 mL/min; 8 min run time] to afford Example 84.

TABLE 13

| Ex. | Structure | BACE1 $K_i$ (nM) | BACE2 $K_i$ (nM) | LCMS data m/z | $t_R$ (min) | conditions |
|---|---|---|---|---|---|---|
| 73 | 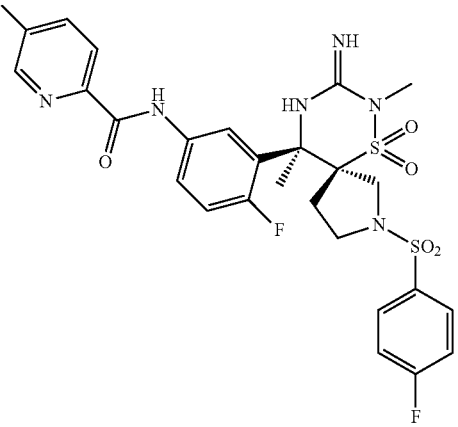 | 3 | 10 | 623.13 | 1.07 | 3 |
| 74 | 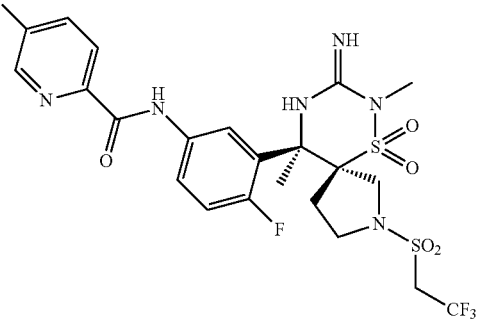 | 2 | 4 | 611.11 | 1.02 | 3 |
| 75 | 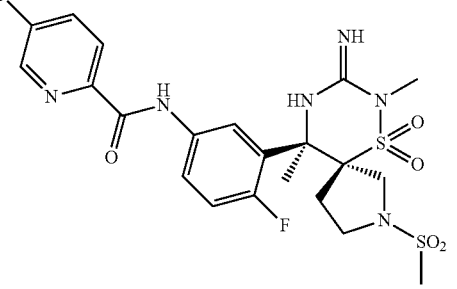 | 4 | 7 | 543.12 | 0.85 | 3 |

TABLE 13-continued
| | | BACE1 $K_i$ (nM) | BACE2 $K_i$ (nM) | LCMS data | | |
|---|---|---|---|---|---|---|
| Ex. | Structure | | | m/z | $t_R$ (min) | conditions |
| 76 | 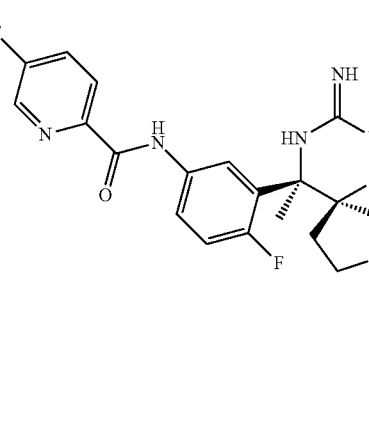 | 2 | 4 | 557.14 | 0.90 | 3 |
| 77 | 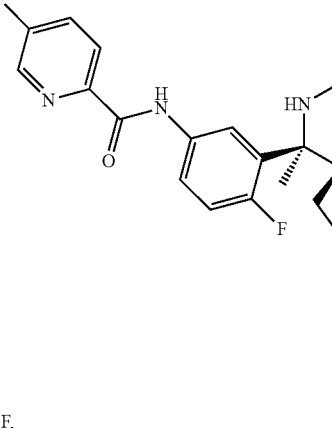 | 2 | 3 | 585.17 | 1.05 | 3 |
| 78 | 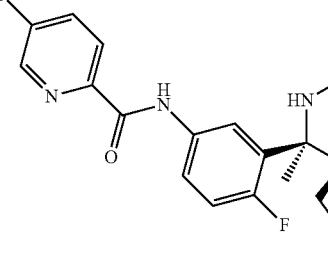 | 2 | 7 | 605.14 | 1.04 | 3 |
| 79 |  | 1 | 2 | 569.14 | 0.93 | 3 |

TABLE 13-continued

| | | BACE1 | BACE2 | LCMS data | | |
|---|---|---|---|---|---|---|
| Ex. | Structure | $K_i$ (nM) | $K_i$ (nM) | m/z | $t_R$ (min) | conditions |
| 80 | *(structure)* | 2 | 5 | 620.15 | 0.75 | 3 |
| 81 | *(structure)* | 8 | 24 | 609.14 | 0.83 | 3 |
| 82 | *(structure)* | 4 | 10 | 613.16 | 0.95 | 3 |

TABLE 13-continued
| Ex. | Structure | BACE1 $K_i$ (nM) | BACE2 $K_i$ (nM) | LCMS data m/z | $t_R$ (min) | conditions |
|---|---|---|---|---|---|---|
| 83 | | 5 | 11 | 595.13 | 0.83 | 3 |
| 84 | | 2 | 2 | 597.17 | 1.03 | 3 |
Method U
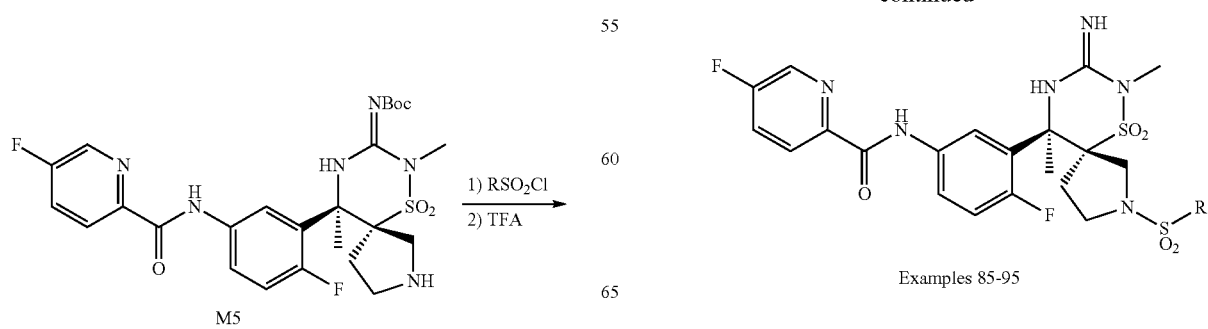
Examples 85-95

Parallel preparation of Examples 85-95: These examples were prepared from M5 and the requisite sulfonyl chlorides using a procedure similar to that described in Method R. The crude residues were purified by mass triggered HPLC using the following conditions: [column: Waters Sunfire C18, 5 µm, 19×100 mm; solvent: gradient range 10-13% initial to 32-43% final MeCN (0.1% TFA) in water (0.1% TFA) 25 mL/min; 9-12 min run time] to afford Examples 85-94. Example 95 was repurified by mass triggered HPLC using the following conditions: [column: Waters XBridge C18, 5 µm, 19×100 mm; solvent: gradient from 24% initial to 54% final MeCN (0.1% $NH_4OH$) in water (0.1% $NH_4OH$) 25 mL/min; 8 min run time] to afford Example 95.

TABLE 14

| Ex. | Structure | BACE1 $K_i$ (nM) | BACE2 $K_i$ (nM) | m/z (M + 1) | $t_R$ (min) | conditions |
|---|---|---|---|---|---|---|
| 85 | 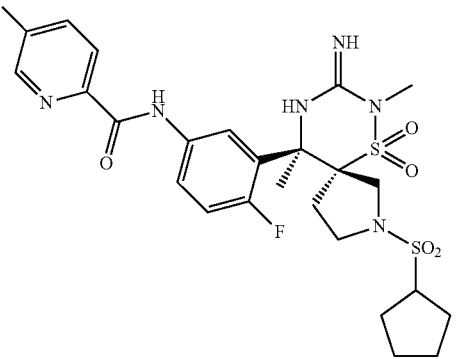 | 41 | 37 | | | |
| 86 | 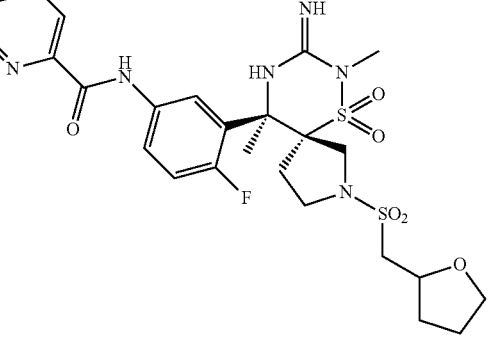 | 42 | 20 | 623.13 | 1.07 | 3 |
| 87 | 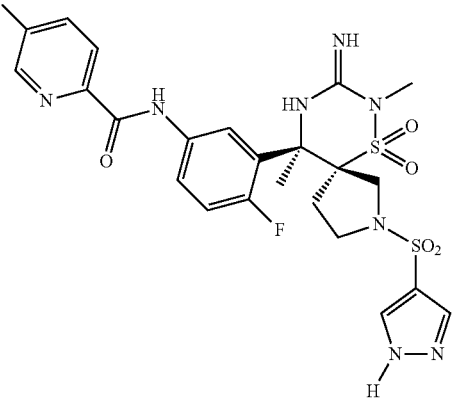 | 15 | 5 | 611.11 | 1.02 | 3 |

TABLE 14-continued

| Ex. | Structure | BACE1 $K_i$ (nM) | BACE2 $K_i$ (nM) | LCMS data m/z (M + 1) | $t_R$ (min) | conditions |
|---|---|---|---|---|---|---|
| 88 | 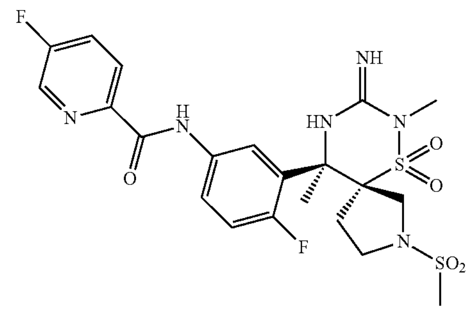 [SMILES: CN1C(=N)N[C@](C)(c2cc(NC(=O)c3ccc(F)cn3)ccc2F)[C@@]2(CCN(S(C)(=O)=O)C2)S1(=O)=O] | 34 | 54 | 543.12 | 0.85 | 3 |
| 89 | 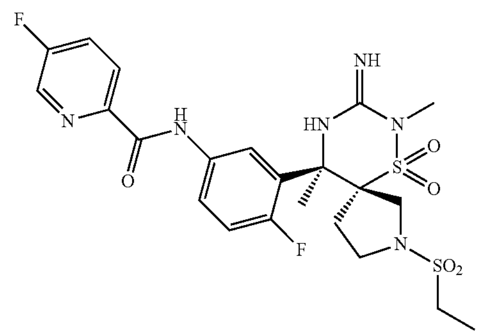 [SMILES: CCS(=O)(=O)N1CC[C@]2(C1)[C@@](C)(c1cc(NC(=O)c3ccc(F)cn3)ccc1F)NC(=N)N(C)S2(=O)=O] | 45 | 41 | 557.14 | 0.90 | 3 |
| 90 | 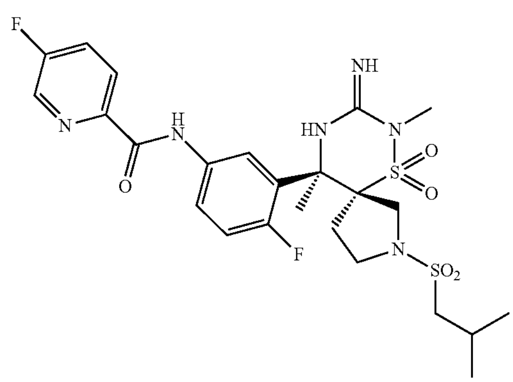 [SMILES: CC(C)CS(=O)(=O)N1CC[C@]2(C1)[C@@](C)(c1cc(NC(=O)c3ccc(F)cn3)ccc1F)NC(=N)N(C)S2(=O)=O] | 48 | 29 | 585.17 | 1.05 | 3 |
| 91 | 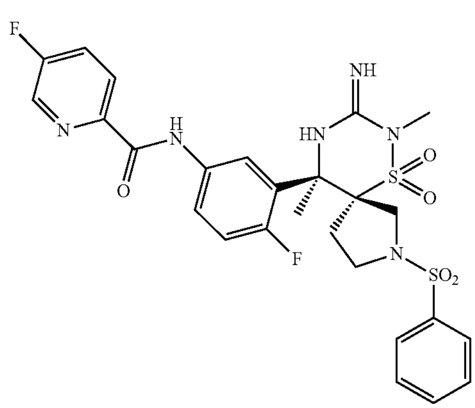 [SMILES: CN1C(=N)N[C@](C)(c2cc(NC(=O)c3ccc(F)cn3)ccc2F)[C@@]2(CCN(S(=O)(=O)c3ccccc3)C2)S1(=O)=O] | 16 | 6 | 605.14 | 1.04 | 3 |

TABLE 14-continued

| | | BACE1 | BACE2 | LCMS data | | |
|---|---|---|---|---|---|---|
| Ex. | Structure | $K_i$ (nM) | $K_i$ (nM) | m/z (M + 1) | $t_R$ (min) | conditions |
| 92 | | 41 | 29 | 569.14 | 0.93 | 3 |
| 93 | | 28 | 20 | 620.15 | 0.75 | 3 |
| 94 | | 37 | 19 | 609.14 | 0.83 | 3 |

TABLE 14-continued

| | | BACE1 | BACE2 | LCMS data | | |
|---|---|---|---|---|---|---|
| Ex. | Structure | $K_i$ (nM) | $K_i$ (nM) | m/z (M + 1) | $t_R$ (min) | conditions |
| 95 | | 25 | 6 | 613.16 | 0.95 | 3 |

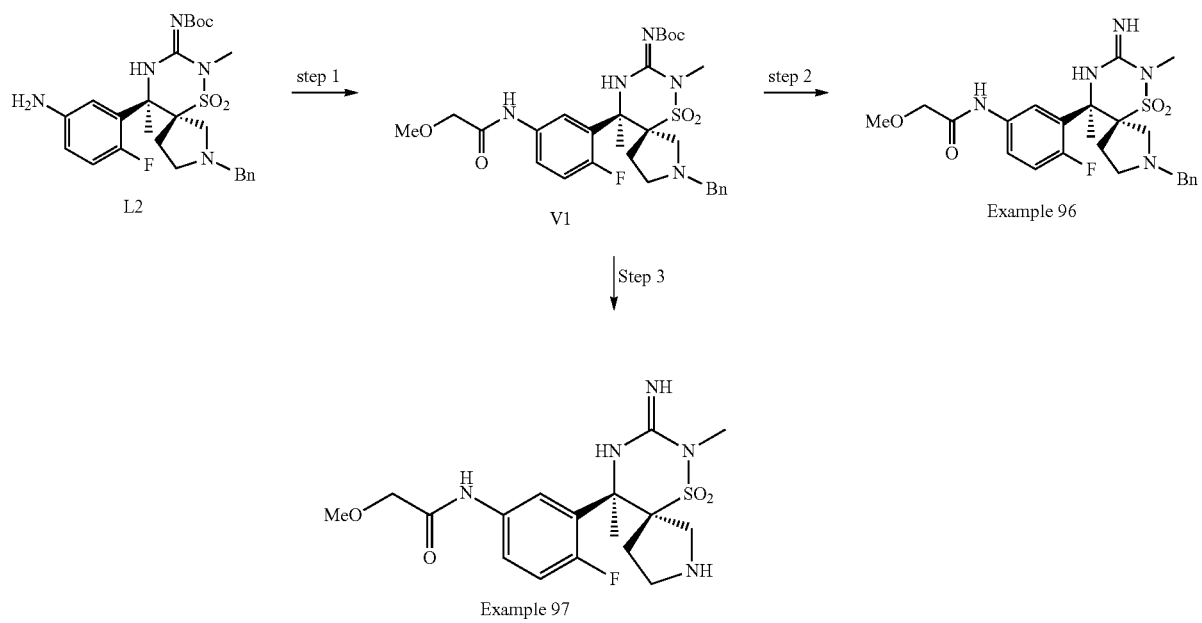

Method V:

Step 1:

Amine L2 was converted to V1 using a procedure similar to that described in Scheme M step 1. m/z=604.2 (M+H⁺).

Step 2:

To the solution of V1 (110 mg, 0.331 mmol) in dichloromethane (5 mL) at 0° C. was added 4M HCl in dioxane (10 mL) slowly. The reaction mixture was allowed to warm to RT and stir for 2 h. The reaction mixture was concentrated and the residue was purified by preparative reverse phase HPLC (Column: Symmetry Prep C18 (19×300 mm) 7 µm; column temp: ambient; mobile phase: A: 0.1% TFA in water, B: 100% acetonitrile; Gradient: From 0 to 20 min 90:10 to 50:50 (A:B), from 21-25 min 50:50 to 40:60 (A:B), from 25 to 26 mins 40:60 to 0:100(A:B), from 26-30 mins 0:100(A:B); flow rate: 15 mL/min; UV detection: 215 nm) to afford Example 96.

Step 3:

To a solution of V1 (200 mg, 0.331 mmol) in 1,2-dichloroethane (10 mL) at 0° C. was added 1-chloroethyl chloroformate (140 mg, 0.991 mmol) slowly. The reaction mixture was allowed to warm to RT and then heated at 90° C. for 3 h. Reaction mixture was then concentrated. The residue was taken in methanol and heated at 70° C. for 4 h. After that time, the reaction mixture was concentrated and the residue was purified by preparative reverse phase HPLC (see HPLC conditions described in Method V step 2) to afford Example 97.

TABLE 15

| Ex. | Structure | BACE1 $K_i$ (nM) | BACE2 $K_i$ (nM) | LCMS data m/z (M + 1) | $t_R$ (min) | conditions |
|---|---|---|---|---|---|---|
| 96 | (structure) | 22 | 25 | 504.2 | 3.16 | 4 |
| 97 | (structure) | 1037 | 782 | 414.2 | 1.81 | 5 |

LCMS Conditions:

Conditions 1:

Column: Agilent TC-C$_{18}$ (2.1×50 mm) 5 µm; Mobile phase: A: 0.0375% Trifluoroacetic acid in water, B: 0.01875% Trifluoroacetic acid in acetonitrile; Gradient: 99:1 (A:B) for 0.4 min, 99:1 to 10:90 (A:B) over 3 min, 10:90 to 0:100 (A:B) over 0.6 min; Flow rate: 0.8 mL/min; UV detection: 254 and 220 nm; Mass spectrometer: Agilent 6110 quadrupole.

Conditions 2:

Column: Agilent TC-C$_{18}$ (2.1×50 mm) 5 µm; Mobile phase: A: 0.0375% Trifluoroacetic acid in water, B: 0.01875% Trifluoroacetic acid in acetonitrile; Gradient: 100:0 (A:B) for 0.4 min, 100:0 to 20:80 (A:B) over 3 min, 20:80 to 0:100 (A:B) over 0.6 min; Flow rate: 0.6 mL/min; UV detection: 254 and 220 nm; Mass spectrometer: Agilent 6110 quadrupole.

Conditions 3:

Waters Acquity UPLC/MS, Electrospray positive ion mode; Column: Waters Acquity UPLC BEH C18, 2.1×50 mm, 1.7 micron; Gradient elution 5:95 to 100:0 MeCN (0.1% NH$_4$OH): water (0.1% NH$_4$OH) over 1.4 min 0.8 mL/min; UV: 220 nm.

Conditions 4:

Column: ZORBAX XDB-C18 (50×4.6 mm) 5.0 micron; column temp: ambient; mobile phase; A: 10 mM ammonium acetate, B: 100% acetonitrile; gradient: 0 to 3 min 90:10 to 5:95 (A:B), from 3 to 5 mins 5:95 (A:B), from 5 to 5.5 mins 5:95 to 90:10 (A:B) Flow rate: 1.2 mL/min; UV detection: 215 nm; mass spectrometer: Agilent 6130(Single)quadruple.

Conditions 5:

Column: XBRIDGE C18 (50×4.6 mm) 5.0 micron; column temp: ambient; mobile phase: A:10 mM ammonium acetate in water, B: 100% acetonitrile; gradient: 0 to 3 min 95:5 to 5:95 (A:B), from 3 to 5 min 5:95 (A:B); flow rate: 1.5 mL/min; UV detection: 215 nm; mass spectrometer: Agilent 6130(Single)quadrupole.

Assays

Protocols that used to determine the recited potency values for the compounds of the invention are described below.

BACE1 HTRF FRET Assay

Reagents:

Na$^+$-Acetate pH 5.0; 1% Brij-35; Glycerol; Dimethyl Sulfoxide (DMSO); Recombinant human soluble BACE1 catalytic domain (>95% pure); APP Swedish mutant peptide substrate (QSY7-APP$^{swe}$-Eu): QSY7-EISEVNLDAEFC-Europium-amide.

A homogeneous time-resolved FRET assay can be used to determine IC$_{50}$ values for inhibitors of the soluble human BACE1 catalytic domain. This assay monitors the increase of 620 nm fluorescence that resulted from BACE1 cleavage of an APPswedish APP$^{swe}$ mutant peptide FRET substrate (QSY7-EISEVNLDAEFC-Europium-amide). This substrate contains an N-terminal QSY7 moiety that serves as a quencher of the C-terminal Europium fluorophore (620 nm Em). In the absence of enzyme activity, 620 nm fluorescence is low in the assay and increased linearly over 3 hours in the presence of uninhibited BACE1 enzyme. Inhibition of BACE cleavage of the QSY7-APP$^{swe}$-Eu substrate by inhibitors is manifested as a suppression of 620 nm fluorescence.

Varying concentrations of inhibitors at 3× the final desired concentration in a volume of 10 ul are preincubated with purified human BACE1 catalytic domain (3 nM in 10 µl) for 30 minutes at 30° C. in reaction buffer containing 20 mM Na-Acetate pH 5.0, 10% glycerol, 0.1% Brij-35 and 7.5% DSMO. Reactions are initiated by addition of 10 µl of 600 nM QSY7-APP$^{swe}$-Eu substrate (200 nM final) to give a final reaction volume of 30 µl in a 384 well Nunc HTRF plate. The reactions are incubated at 30° C. for 1.5 hours. The 620 nm fluorescence is then read on a Rubystar HTRF plate reader (BMG Labtechnologies) using a 50 millisecond delay followed by a 400 millisecond acquisition time window. Inhibitor IC$_{50}$ values are derived from non-linear regression analysis of concentration response curves. K$_i$ values are then calculated from IC$_{50}$ values using the Cheng- Prusoff equation using a previously determined μm value of 8 μM for the QSY7-APP$^{swe}$-Eu substrate at BACE1.

BACE-2 Assay

Inhibitor IC$_{50}$'s at purified human autoBACE-2 are determined in a time-resolved endpoint proteolysis assay that measures hydrolysis of the QSY7-EISEV NLDAEFC-Eu-amide FRET peptide substrate (BACE-HTRF assay). BACE-mediated hydrolysis of this peptide results in an increase in relative fluorescence (RFU) at 620 nm after excitation with 320 nm light. Inhibitor compounds, prepared at 3× the desired final concentration in 1×BACE assay buffer (20 mM sodium acetate pH 5.0, 10% glycerol, 0.1% Brij-35) supplemented with 7.5% DMSO are pre-incubated with an equal volume of autoBACE-2 enzyme diluted in 1×BACE assay buffer (final enzyme concentration 1 nM) in black 384-well NUNC plates for 30 minutes at 30° C. The assay is initiated by addition of an equal volume of the QSY7-EISEVNLDAEFC-Eu-amide substrate (200 nM final concentration, K$_m$=8 μM for 4 μM for autoBACE-2) prepared in 1×BACE assay buffer supplemented with 7.5% DMSO and incubated for 90 minutes at 30° C. DMSO is present at 5% final concentration in the assay. Following laser excitation of sample wells at 320 nm, the fluorescence signal at 620 nm is collected for 400 ms following a 50 μs delay on a RUBYstar HTRF plate reader (BMG Labtechnologies). Raw RFU data is normalized to maximum (1.0 nM BACE/DMSO) and minimum (no enzyme/DMSO) RFU values. IC$_{50s}$ are determined by nonlinear regression analysis (sigmoidal dose response, variable slope) of percent inhibition data with minimum and maximum values set to 0 and 100 percent respectively. Similar IC$_{50s}$ are obtained when using raw RFU data. The K$_i$ values are calculated from the IC$_{50}$ using the Cheng-Prusoff equation.

What is claimed is:

1. A compound, or a pharmaceutically acceptable salt thereof, said compound having the structural Formula (I):

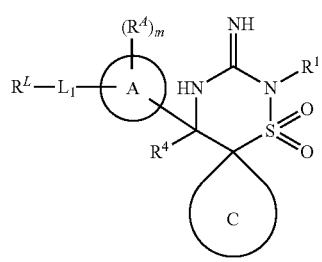

or a tautomer thereof having the structural Formula (I'):

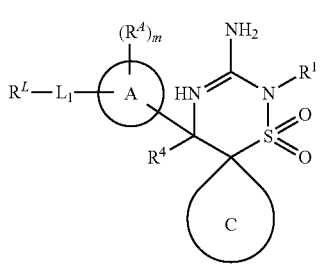

or pharmaceutically acceptable salt of said tautomer, wherein:

R$^1$ is selected from the group consisting of H, alkyl, heteroalkyl, cycloalkyl, and -alkyl-cycloalkyl, wherein each said alkyl, heteroalkyl, cycloalkyl, and -alkyl-cycloalkyl is optionally substituted with one or more halogen;

ring C is a moiety selected from the group consisting of

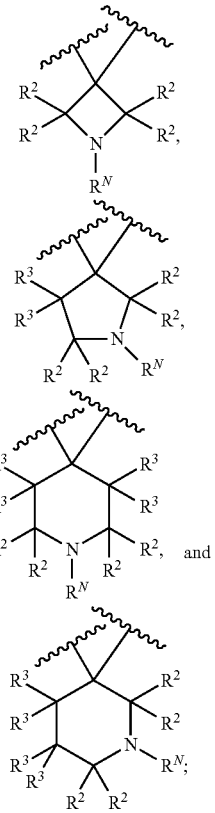

each R$^2$ is independently selected from the group consisting of H, -alkyl-OH, alkyl, heteroalkyl, and cycloalkyl wherein each said alkyl, heteroalkyl, and cycloalkyl of R$^2$ is optionally substituted with halogen;

each R$^3$ is independently selected from the group consisting of H, halogen, -alkyl-OH, alkyl, heteroalkyl, alkoxy, and cycloalkyl, wherein each said alkyl, heteroalkyl, alkoxy, and cycloalkyl of R$^3$ is optionally substituted with halogen;

R$^N$ is selected from the group consisting of: H, —C(O)R$^{6N}$, —C(O)OR$^{6N}$, —C(O)N(R$^{6N}$)$_2$, —S(O)$_2$R$^{6N}$, —S(O)$_2$N(R$^{6N}$)$_2$, alkyl, heteroalkyl, cycloalkyl, -alkyl-cycloalkyl, heterocycloalkyl, -alkyl-heterocycloalkyl, aryl, -alkyl-aryl, heteroaryl, and -alkyl-heteroaryl, wherein said alkyl, heteroalkyl, cycloalkyl, -alkyl-cycloalkyl, heterocycloalkyl, -alkyl-heterocycloalkyl, aryl, -alkyl-aryl, heteroaryl, and -alkyl-heteroaryl, of R$^N$ are each optionally independently unsubstituted or substituted with one or more groups independently selected from R$^9$;

R$^4$ is selected from the group consisting of H, alkyl, heteroalkyl, cycloalkyl, -alkyl-cycloalkyl, heterocycloalkyl, and -alkyl-heterocycloalkyl, wherein each said alkyl, heteroalkyl, cycloalkyl, -alkyl-cycloalkyl, heterocycloalkyl, and -alkyl-heterocycloalkyl is optionally substituted with one or more halogen;

ring A is selected from the group consisting of aryl and heteroaryl;

m is 0 or more;

each $R^A$ (when present) is independently selected from the group consisting of: halogen, oxo, —OH, —CN, —SF$_5$, —OSF$_5$, —Si(R$^{5A}$)$_3$, —N(R$^{6A}$)$_2$, —OR$^{6A}$, —SR$^{6A}$, alkyl, heteroalkyl, alkenyl, alkynyl, cycloalkyl, -alkyl-cycloalkyl, heterocycloalkyl, and -alkyl-heterocycloalkyl, wherein said alkyl, heteroalkyl, alkenyl, alkynyl, cycloalkyl, -alkyl-cycloalkyl, heterocycloalkyl, and -alkyl-heterocycloalkyl of $R^A$ are each optionally independently unsubstituted or substituted with one or more groups independently selected from $R^8$;

-L$_1$- is a divalent moiety selected from the group consisting of —NHC(O)— and —C(O)NH—;

$R^L$ is selected from the group consisting of alkyl and heteroalkyl, wherein said alkyl and heteroalkyl of $R^L$ are each optionally unsubstituted or substituted with one or more halogen;

or, alternatively, $R^L$ is a moiety having the formula

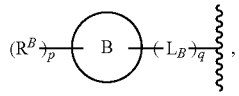

wherein q is 0 or 1;

-L$_B$- (when present) is a divalent moiety selected from the group consisting of lower alkyl and lower heteroalkyl, wherein each said lower alkyl and lower heteroalkyl is optionally substituted with one or more halogen;

ring B is selected from the group consisting of aryl, heteroaryl, cycloalkyl, cycloalkenyl, heterocycloalkyl, and heterocycloalkenyl;

p is 0 or more; and each $R^B$ (when present) is independently selected from the group consisting of: halogen, oxo, —OH, —CN, —SF$_5$, —OSF$_5$, —Si(R$^{5B}$)$_3$, —N(R$^{6B}$)$_2$, —NR$^{7B}$C(O)R$^{6B}$, —NR$^{7B}$S(O)$_2$R$^{6B}$, —NR$^{7B}$S(O)$_2$N(R$^{6B}$)$_2$, —NR$^{7B}$C(O)N(R$^{6B}$)$_2$, —NR$^{7B}$C(O)OR$^{6B}$, —C(O)R$^{6B}$, —C(O)OR$^{6B}$, —C(O)N(R$^{6B}$)$_2$, —S(O)R$^{6B}$, —S(O)$_2$R$^{6B}$, —S(O)$_2$N(R$^{6B}$)$_2$, —OR$^{6B}$, —SR$^{6B}$, alkyl, heteroalkyl, alkenyl, alkynyl, cycloalkyl, -alkyl-cycloalkyl, heterocycloalkyl, -alkyl-heterocycloalkyl, aryl, -alkyl-aryl, heteroaryl, and -alkyl-heteroaryl, wherein said alkyl, heteroalkyl, alkenyl, alkynyl, cycloalkyl, -alkyl-cycloalkyl, heterocycloalkyl, -alkyl-heterocycloalkyl, aryl, -alkyl-aryl, heteroaryl, and -alkyl-heteroaryl, of $R^B$ are each optionally independently unsubstituted or substituted with one or more groups independently selected from $R^9$;

each $R^{5A}$ and $R^{5B}$ (when present) is independently selected from the group consisting of alkyl, heteroalkyl, cycloalkyl, -alkyl-cycloalkyl, heterocycloalkyl, -alkyl-heterocycloalkyl, wherein each said alkyl, heteroalkyl, cycloalkyl, -alkyl-cycloalkyl, heterocycloalkyl, -alkyl-heterocycloalkyl of $R^{5A}$ and $R^{5B}$ is unsubstituted or substituted with one or more halogen;

each $R^{6N}$ and $R^{6A}$ (when present) is independently selected from the group consisting of H, alkyl, -alkyl-OH, alkenyl, alkynyl, heteroalkyl, -heteroalkyl-OH, cycloalkyl, -alkyl-cycloalkyl, heterocycloalkyl, -alkyl-heterocycloalkyl, aryl, heteroaryl, -alkyl-aryl, and -alkyl-heteroaryl, wherein each said alkyl, -alkyl-OH, alkenyl, alkynyl, heteroalkyl, -heteroalkyl-OH, cycloalkyl, -alkyl-cycloalkyl, heterocycloalkyl, -alkyl-heterocycloalkyl, aryl, -alkyl-aryl, heteroaryl, and -alkyl-heteroaryl of $R^{6N}$ and $R^{6A}$ is unsubstituted or substituted with one or more groups independently selected from halogen, alkyl, cycloalkyl, heteroalkyl, haloalkyl, alkoxy, heteroalkoxy, and haloalkoxy;

each $R^{6B}$ (when present) is independently selected from the group consisting of H, alkyl, -alkyl-OH, alkenyl, alkynyl, heteroalkyl, -heteroalkyl-OH, cycloalkyl, -alkyl-cycloalkyl, heterocycloalkyl, -alkyl-heterocycloalkyl, aryl, -alkyl-aryl, heteroaryl, and -alkyl-heteroaryl, wherein each said alkyl, -alkyl-OH, alkenyl, alkynyl, heteroalkyl, -heteroalkyl-OH, cycloalkyl, -alkyl-cycloalkyl, heterocycloalkyl, -alkyl-heterocycloalkyl, aryl, -alkyl-aryl, heteroaryl, and -alkyl-heteroaryl of $R^{6B}$ is unsubstituted or substituted with one or more groups independently selected from halogen, alkyl, cycloalkyl, heteroalkyl, haloalkyl, alkoxy, heteroalkoxy, and haloalkoxy;

each $R^{7B}$ (when present) is independently selected from the group consisting of H, alkyl, heteroalkyl, cycloalkyl, -alkyl-cycloalkyl, heterocycloalkyl, and -alkyl-heterocycloalkyl, wherein each said alkyl, heteroalkyl, -heteroalkyl-OH, cycloalkyl, -alkyl-cycloalkyl, heterocycloalkyl, and -alkyl-heterocycloalkyl of $R^{7B}$ is unsubstituted or substituted with one or more halogen;

each $R^8$ (when present) is independently selected from the group consisting of halogen, lower alkyl, lower heteroalkyl, lower alkoxy, lower cycloalkyl, and lower heterocycloalkyl, wherein each said lower alkyl, lower heteroalkyl, lower alkoxy, lower cycloalkyl, and lower heterocycloalkyl of $R^8$ is optionally substituted with halogen; and each $R^9$ (when present) is independently selected from the group consisting of halogen, —OH, —CN, —SF$_5$, —OSF$_5$, alkyl, -alkyl-OH, heteroalkyl, -heteroalkyl-OH, alkoxy, —O-heteroalkyl, cycloalkyl, -alkyl-cycloalkyl, —O-cycloalkyl, —O-alkyl-cycloalkyl, -heterocycloalkyl, -alkyl-heterocycloalkyl, —O-heterocycloalkyl and —O-alkyl-heterocycloalkyl, wherein each said alkyl, -alkyl-OH, heteroalkyl, -heteroalkyl-OH, alkoxy, —O-heteroalkyl, cycloalkyl, -alkyl-cycloalkyl, —O-cycloalkyl, —O-alkyl-cycloalkyl, -heterocycloalkyl, -alkyl-heterocycloalkyl, —O-heterocycloalkyl and —O-alkyl-heterocycloalkyl are optionally substituted with one or more halogen.

2. A compound of claim 1, or a tautomer thereof, or a pharmaceutically acceptable salt of said compound or said tautomer, wherein:

ring C is:

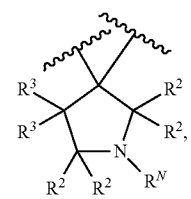

wherein each $R^N$ group is selected from the group consisting of H, —C(O) CH$_3$, —C(O)CH$_2$CH$_3$, —C(O)

CH₂CH(CH₃)₂, —C(O)-cyclopropyl, —C(O)—CH₂-cyclopropyl, —C(O)N(CH₃)₂, —C(O)NHCH₃, —S(O)₂CH₃, —S(O)₂CH₂CH₃, —S(O)₂CH₂CF₃, —S(O)₂CH₂CH(CH₃)₂, —S(O)₂-phenyl, —S(O)₂CH₂-pyridyl, —S(O)₂-cyclopentyl, —S(O)₂-cyclopropyl, —S(O)₂-imidazolyl, —S(O)₂—CH₂-tetrahydrofuranyl, —S(O)₂-pyrazolyl, —S(O)₂N(CH₃)₂, —S(O)₂NHCH₃, methyl, ethyl, propyl, cyclopropyl, butyl, —CH₂-cyclopropyl, benzyl, —CH₂OCH₃, —CH₂OCH₂CH₃, phenyl, pyridyl, pyrimidinyl, pyrazinyl, oxadiazolyl, isoxazolyl, oxazolyl, and pyrrolyl, —CH₂-thiazolyl, —CH₂— oxazoyl, —CH₂-pyridyl, —CH₂-pyrimidinyl, —CH₂-pyrazinyl, —CH₂-pyrazolyl, —CH₂-cyclobutyl, —CH₂-cyclopropyl, —CH₂-tetrahydrofuranyl, wherein said benzyl, cyclobutyl, phenyl, pyridyl, oxadiazolyl, imidazolyl, isoxazolyl, oxazolyl, and pyrrolyl are each optionally unsubstituted or substituted with fluorine, chlorine, methyl, —CN, —CF₃, CHF₂, and —OMe;

$R^1$ is methyl;

each $R^2$ is H;

each $R^3$ is independently selected from the group consisting of H and fluorine; and $R^4$ is selected from the group consisting of methyl and —CHF₂.

3. A compound of claim 2, or a tautomer thereof, or a pharmaceutically acceptable salt of said compound or said tautomer, wherein:

ring A is selected from the group consisting of phenyl, pyridazinyl, pyridyl, pyrimidinyl, pyrazinyl, triazinyl, and tetrazinyl;

m is 0, 1, or 2; and each $R^A$ (when present) is independently selected from the group consisting of halogen, oxo, —CN, —SF₅, —NHCH₃, —N(CH₃)₂, —OCH₃, —OCH₂CH₃, —O-cyclopropyl, —O—CH₂-cyclopropyl, —CH₂OCH₃, —S(CH₃), methyl, ethyl, cyclopropyl, —CH₂-cyclopropyl, —CF₃, —CHF₂, —CH₂F, —OCF₃, and —OCHF₂.

4. A compound of claim 3, or a tautomer thereof, or a pharmaceutically acceptable salt of said compound or said tautomer, wherein:

$R^L$ is selected from the group consisting of methyl, ethyl, propyl, butyl, —CF₃, —CHF₂, —CH₂CF₃, —CF₂CH₃, —CH₂OCH₃, —CH₂OCH₂CH₃, —CH₂CH₂OCH₃, —CH₂SCH₃, —CH₂SCH₂CH₃, —CH₂CH₂SCH₃, —CH₂N(CH₃)₂, —CH₂NHCH₃, —CH₂CH₂N(CH₃)₂, —CH₂OCF₃, and —CH₂OCHF₂.

5. A compound of claim 3, or a tautomer thereof, or a pharmaceutically acceptable salt of said compound or said tautomer, wherein:

$R^L$ is a moiety having the formula

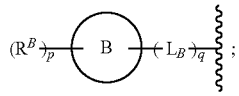

q is 0 or 1;

-$L_B$- (when present) is a divalent moiety selected from the group consisting of —CH₂—, —CF₂—, —CH₂CH₂—, —CH₂O—, and —CF₂O—;

ring B is selected from the group consisting of azetidinyl, benzimidazolyl, benzoisothiazolyl, benzoisoxazolyl, benzothiazolyl, benzoxazoyl, cyclobutyl, cyclohexyl, cyclopentyl, cyclopropyl, dihydroindenyl, dihydrooxazolyl, furanyl, imidazolyl, imidazopyridinyl, imidazopyrimidinyl, indenyl, indolyl, isothiazolyl, isoxazolyl, morpholinyl, oxadiazolyl, oxazolyl, oxetanyl, phenyl, piperazinyl, piperidinyl, pyrazinyl, pyrazolyl, pyrazolopyridinyl, pyrazolopyrimidinyl, pyridazinyl, pyridyl, pyrimidinyl, pyrazolopyridinyl, pyrrolidinyl, pyrrolyl, pyrrolopyridinyl, pyrrolopyrimidinyl, tetrahydrofuranyl, tetrahydropyranyl, tetrazolyl, thiadiazolyl, thiazolyl, thienyl, thienylpyridine, thiomorpholinyl, thiomorpholinyl dioxide, and triazolyl;

p is 0 or more; and each $R^B$ group (when present) is independently selected from the group consisting of halogen, oxo, —OH, —CN, —SF₅, —NH₂, —NH(CH₃), —N(CH₃)₂, —NHC(O)CH₃, —N(CH₃)C(O)CH₃, —NHS(O)₂CH₃, —N(CH₃)S(O)₂CH₃, —C(O)OCH₃, —C(O)OCH₂CH₃, —C(O)N(CH₃)₂, —C(O)NHCH₃, —S(O)₂CH₃, —S(O)₂N(CH₃)₂, —S(O)₂NHCH₃, —OCH₃, —OCH₂CH₃, —O-cyclopropyl, —O—CH₂-cyclopropyl, —OCH₂—C≡C—H, —OCH₂—C≡C—CH₃, —S(CH₃), methyl, ethyl, propyl, cyclopropyl, —CH₂-cyclopropyl, —CH₂OCH₃, —CH₂OCH₂CH₃, —C≡CH, —C≡C—CH₃, —CF₃, —CHF₂, —CH₂F, —OCF₃, —OCH₂CF₃, —OCHF₂, —OCH₂F, —OCH₂CH₂F, phenyl, pyridyl, oxadiazoyl, isoxazoyl, oxazoyl, and pyrrolyl, wherein each said phenyl, pyridyl, oxadiazoyl, isoxazoyl, oxazoyl, and pyrrolyl is optionally substituted with from 1 to 3 substituents independently selected from the group consisting of F, Cl, CN, —CH₃, —OCH₃, and —CF₃.

6. A compound of claim 5, or a tautomer thereof, or a pharmaceutically acceptable salt of said compound or said tautomer, wherein:

$R^L$ is a moiety having the formula

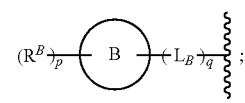

q is 0 or 1;

-$L_B$- (when present) is a divalent moiety selected from the group consisting of —CH₂—, —CF₂—, —CH₂CH₂—, —CH₂O—, and —CF₂O—;

ring B is selected from the group consisting of isoxazoyl, oxadiazoyl, oxazolyl, phenyl, pyridinyl, pyrazinyl, pyrimidinyl, and pyrazolyl;

p is 0 or more; and each $R^B$ group (when present) is independently selected from the group consisting of fluoro, chloro, —CN, —S(O)₂CH₃, —OCH₃, —O-cyclopropyl, —O—CH₂-cyclopropyl, —OCH₂—C≡C—H, —OCH₂—C≡C—CH₃, methyl, cyclopropyl, —CH₂-cyclopropyl, —CH₂OCH₃, —C≡C—CH₃, —CF₃, —CHF₂, —CH₂F, —OCF₃, —OCHF₂, —OCH₂F, and —OCH₂CH₂F.

7. A compound of claim 6, or a tautomer thereof, or a pharmaceutically acceptable salt of said compound or said tautomer, wherein:

q is 0; and $R^L$ is a moiety having the formula

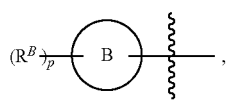

wherein:
   ring B is selected from the group consisting of isoxazoyl, oxadiazoyl, oxazolyl, phenyl, pyridinyl, pyrazinyl, pyrimidinyl, and pyrazolyl;
   p is 0 or more; and
   each $R^B$ group (when present) is independently selected from the group consisting of fluoro, chloro, bromo, —CN, —S(O)$_2$CH$_3$, —OCH$_3$, —O-cyclopropyl, —O—CH$_2$-cyclopropyl, —OCH$_2$—C≡C—H, —OCH$_2$—C≡C—CH$_3$, methyl, cyclopropyl, —CH$_2$-cyclopropyl, —CH$_2$OCH$_3$, —C≡C—CH$_3$, —CF$_3$, —CHF$_2$, —CH$_2$F, —OCF$_3$, —OCHF$_2$, —OCH$_2$F, and —OCH$_2$CH$_2$F.

8. A compound of claim 1, or a tautomer thereof, or a pharmaceutically acceptable salt of said compound or said tautomer, said compound selected from the group consisting of:

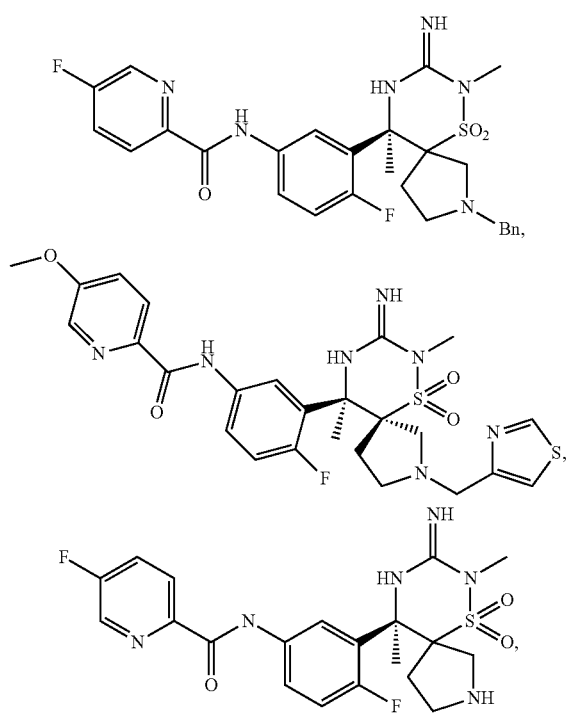

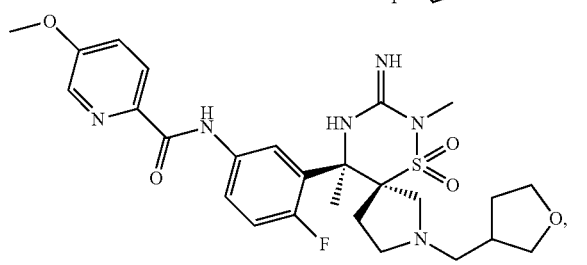

113
-continued
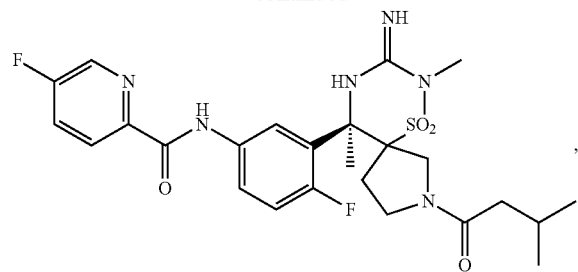
,
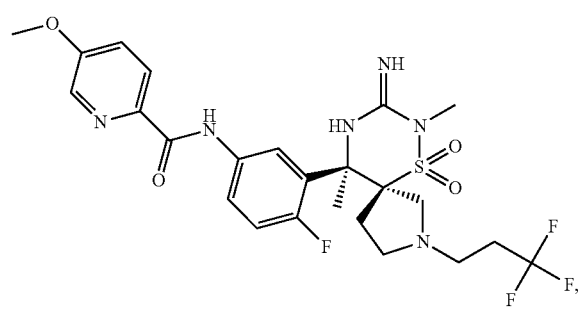
,
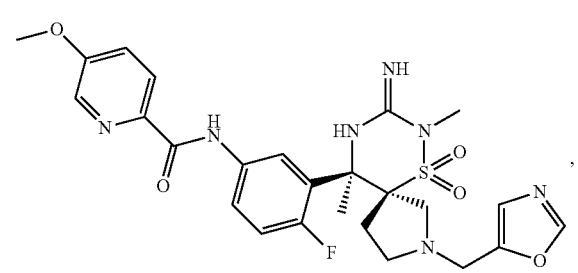
,
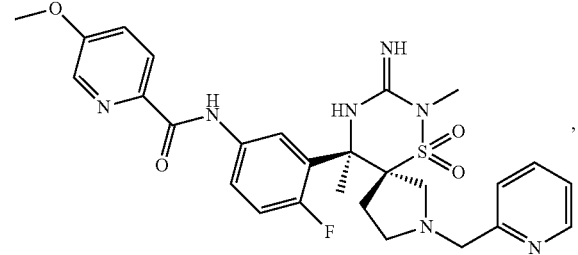
,
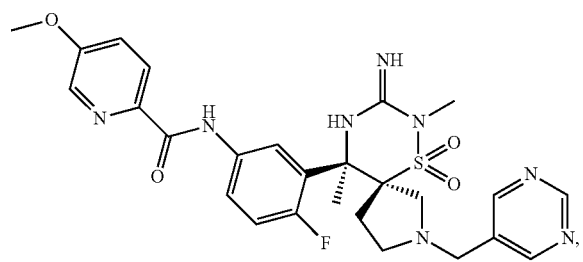
,
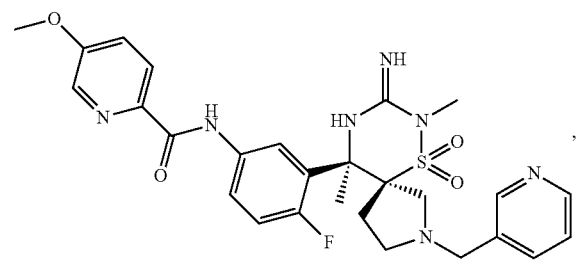
,
114
-continued
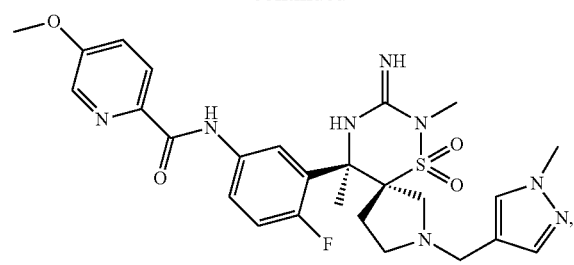
,
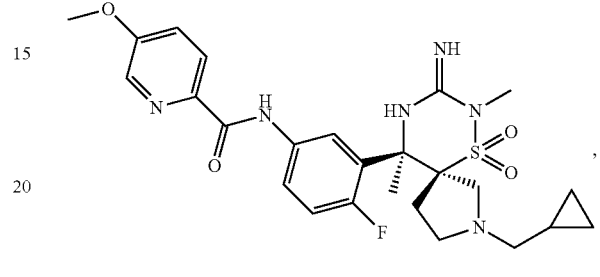
,
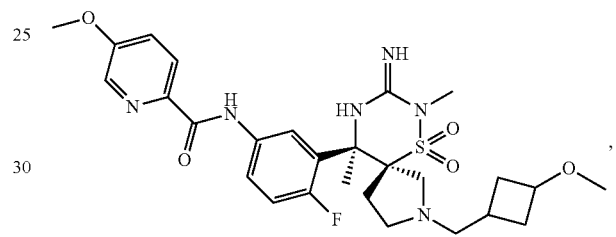
,
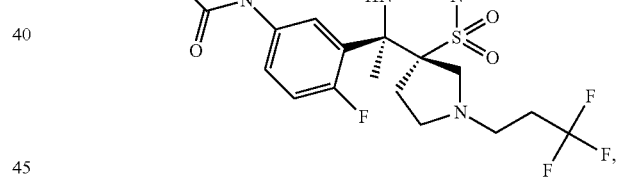
,
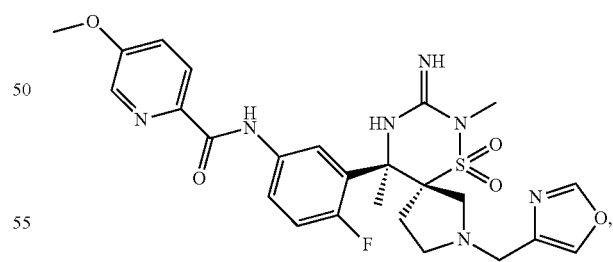
,
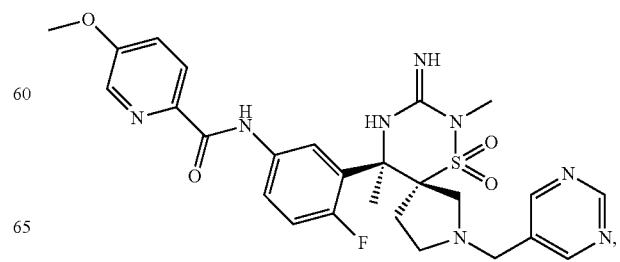
, 115
-continued
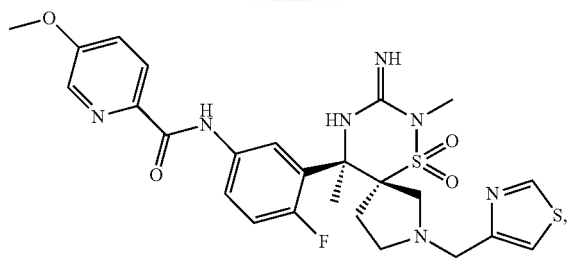
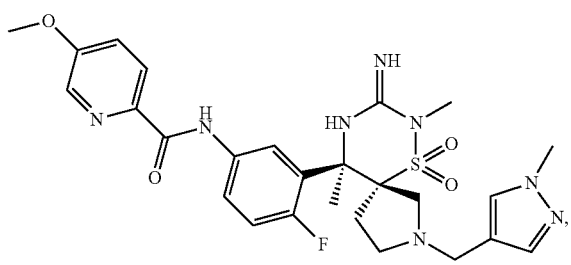
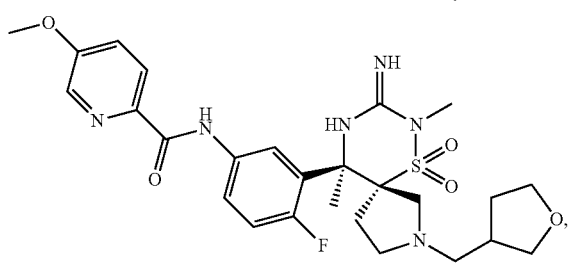
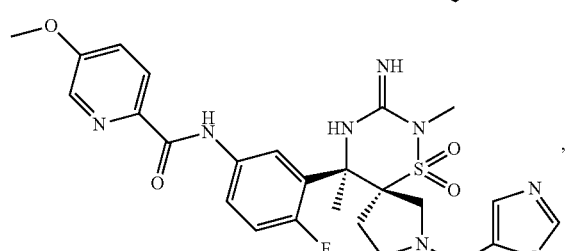
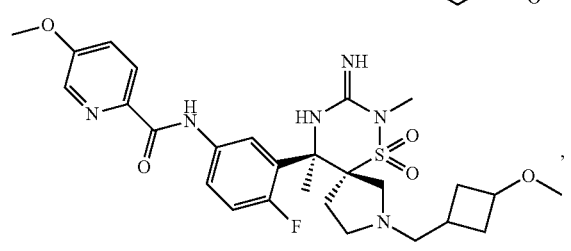
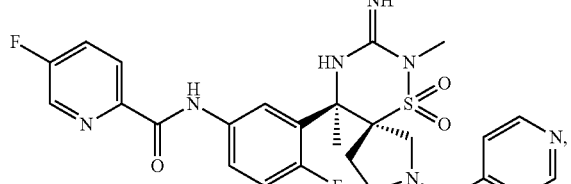
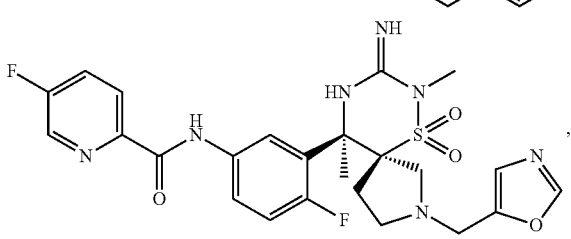
116
-continued
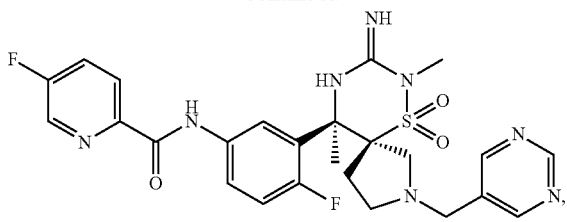
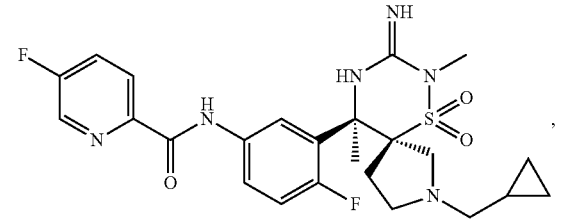
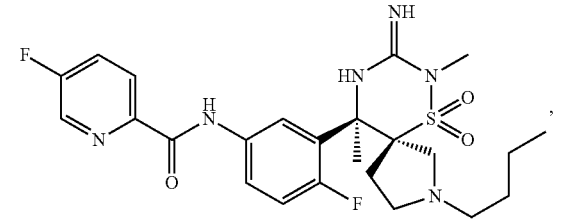
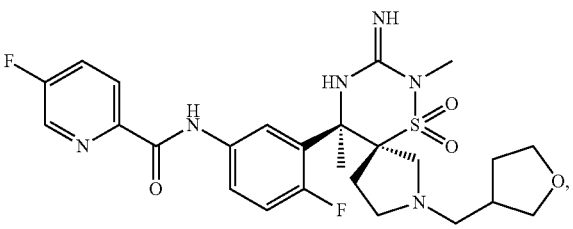
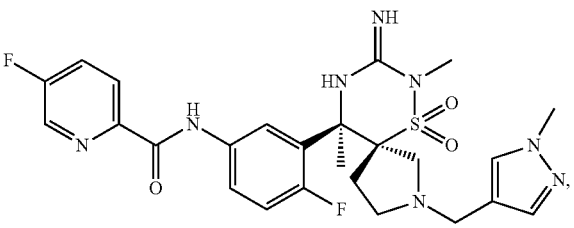
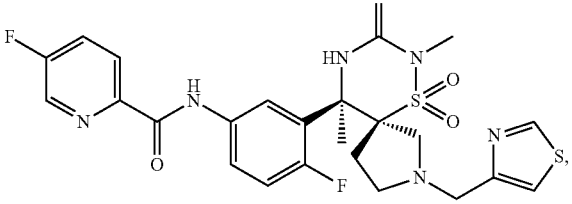
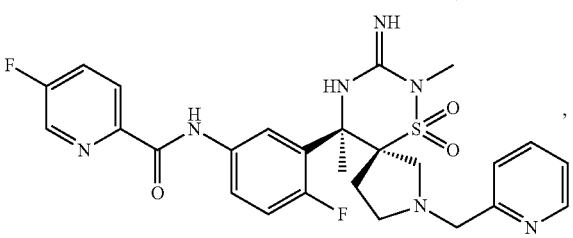

117
-continued
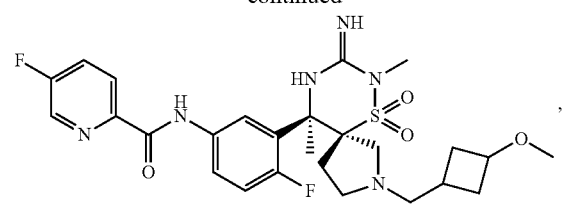,
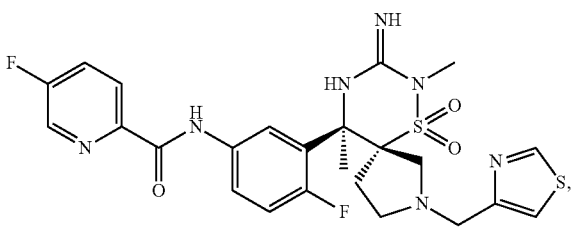,
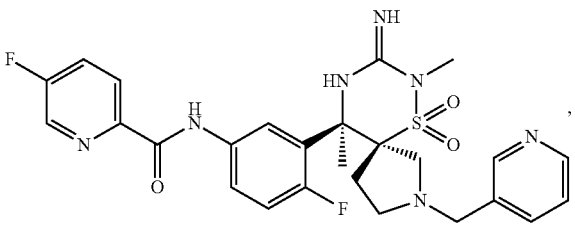,
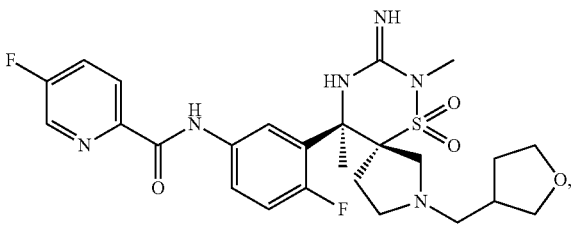,
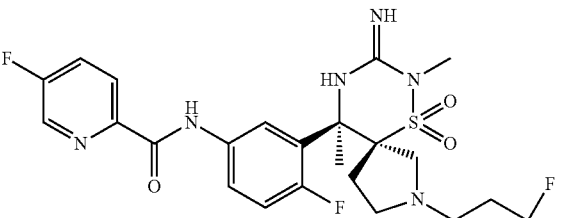,
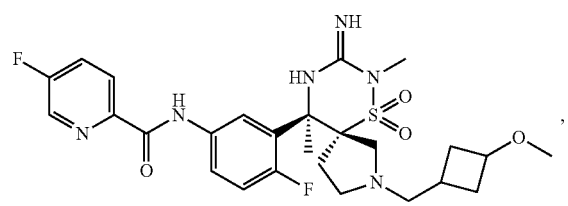,
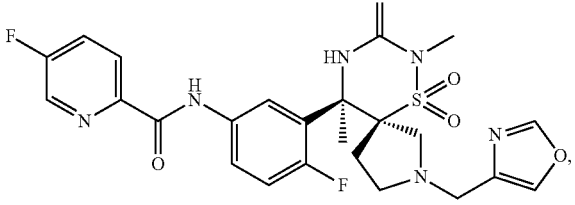,
118
-continued
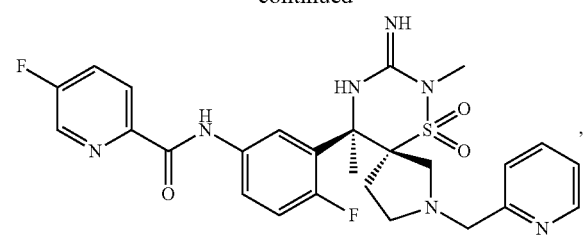,
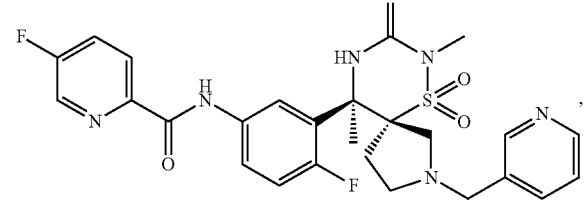,
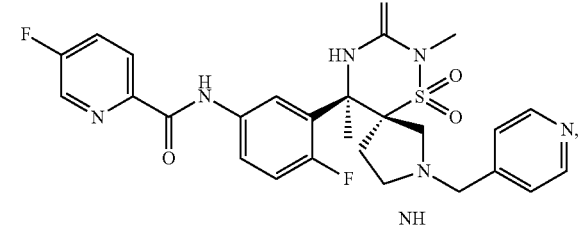,
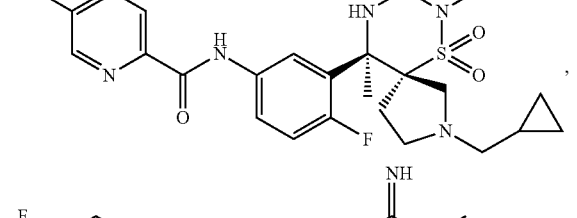,
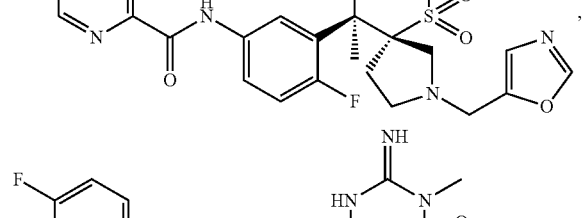,
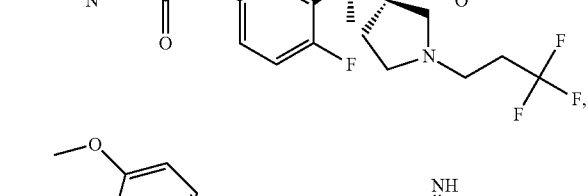,
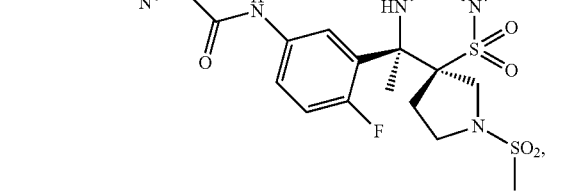, 119
-continued
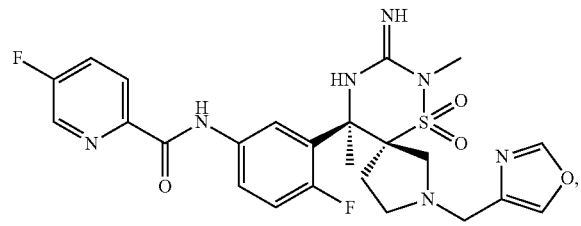
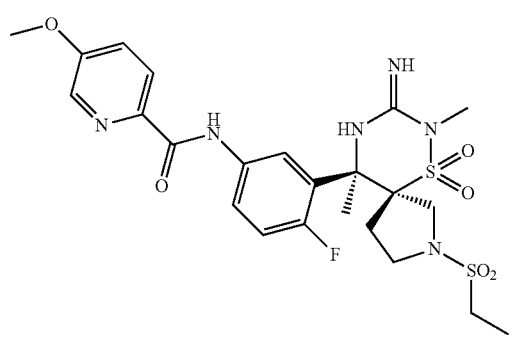
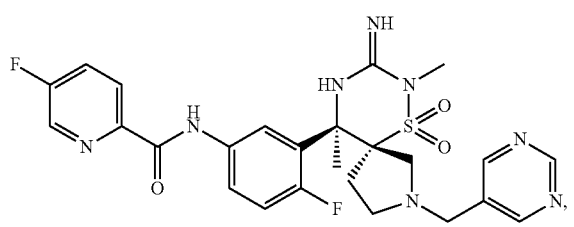
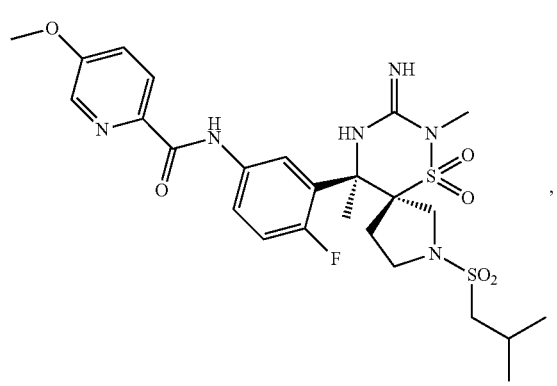
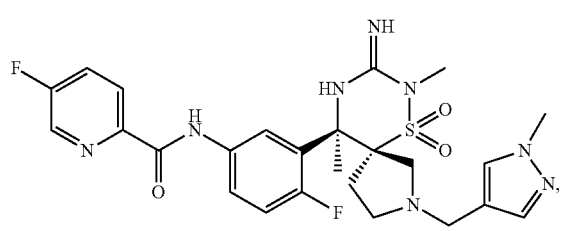
120
-continued
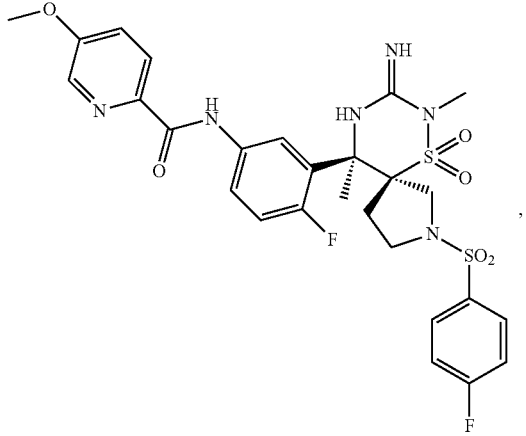
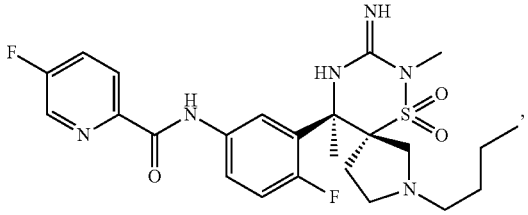
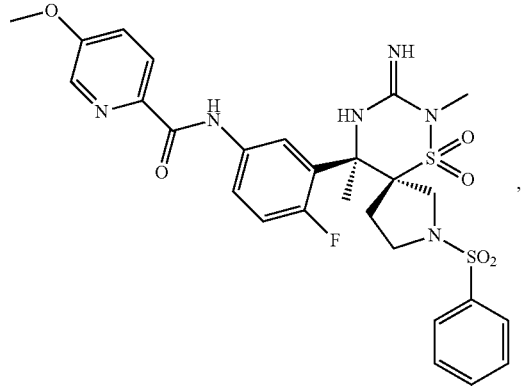
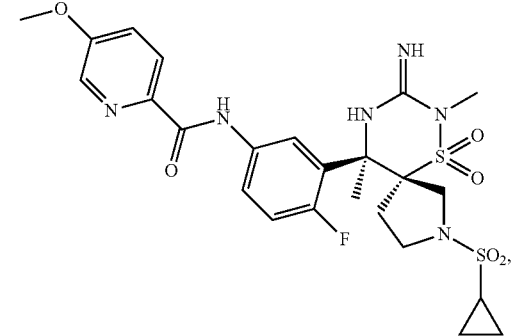
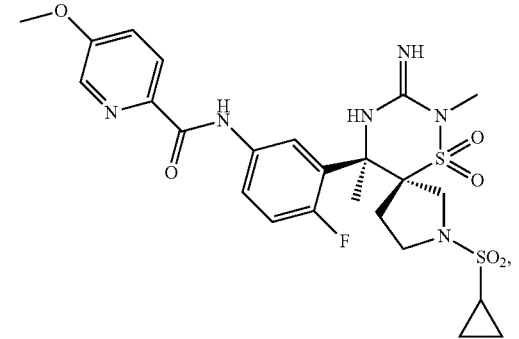

121
-continued
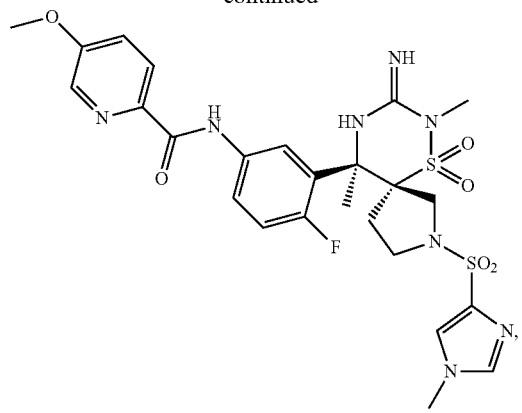
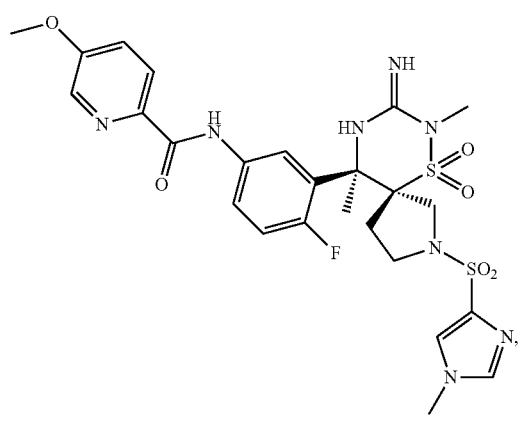
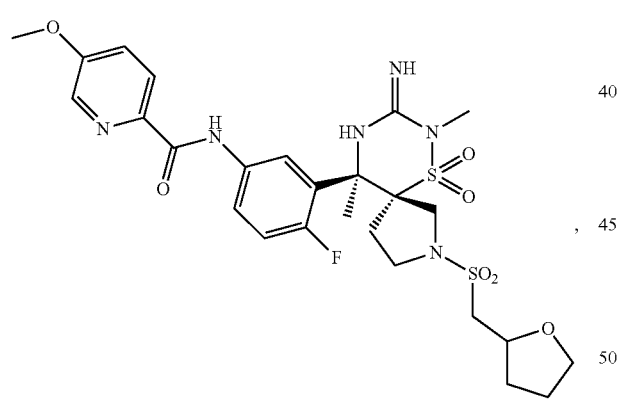
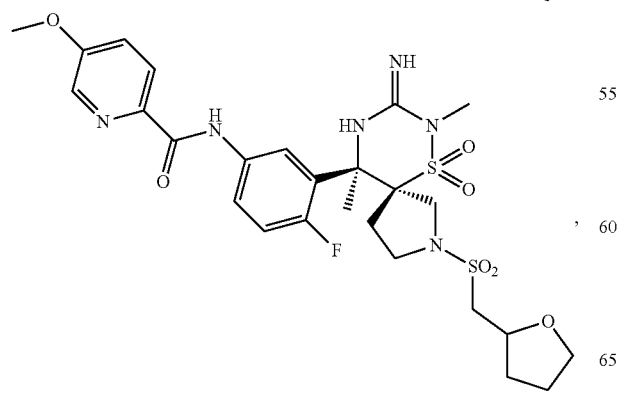
122
-continued
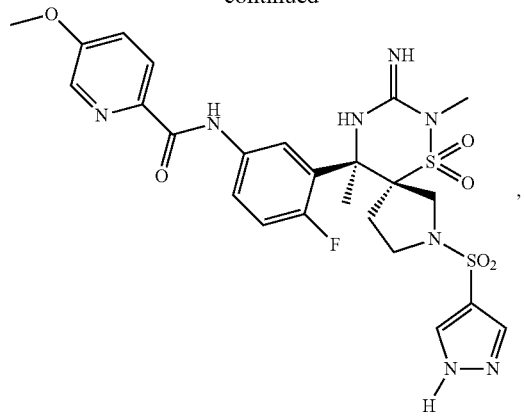
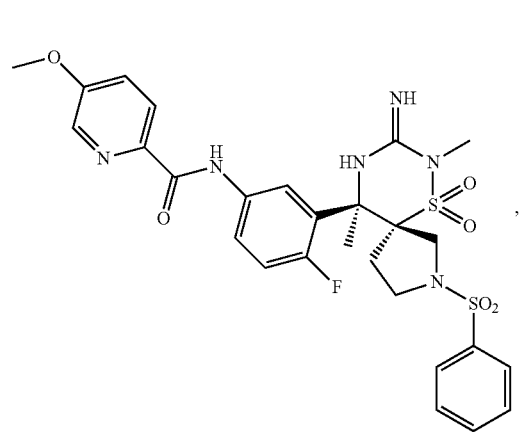
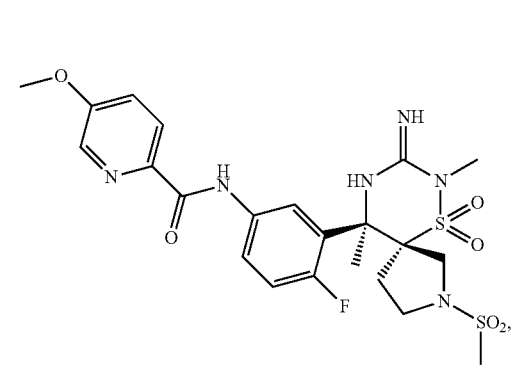
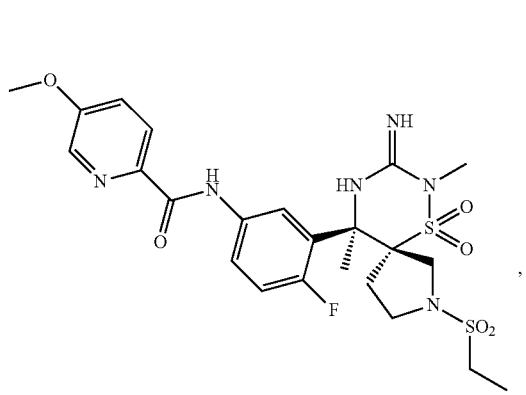

123
-continued
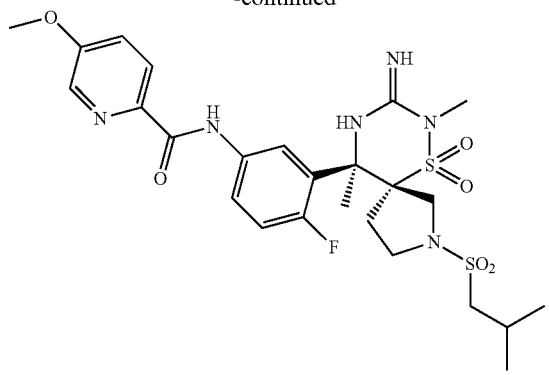
,
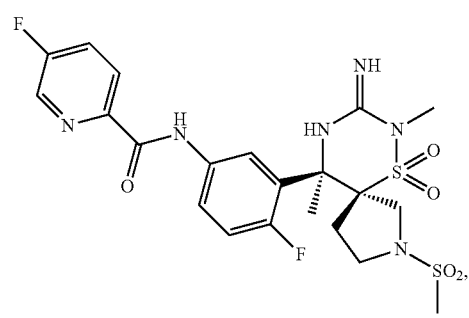
,
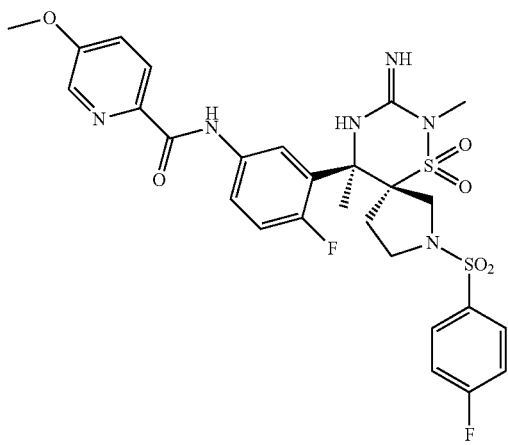
,
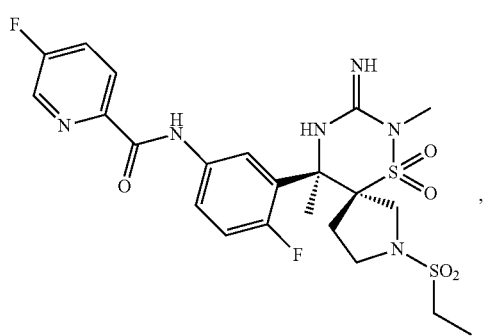
,
124
-continued
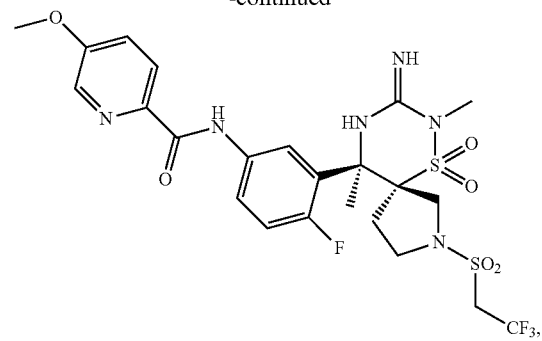
,
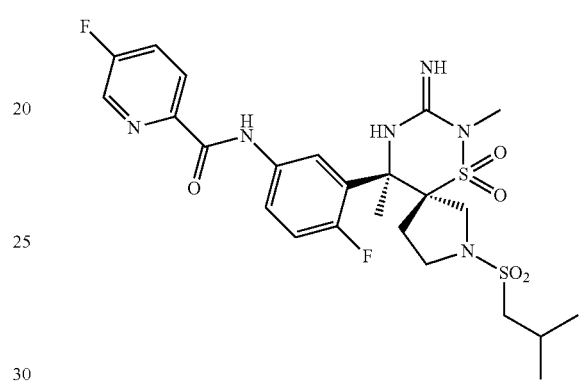
,
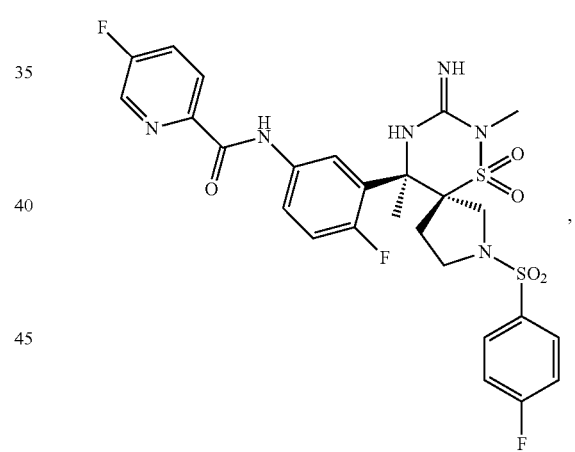
,
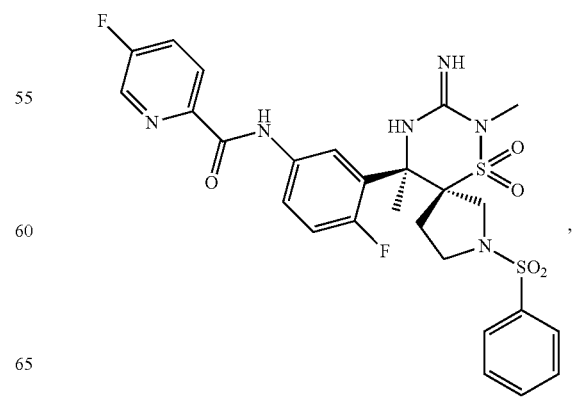
, 125
-continued
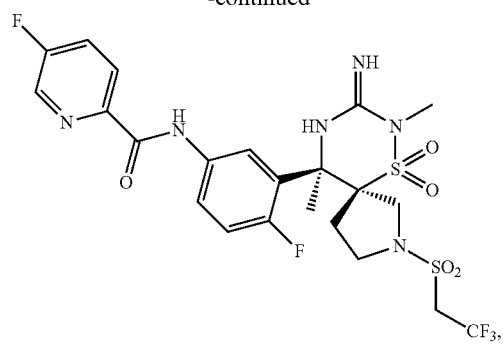
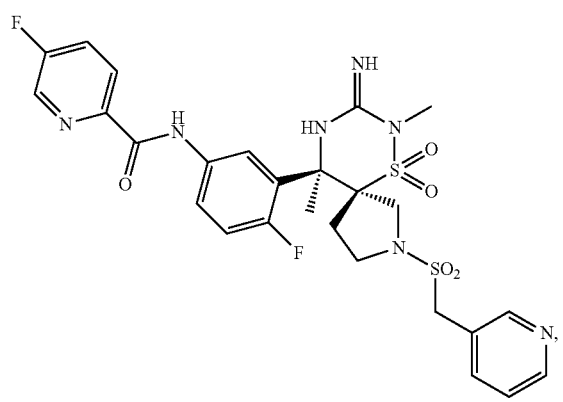
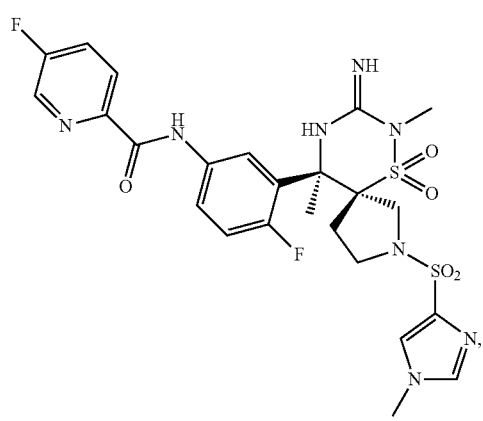
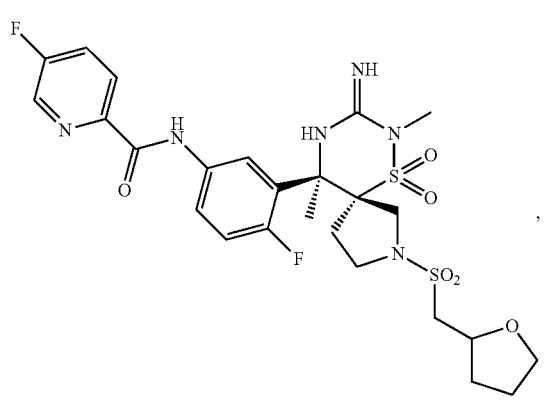
126
-continued
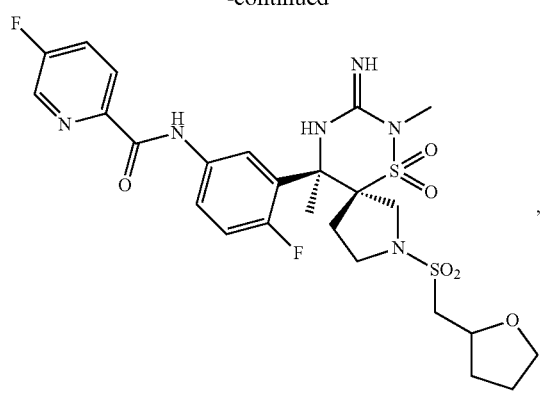
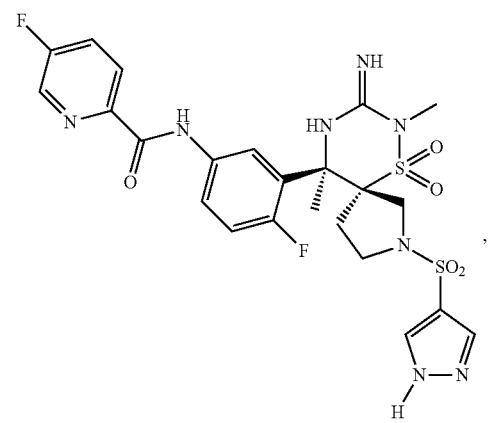
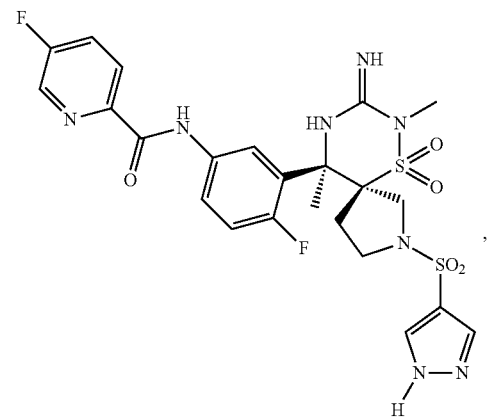
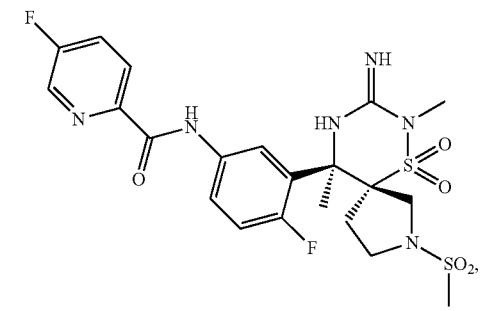

127
-continued
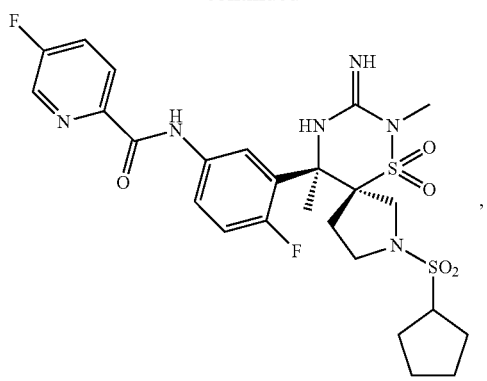
,
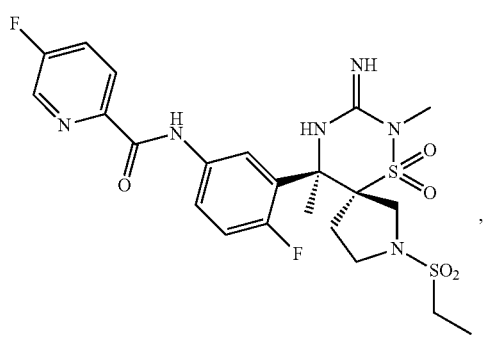
,
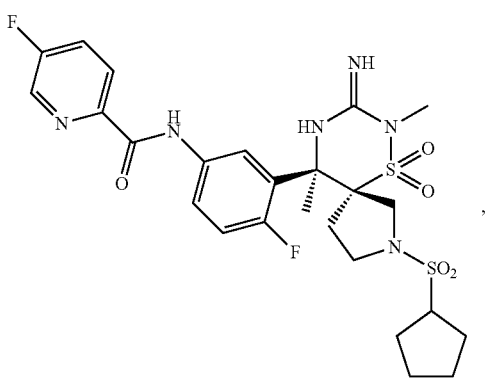
,
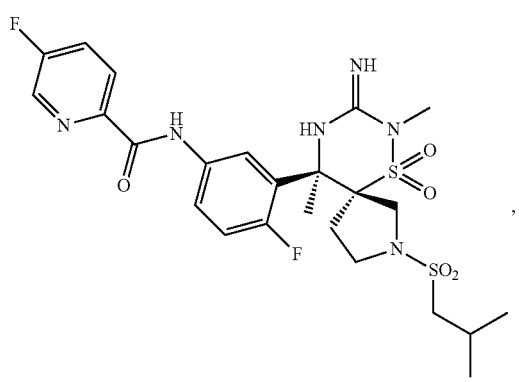
,
128
-continued
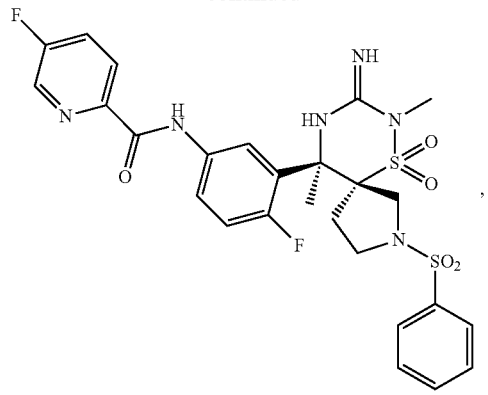
,
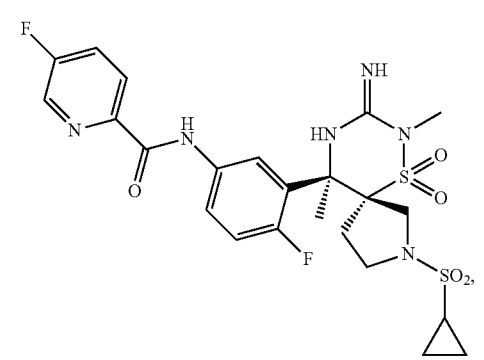
,
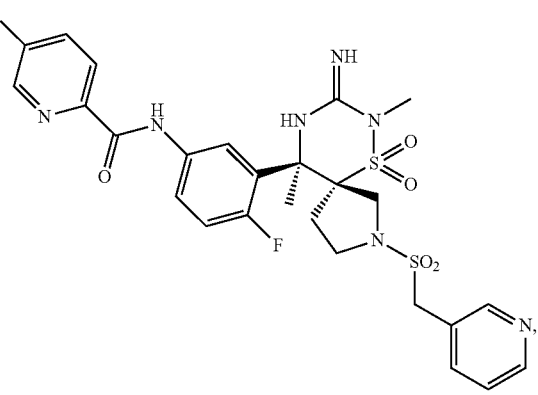
,
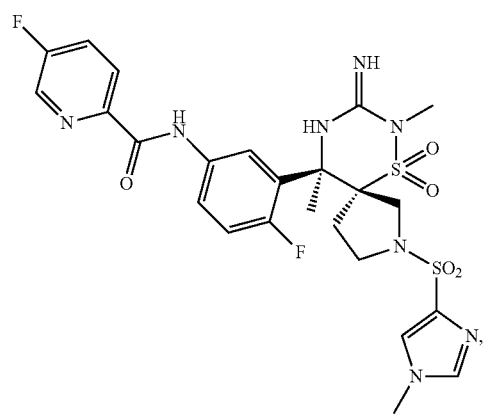

-continued

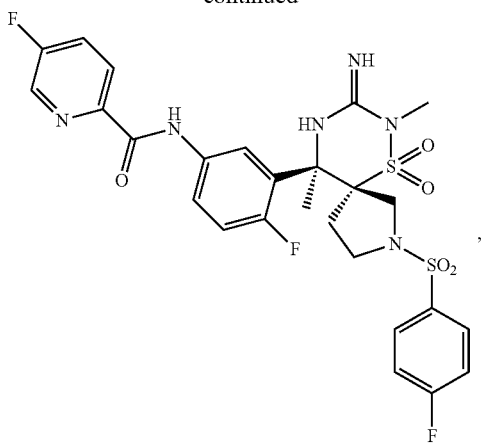

,

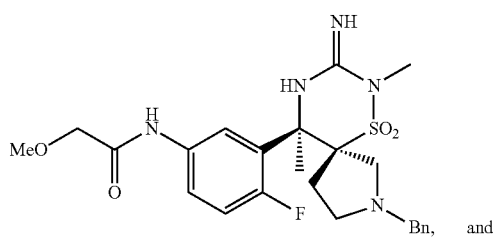
Bn, and

-continued

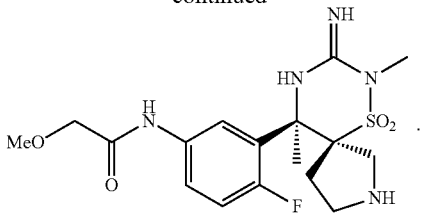

.

9. A pharmaceutical composition comprising a compound according to claim 1, or a tautomer thereof, or a pharmaceutically acceptable salt of said compound or said tautomer, and a pharmaceutically acceptable carrier or diluent.

10. A method of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease, said method comprising administering a compound according to claim 1, or a tautomer thereof, or a pharmaceutically acceptable salt of said compound or said tautomer, to a patient in need thereof in an amount effective to treat said disease or pathology.

11. The method of claim 10, wherein disease or pathology is Alzheimer's disease.

* * * * *